US009260417B2

(12) United States Patent
Murphy et al.

(10) Patent No.: US 9,260,417 B2
(45) Date of Patent: Feb. 16, 2016

(54) THERAPEUTIC METHODS AND COMPOSITIONS INVOLVING ALLOSTERIC KINASE INHIBITION

(75) Inventors: Eric A. Murphy, San Marcos, CA (US); David A. Cheresh, Encinitas, CA (US); Lee Daniel Arnold, Mt. Sinai, NY (US)

(73) Assignee: AMITECH THERAPEUTIC SOLUTIONS, INC., La Jolla, CA (US)

( * ) Notice: Subject to any disclaimer, the term of this patent is extended or adjusted under 35 U.S.C. 154(b) by 275 days.

(21) Appl. No.: 13/577,431

(22) PCT Filed: Feb. 7, 2011

(86) PCT No.: PCT/US2011/023949
§ 371 (c)(1),
(2), (4) Date: Dec. 5, 2013

(87) PCT Pub. No.: WO2011/097594
PCT Pub. Date: Aug. 11, 2011

(65) Prior Publication Data
US 2014/0296268 A1 Oct. 2, 2014

Related U.S. Application Data

(60) Provisional application No. 61/302,471, filed on Feb. 8, 2010, provisional application No. 61/310,663, filed on Mar. 4, 2010.

(51) Int. Cl.
*A61K 31/505* (2006.01)
*C07D 403/12* (2006.01)

(52) U.S. Cl.
CPC .................................... *C07D 403/12* (2013.01)

(58) Field of Classification Search
CPC ............................ C07D 403/12; A61K 31/505
See application file for complete search history.

(56) References Cited

U.S. PATENT DOCUMENTS

| | | | |
|---|---|---|---|
| 2,789,118 A | 4/1957 | Bernstein et al. |
| 2,990,401 A | 6/1961 | Bernstein et al. |
| 3,048,581 A | 8/1962 | Fried et al. |
| 3,126,375 A | 3/1964 | Ringold et al. |
| 3,598,122 A | 8/1971 | Zaffaroni |
| 3,598,123 A | 8/1971 | Zaffaroni |
| 3,710,795 A | 1/1973 | Higuchi et al. |
| 3,731,683 A | 5/1973 | Zaffaroni |
| 3,742,951 A | 7/1973 | Zaffaroni |
| 3,749,712 A | 7/1973 | Cavazza et al. |
| 3,814,097 A | 6/1974 | Ganderton et al. |
| 3,921,636 A | 11/1975 | Zaffaroni |
| 3,928,326 A | 12/1975 | Brattsand et al. |
| 3,929,768 A | 12/1975 | Brattsand et al. |
| 3,972,995 A | 8/1976 | Tsuk et al. |
| 3,993,072 A | 11/1976 | Zaffaroni |
| 3,993,073 A | 11/1976 | Zaffaroni |
| 3,996,359 A | 12/1976 | Brattsand et al. |
| 3,996,934 A | 12/1976 | Zaffaroni |
| 4,031,893 A | 6/1977 | Kaplan et al. |
| 4,031,894 A | 6/1977 | Urquhart et al. |
| 4,060,084 A | 11/1977 | Chandrasekaran et al. |
| 4,069,307 A | 1/1978 | Higuchi et al. |
| 4,077,407 A | 3/1978 | Theeuwes et al. |
| 4,201,211 A | 5/1980 | Chandrasekaran et al. |
| 4,230,105 A | 10/1980 | Harwood |
| 4,292,299 A | 9/1981 | Suzuki et al. |
| 4,292,303 A | 9/1981 | Keith et al. |
| 4,476,116 A | 10/1984 | Shabbir |
| 4,782,084 A | 11/1988 | Vyas et al. |
| 4,885,314 A | 12/1989 | Vyas et al. |
| 5,116,817 A | 5/1992 | Anik |
| 5,336,168 A | 8/1994 | Sibalis |
| 5,358,489 A | 10/1994 | Wyrick |
| 5,540,664 A | 7/1996 | Wyrick |
| 5,665,071 A | 9/1997 | Wyrick |
| 5,665,378 A | 9/1997 | Davis et al. |
| 5,695,472 A | 12/1997 | Wyrick |
| 5,837,280 A | 11/1998 | Kenealy et al. |
| 5,869,090 A | 2/1999 | Rosenbaum |
| 6,391,452 B1 | 5/2002 | Antonsen et al. |
| 6,923,983 B2 | 8/2005 | Morgan et al. |
| 6,929,801 B2 | 8/2005 | Klose et al. |
| 6,946,144 B1 | 9/2005 | Jordan |

FOREIGN PATENT DOCUMENTS

| | | |
|---|---|---|
| WO | WO-2005-087297 | 9/2005 |
| WO | WO 2006024034 A1 * | 3/2006 |
| WO | WO-2006-081230 | 8/2006 |

OTHER PUBLICATIONS

National Cancer Institute. "Cancer Prevention Overview (PDQ)." (2014), Available from: <http://www.cancer.gov/cancertopics/pdq/prevention/overview/patient/page3/print >.*
American Cancer Society. "When Cancer Doesn't Go Away." (2014), Available from: <http://www.cancer.org/treatment/survivorshipduringandaftertreatment/when-cancer-doesnt-go-away >.*
American Cancer Society. "Cancer Types." (2013), Available from: <http://www.cancer.org/cancer/showallcancertypes/index >.*
Zhang, J., et al. "Targeting cancer with small molecule kinase inhibitors." Nature. (Jan. 2009), vol. 9, pp. 28-39.*
Achen et al., "Vascular endothelial growth factor D (VEGF-D) is a ligand for the tyrosine kinases VEGF receptor 2 (Flk1) and VEGF receptor 3 (Flt4)," PNAS USA 95: 548-553 (1998).

(Continued)

*Primary Examiner* — Andrew D Kosar
*Assistant Examiner* — John S Kenyon
(74) *Attorney, Agent, or Firm* — Wilson Sonsini Goodrich & Rosati

(57) ABSTRACT

The present invention is directed to methods and compositions for suppressing lymphangiogenesis, angiogenesis and/or tumor growth. The methods comprise contacting the tumor with a compound that (i) stabilizes a protein kinase in the inactive state and (ii) is not an ATP competitive inhibitor of the protein kinase in the active state.

19 Claims, 38 Drawing Sheets

(56) References Cited

OTHER PUBLICATIONS

Alavi et al., "Chemoresistance of endothelial cells induced by basic fibroblast growth factor depends on Raf-1-mediated inhibition of the proapoptotic kinase, ASK1," Cancer Res 67: 2766 (2007).

Amoh et al., "Nestin-linked green fluorescent protein transgenic nude mouse for imaging human tumor angiogenesis," Cancer Res 65: 5352-5357 (2005).

Amoh et al., "Dual-color imaging of nascent blood vessels vascularizing pancreatic cancer in an orthotopic model demonstrates antiangiogenesis efficacy of gemcitabine," J Surg Res 132: 164-169 (2006).

An et al., "Development of a high metastatic orthotopic model of human renal cell carcinoma in nude mice: benefits of fragment implantation compared to cell-suspension injection," Clin Exp Metastasis 17: 265-270 (1999).

Beeram et al., "Raf: a strategic target for therapeutic development against cancer," Journal of Clinical Oncology 23: 6771-6790 (2005).

Bouvet et al., "Real-time optical imaging of primary tumor growth and multiple metastatic events in a pancreatic cancer orthotopic model," Cancer Res 62: 1534-1540 (2002).

Byzova et al., "Adenovirus encoding vascular endothelial growth factor-D induces tissue-specific vascular patterns in vivo," Blood 99: 4434-4442 (2002).

Dougherty et al., "KSR2 is a calcineurin substrate that promotes ERK cascade activation in response to calcium signals," Mol Cell 34: 652-662 (2009).

Eliceiri et al., "Selective requirement for Src kinases during VEGF-induced angiogenesis and vascular permeability," Molecular Cell 4: 915-924 (1999).

Englesbe et al., "Concomitant blockade of platelet-derived growth factor receptors alpha and beta induces intimal atrophy in baboon PTFE grafts," J Vasc Surg 39: 440-446 (2004).

Fukuda et al., "The pseudoactive site of ILK is essential for its binding to alpha-Parvin and localization to focal adhesions," Mol Cell 36: 819-830 (2009).

Garnett et al., "Wild-type and mutant B-RAF activate C-RAF through distinct mechanisms involving heterodimerization," Molecular Cell 20: 963-969 (2005).

PCT Application No. PCT/US2011/023949 International Search Report mailed Oct. 24, 2011.

PCT Application No. PCT/US2011/023949 International Preliminary Report on Patentability mailed Aug. 14, 2012.

Joukov et al., "A novel vascular endothelial growth factor, VEGF-C, is a ligand for the Flt4 (VEGFR-3) and KDR (VEGFR-2) receptor tyrosine kinases," EMBO J. 15: 290-298 (1996).

Kang et al., "VRK3-mediated inactivation of ERK signaling in adult and embryonic rodent tissues," Biochim Biophys Acta 1783: 49-58 (2008).

Kang et al., "Negative regulation of ERK activity by VRK3-mediated activation of VHR phosphatase," Nat Cell Biol 8: 863-869 (2006).

Karaman et al., "A quantitative analysis of kinase inhibitor selectivity," Nature Biotechnology 26: 127-132 (2008).

Katz et al., "Selective antimetastatic activity of cytosine analog CS-682 in a red fluorescent protein orthotopic model of pancreatic cancer," Cancer Res 63: 5521-5525 (2003).

Koh et al., "In vitro three dimensional collagen matrix models of endothelial lumen formation during vasculogenesis and angiogenesis," Methods in Enzymology 443: 83-101 (2008).

Lawson et al., "In vivo imaging of embryonic vascular development using transgenic zebrafish," Dev Biol 248: 307-318 (2002).

Legate et al., "ILK, PINCH and parvin: the tIPP of integrin signalling," Nat Rev Mol Cell Biol 7: 20-31 (2006).

Li et al., "Ablation of MEK kinase 1 suppresses intimal hyperplasia by impairing smooth muscle cell migration and urokinase plasminogen activator expression in a mouse blood-flow cessation model," Circulation 111: 1672-1678 (2005).

Liu et al., "Rational design of inhibitors that bind to inactive kinase conformations," Nature Chemical Biology 2: 358-364 (2006).

Marconcini et al., "c-fos-induced growth factor/vascular endothelial growth factor D induces angiogenesis in vivo and in vitro," PNAS USA 96: 9671-9676 (1999).

Okram et al., "general strategy for creating "inactive-conformation" abl inhibitors," Chemistry & Biology 13: 779-786 (2006).

Pintucci et al., "Anti-proliferative and anti-inflammatory effects of topical MAPK inhibition in arterialized vein grafts," FASEB J 20: 398-400 (2006).

Rushworth et al., "Regulation and role of Raf-1/B-Raf heterodimerization," Mol Cell Biol 26: 2262-2272 (2006).

Schnabl et al., "Immortal activated human hepatic stellate cells generated by ectopic telomerase expression," Laboratory investigation; a journal of technical methods and pathology 82: 323-333 (2002).

Stacker et al., "The role of tumor lymphangiogenesis in metastatic spread," FASEB J. 16: 922-934 (2002).

Stanton et al., "Yaf2 inhibits caspase 8-mediated apoptosis and regulates cell survival during zebrafish embryogenesis," The Journal of Biological Chemistry 281: 28782-28793 (2006).

Tsuji et al., "Common bile duct injection as a novel method for establishing red fluorescent protein (RFP)-expressing human pancreatic cancer in nude mice," Jop 7: 193-199 (2006).

Veikkola et al., "Signalling via vascular endothelial growth factor receptor-3 is sufficient for lymphangiogenesis in transgenic mice," EMBO J. 20: 1223-1231 (2001).

Weber et al., "Active Ras induces heterodimerization of cRaf and Braf," Cancer Res 61: 3595-3598 (2001).

Yalpani, M., "Cholesterol Lowering Drugs," Chemistry and Industry, pp. 85-89 (Feb. 5, 1996).

Zeqiraj et al., "ATP and MO25alpha regulate the conformational state of the STRADalpha pseudokinase and activation of the LKB1 tumour suppressor," PLoS Biol 7: e1000126 (2009).

Zeqiraj et al., "Structure of the LKB1-STRAD-MO25 complex reveals an allosteric mechanism of kinase activation," Science 326: 1707-1711 (2009).

* cited by examiner

| Compound | $R_1$ | $R_2$ | Z | $R_3$ | p-PDGFRβ VSMCs | p-MEK ECs |
|---|---|---|---|---|---|---|
| 3 | - | NH2 | NH | - | ++ | - |
| 4 | NH2 | NH2 | NH | - | ++ | - |
| 5 | NH2 | NH2 | NH | Cl | - | ++ |
| 6 | MeS | NH2 | NH | - | ++ | ++ |
| 7 | MeS | - | NH | - | + | ++ |
| 8 | MeS | NH2 | NH | Cl | - | ++ |
| 9 | NH2 | MeO | NH | - | ++ | ++ |
| 10 | NH2 | NH2 | O | - | - | + |
| 11 | MeS | NH2 | O | - | - | + |

FIG. 2
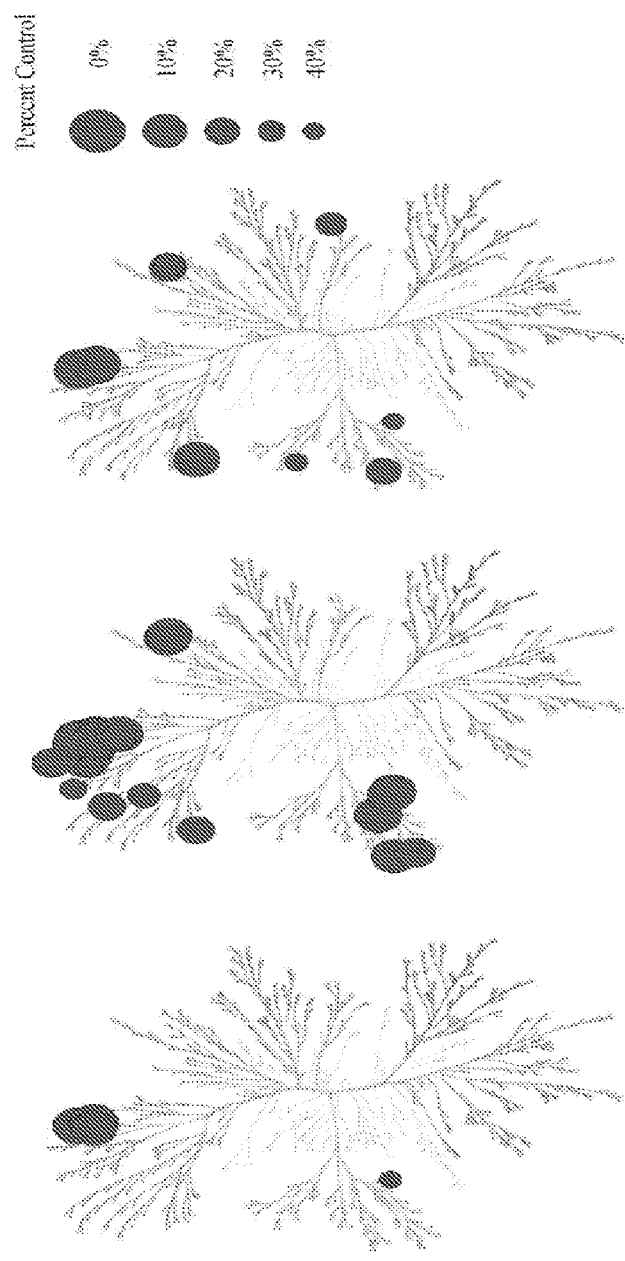
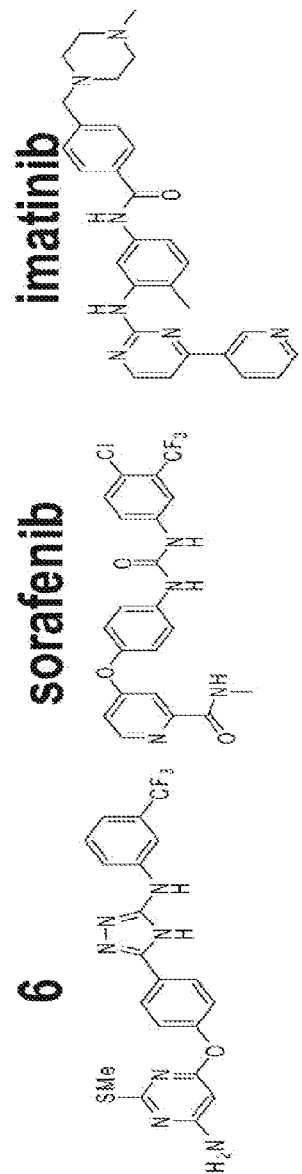

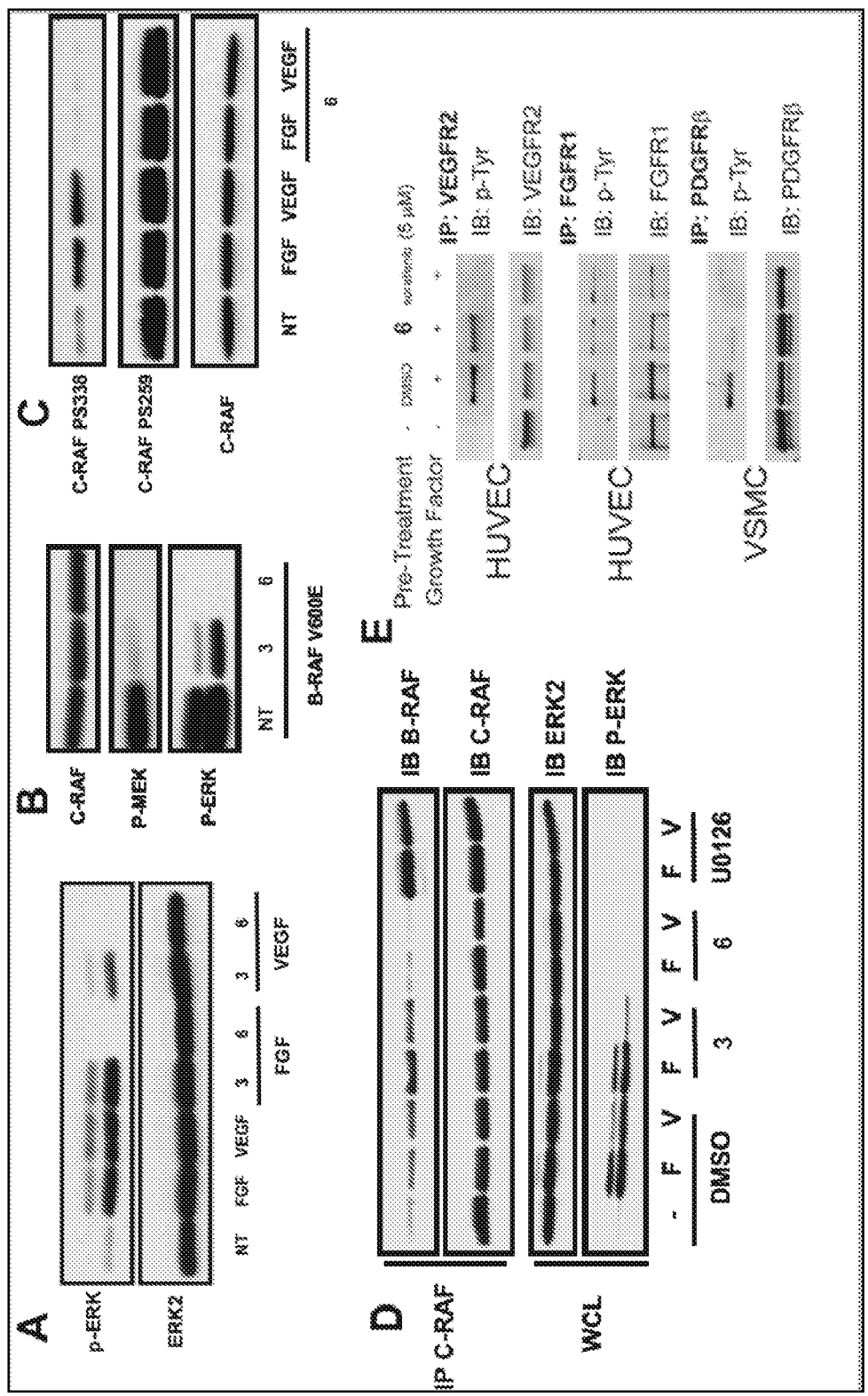
FIG. 7A-E

FIG. 8A-B
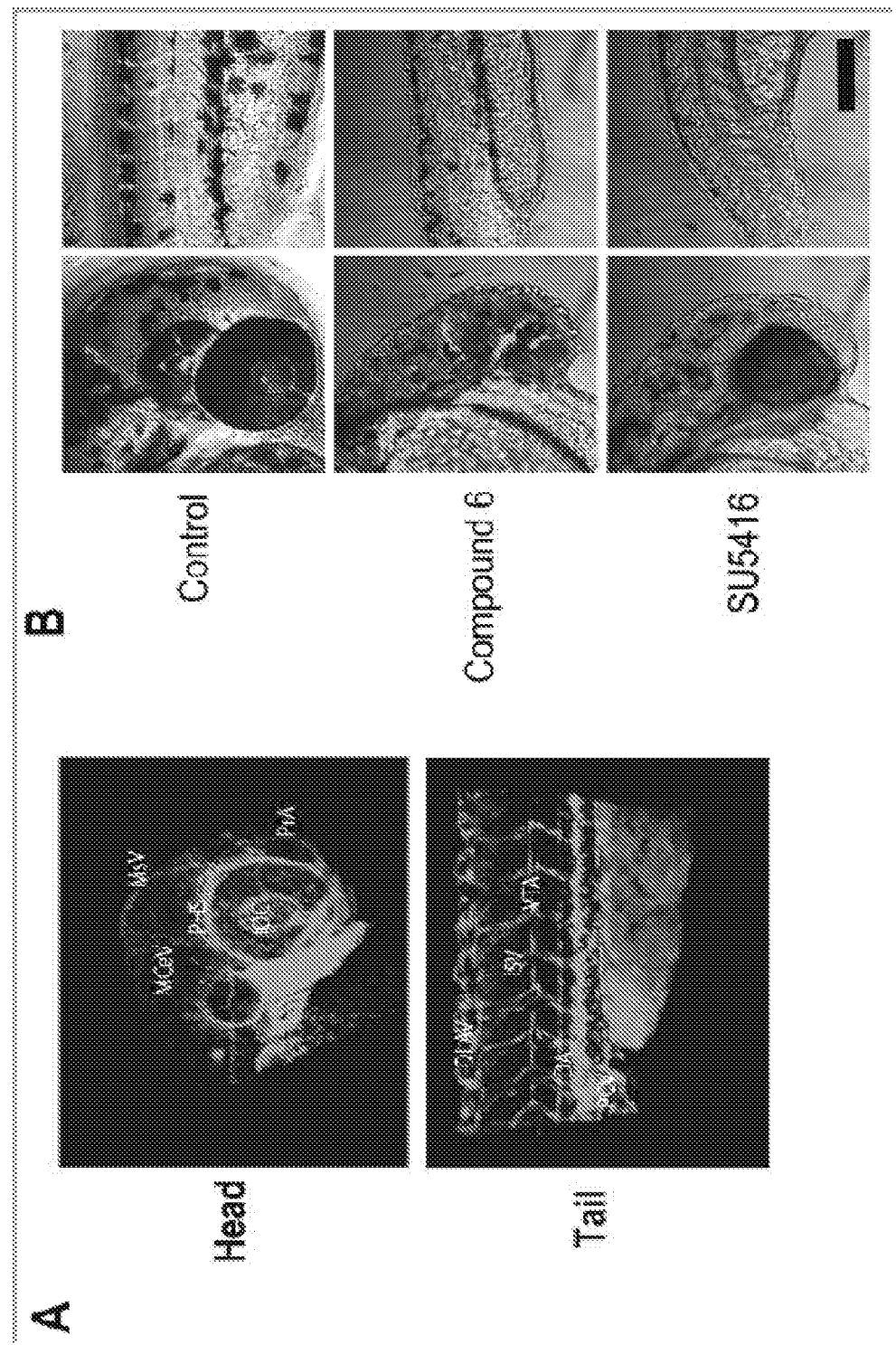

FIG. 8C-D
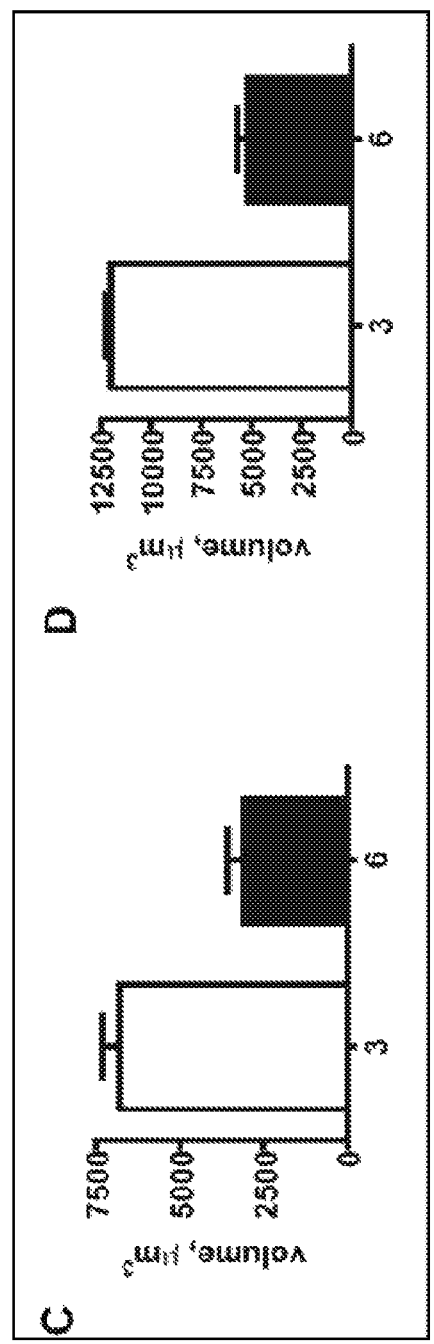

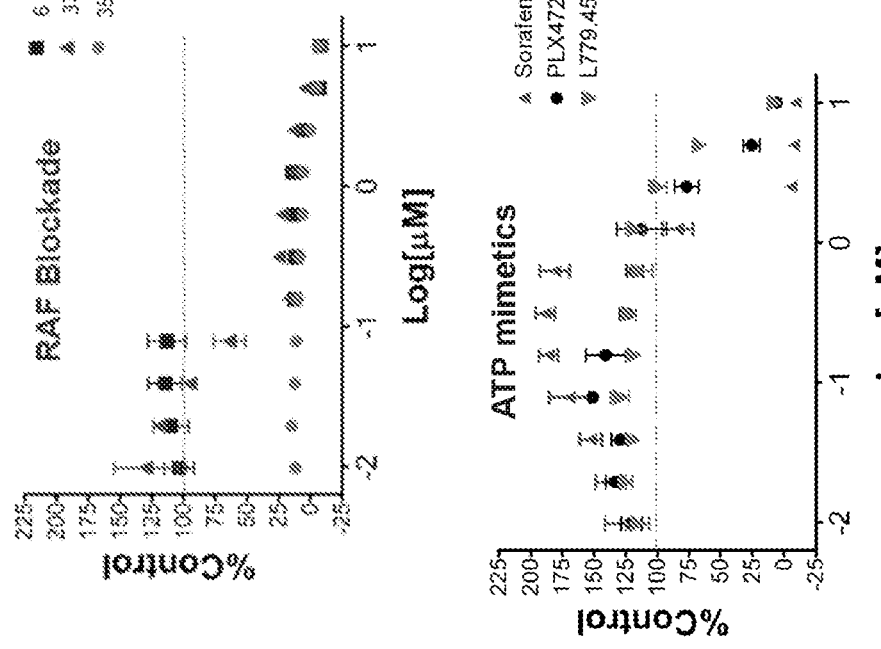

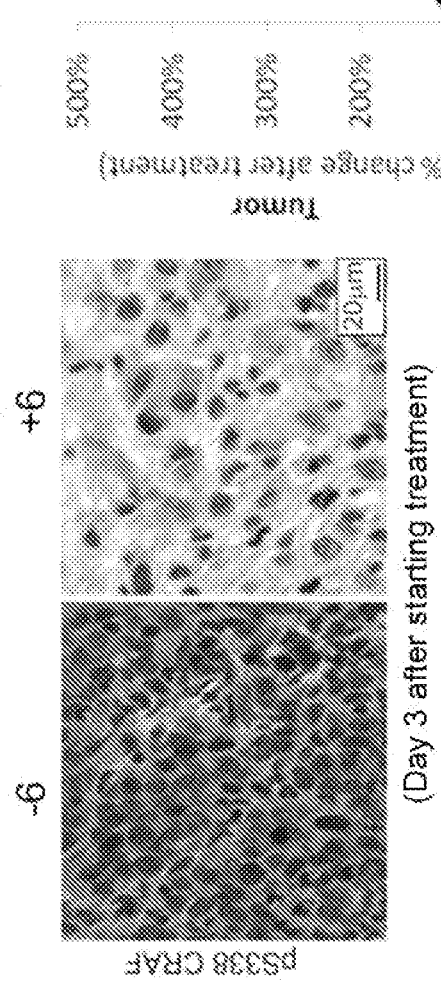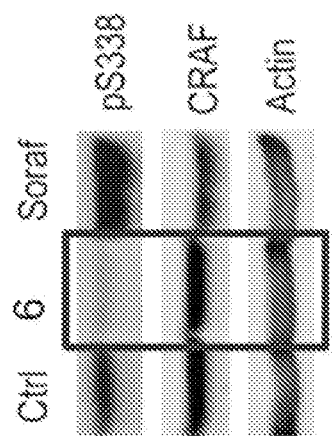
FIG. 18A  FIG. 18B  FIG. 18C

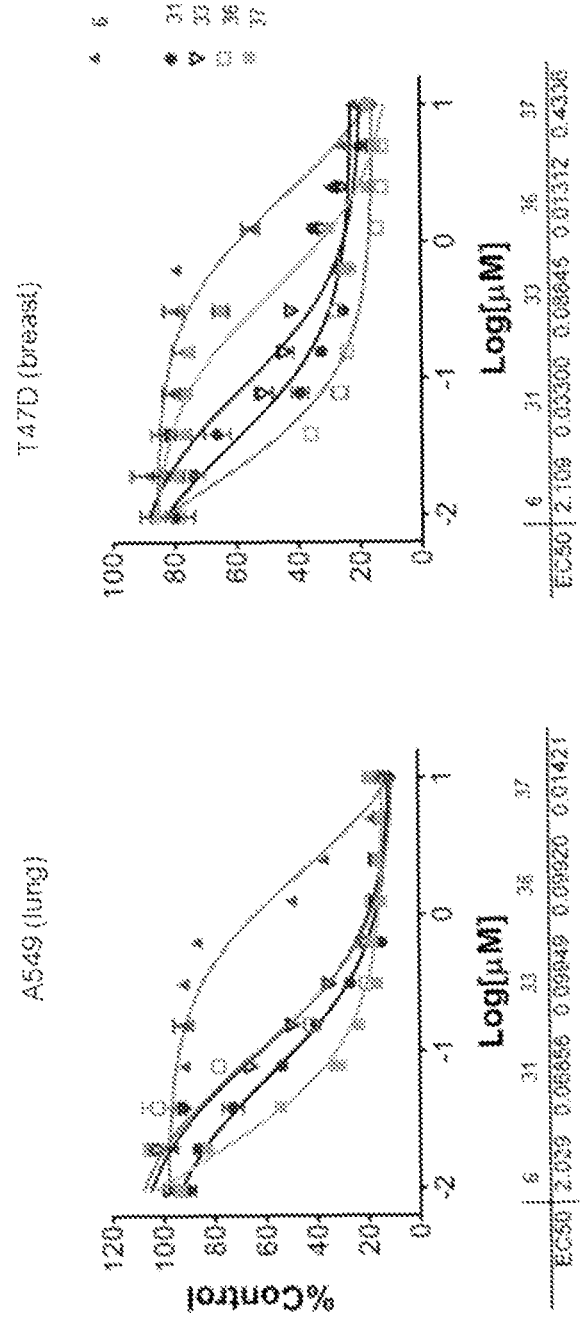

THERAPEUTIC METHODS AND COMPOSITIONS INVOLVING ALLOSTERIC KINASE INHIBITION

CROSS-REFERENCE

This patent application is a national phase application of PCT Application serial number PCT/US2011/023949 filed on Feb. 7, 2011 and claims the benefit of U.S. Provisional Patent Application No. 16/302,471, filed Feb. 8, 2010 and U.S. Provisional Patent Application No. 61/310,663, filed Mar. 4, 2010 which applications are incorporated herein by reference.

STATEMENT AS TO FEDERALLY SPONSORED RESEARCH

This invention was made with the support of the United States government by grants from the NIH: P01-CA078045 (DAC), P01-HL057900 (DAC), and P01-CA104898 (DAC).

BACKGROUND OF THE INVENTION

Kinases regulate fundamental processes in cancer including tumor proliferation, metastasis, neovascularization, and chemoresistance. Accordingly, kinase inhibitors have been a major focus of drug development and several kinase inhibitors are now approved for various cancer indications. Typically, kinase inhibitors are selected via high throughput screening using catalytic kinase domains at low ATP concentration and this process often yields ATP mimetics that lack specificity and/or function poorly in cells where ATP levels are high.

SUMMARY OF THE INVENTION

In one aspect provides herein compounds having the structure

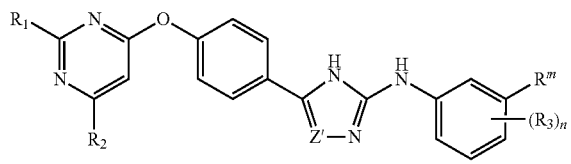

or an N-oxide, N,N'-dioxide, N,N',N''-trioxide, or a pharmaceutically acceptable salt thereof, wherein $R_1$ and $R_2$ are independently hydrogen, optional substituted alkyl, halogen, optional substituted amine, $NH_2$, optional substituted alkyoxy, optional substituted thioalkyl, $CF_3S$, optional substituted alkylsulfinyl or optional substituted alkylsulfonyl; Z' is N or C; $R^m$ is $C_{1-6}$ alkyl, or halogen substituted $C_{1-6}$ alkyl; and $R_3$ is independently a hydrogen, $C_{1-6}$ alkyl, halogen substituted $C_{1-6}$ alkyl, halogen substituted $C_{1-6}$ alkoxy, or $C_{3-10}$ cycloalkyl; or, optionally, $R^m$ and $R_3$ are joined to form a five to seven membered carbocycle; and n is 0-4.

In another aspect, there are provided processes for preparing a compound of formula I:

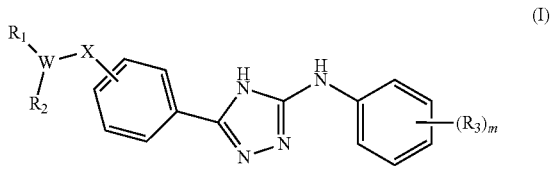

comprising reacting a compound of formula II,

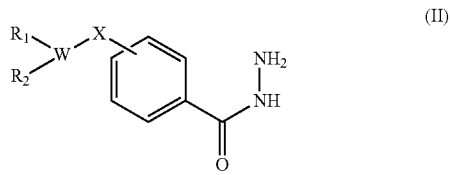

with a compound of formula (III),

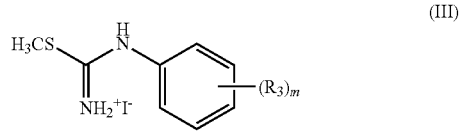

in the presence of a base, wherein W is selected from the group consisting of pyridine, pyridazine, pyrimidine, pyrazine, triazine, quinoline, isoquinoline, cinnoline, quinazoline, quinoxaline, 1,2,4-benzotriazine and azaindole; X is O, S or NH; $R_1$ and $R_2$ are independently a hydrogen, optional substituted alkyl, halogen, optional substituted amine, $-NH_2$, $-OH$, optional substituted alkoxy, optional substituted thioalkyl, $-SCF_3$, optional substituted alkylsulfinyl or an optional substituted alkylsulfonyl; $R_3$ is independently a hydrogen, halogen substituted $C_{1-6}$ alkyl, or halogen substituted $C_{1-6}$ alkoxy and m is 1-5.

In another aspect, there are provided processes for preparing a compound of formula Ia:

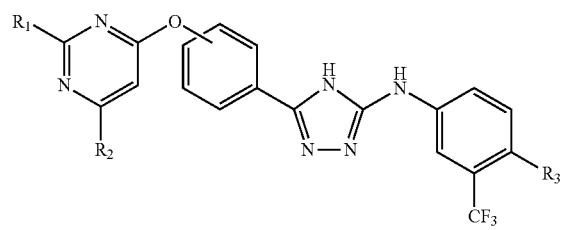

comprising reacting a compound of formula IIa,

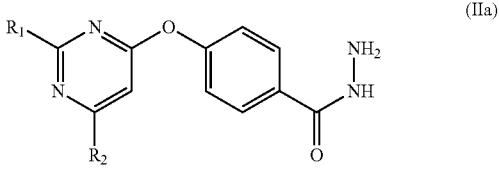

with a compound of formula (IIIa),

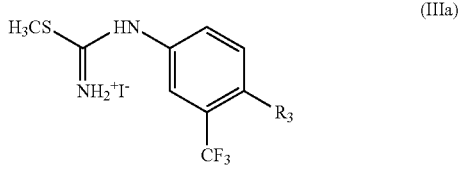

in the presence of a base, wherein $R_1$ and $R_2$ are independently a hydrogen, optional substituted alkyl, halogen, optional substituted amine, —$NH_2$, —OH, optional substituted alkoxy, optional substituted thioalkyl, —$SCF_3$, optional substituted alkylsulfinyl or an optional substituted alkylsulfonyl and $R_3$ is a hydrogen, halogen, substituted $C_{1-6}$ alkyl, or halogen substituted $C_{1-6}$ alkoxy.

In another aspect of the present invention, there are provided processes for preparing a compound of formula IV:

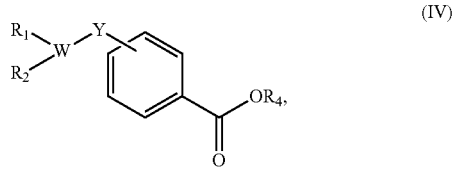

comprising reacting a compound of formula V,

with a compound of formula (VI),

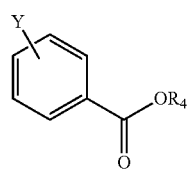

in the presence of a base wherein L is a leaving group; Y is —SH, —OH, or —$NH_2$; $R_1$ and $R_2$ are independently hydrogen, optional substituted alkyl, halogen, optional substituted protected amine, optional substituted alkoxy, optional substituted thioalkyl, $CF_3S$, optional substituted alkylsulfinyl or optional substituted alkylsulfonyl and $R_4$ is a $C_{1-6}$ alkyl.

Also provided herein are methods for lymphangiogenesis, angiogenesis and/or growth of a tumor. The methods comprise contacting the tumor with a compound that (i) stabilizing a protein kinase in the inactive state and (ii) is not an ATP competitive inhibitor of the protein kinase in the active state.

In another aspect, methods for treating cancer in a human subject provided herein comprise administering to a patient in need a compound that (i) stabilizes a protein kinase in the inactive state and (ii) is not an ATP competitive inhibitor of the protein kinase in the active state.

In another aspect, there are provided methods for preventing inhibition of ASK1-mediated apoptosis in a cell comprising contacting the cell with a compound that (i) stabilizes the protein kinase in the inactive state and (ii) is not an ATP competitive inhibitor of the protein kinase in the active state.

In another aspect, methods for sensitizing a cell to an extrinsic stress provided herein comprise contacting the cell with a compound that (i) stabilizes the protein kinase in the inactive state and (ii) is not an ATP competitive inhibitor of the protein kinase in the active state.

In another aspect, there provided methods for inhibiting MEK1/2- and/or ERK1/2-mediated cellular proliferation or migration comprising contacting a cell with a compound that (i) stabilizes the protein kinase in the inactive state and (ii) is not an ATP competitive inhibitor of the protein kinase in the active state.

In another aspect, there are provided methods for treating restenosis in a human subject comprising administering to a patient in need a compound that (i) stabilizes a protein kinase in the inactive state and (ii) is not an ATP competitive inhibitor of the protein kinase in the active state.

In another aspect, methods for treating fibrotic diseases in a human subject provided herein comprise administering to a patient in need a compound that (i) stabilizes a protein kinase in the inactive state and (ii) is not an ATP competitive inhibitor of the protein kinase in the active state.

In another aspect, there provided methods for inhibiting phosphorylation of S338 of CRAF and/or RAF dimerization comprising contacting a cell with a compound that (i) stabilizes the protein kinase in the inactive state and (ii) is not an ATP competitive inhibitor of the protein kinase in the active state.

The present invention also provides methods for identifying allosteric inhibitors of RAF kinase. The methods comprise contacting a RAF kinase with test compounds and monitoring the phosphorylation of S338 of CRAF, wherein a decrease in the phosphorylation of S338 of CRAF relative to non-contacted RAF kinase indicates that the test compounds are allosteric inhibitor of RAF kinase.

INCORPORATION BY REFERENCE

All publications, patents, and patent applications mentioned in this specification are herein incorporated by reference for the purposes.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

(FIG. 1A) Molecular modeling of the amino-triazole based small molecules in PDGFRβ and RAF, respectively. The crystal structure of B-RAF (PDB 1uwh) was selected for binding studies since it contained the DFG motif of the activation loop in the desirable inactive state (i.e. DFG-out). A homology model of PDGFRβ was created with a structurally-related family member (VEGFR2, PDB 1y6b). Further docking studies are provided in FIG. 6B. (FIG. 1B) Human vascular smooth muscle cells (VSMC) were pre-treated with compound 6 (0, 0.5, 1, and 10 μM) for 1 h followed by 7 min stimulation with PDGF-BB and lysis in RIPA buffer. To autophosphorylation, immunoblots were carried out with a phospho-tyrosine antibody. Membranes were stripped and reprobed for total PDGFRβ levels. (FIG. 1C) Western analysis demonstrating compound 6 (5 µM) inhibition of bFGF or VEGF (50 ng/ml, 5 min stimulation) induced phosphorylation of MEK and ERK in serum starved HUVECs. A comparison of endothelial cell-based RAF inhibition of compounds 3 and 6 can be found in FIG. 7A). (FIG. 1D) Structure activity relationships of the amino-triazole based small molecules comparing both PDGFRβ and B-RAF. Compounds 3 through 11 were prepared (U.S. Pat. No. 7,652,051) and screened for inhibition of PDGF-BB induced PDGFRβ autophosphorylation in VSMCs at 2 µM or bFGF induced MAPK activity in HUVECs at 5 µM by Western analysis (− denotes x<10%, + denotes 50%<x<70%, and ++ denotes x>90% inhibition). XTT viability assay in which VSMCs (FIG. 1E) or HUVECs (FIG. 1F) were treated with compounds 3, 6, imatinib, or sorafenib at various doses for 72 h in full growth medium containing 10% FBS. Curves represent the average of 3 separate experiments, error bars represent ±SEM.

FIG. 2 provides illustrative profiles of compound 6, sorafenib, and imatinib in the KINOMEscan™ profiling service from Ambit Biosciences. The compounds were screened against 70 kinases for competitive binding and the legend describes % control (inhibition relative to positive control) of the kinase targets at 10 µM. The complete list of kinases screened as well as % inhibition is available in Table 2 and a list of the Kds of the kinase targets for compound 6 can be found in Table 3.

(FIG. 3A) Effect of compound 6 on angiogenesis in transgenic fli1-egfp zebrafish embryos. Embryos were treated with 1 µM 6 or SU5416, or 10 µM 3 from 20 hours post fertilization (hpf) until 48 hpf. Representative 3D reconstructions of the blood vasculature are shown for both the head and tail regions of the embryo. Designations for the major vessels in the head and tail of the zebrafish embryo at 48 hpf are available in FIG. 8A. (FIG. 3B) Disruption of lumen formation in the zebrafish during late vessel maturation. Zebrafish treated with either 1 µM 6 or 10 µM 3 from 20-48 hpf were imaged at 35 and 48 hpf. Bottom panel: compound 6 induces apoptosis in the intersegmental vessels in the zebrafish. Shown is 3D overlap reconstruction of the GFP expressing intersegmental vessels with TUNEL-positive nuclei at 48 hpf (shown in red). Representative phase contrast views as well as quantification of intersegmental vessel volumes from FIG. 3A and FIG. 3B can be found in FIG. 8B-D, respectively. (FIG. 3C) Time course of drug addition to zebrafish. Compounds (2.5 µM for 3 or 6, 1 µM sorafenib, or DMSO as control) were added at either 18 hpf or 30 hpf (left on the embryos for the duration of the experiment) and intersegmental vessels were imaged approximately 24 h after the time point corresponding to drug addition. At 30 hpf the zebrafish embryos established early vessels with evident lumens. Compound 6 and sorafenib were added to evaluate their effect on pre-existing vasculature. (FIG. 3D) Phase contrast images of zebrafish treated with compounds 3, 6, or sorafenib (same concentrations as in FIG. 3C). The images demonstrate that embryos treated with 3 and 6 are viable whereas sorafenib causes death. n=4-6 zebrafish embryos per condition for all treatments. All scale bars=100 µm.

(FIG. 4A) Effect of compounds 3, 6, vatalanib, imatinib, GW 5074 and a combination of imatinib (PDGFR inhibitor) and GW 5074 (RAF inhibitor) on intersegmental vessel formation in Tg:(fli1-egfp) zebrafish embryos. Embryos were treated with DMSO, 5 µM compound 3, 5 µM compound 6, 1 µM vatalanib, 5 µM imatinib (Im), 1 µM GW 5074 (GW), and the combination of 5 µM imatinib and 1 µM GW 5074 (Im+GW) from 16 hours post fertilization (hpf) until 48 hpf. Z-stacks from laser scanning confocal microscopy are shown depicting formation of the intersegmental vessels at 48 hpf. n=6 embryos/treatment. (FIG. 4B) HUVECs were co-cultured with hTERT-human hepatic stellate cells in a 3-D collagen matrix in the presence of complete EBM-2 medium to monitor pericyte-associated endothelial tube formation. The stellate cells were labeled with 10 µg/ml red fluorescent dye (DiIC(3), BD Biosciences) for 1 h prior to the start of the experiment Inhibitors were added to the co-cultures 6 h post seeding at the following concentrations: DMSO, 2.5 µM 3, 2.5 µM compound 6, 1 µM imatinib (Im), 0.5 µM GW 5074 (GW), and the combination of 1 µM imatinib and 0.5 µM GW 5074 (Im+GW). The endothelial tubes were stained at 24 h by adding 2 µl FITC labeled *Ulex europaeus* lectin (Vector labs) per well. Images were acquired 48 h post seeding of the cells. One representative panel from 3 independent experiments is shown. Green—FITC lectin labeled endothelial cells, Red—DiIC(3) labeled stellate cells. Inset in each panel displays a higher magnification view of the endothelial cell/stellate cell interactions. Scale bar=200 µm. (FIG. 4C) Tube lengths were measured using Metamorph software for each tube for all 10 fields that were acquired. The % pericyte-covered tube length was calculated from the ratio of tube length sums for the tubes with and without pericyte contact. Error bars are reported as ±SEM of two wells per group. *indicates p<0.05 compared to DMSO group.

(FIG. 5A) Real-time fluorescent imaging of XPA-1-RFP pancreatic tumor xenografts in the pancreas of Nestin-GFP mice (n=5/group) treated with either vehicle or compound 6 (50 mg/kg, ip, bid). Drug treatments were started 3 days after surgical orthotopic implantation (SOI) of XPA1-RFP tumors and tumor progression was monitored every 3 days by whole animal imaging. Scale bar=10 mm. (FIG. 5B) Plot of tumor surface area over time for the vehicle and compound 6 treated groups. Tumor surface area was calculated by adding the total pixels of both the ventral and lateral images of the tumor. *p=0.034. (FIG. 5C) Average body weight of the mice measured each day of whole animal imaging described in FIGS. 5A and 5B above. (FIG. 5D) Total weights of resected primary tumors on day 15 post (SOI), *p=0.022. (FIG. 5E) Representative fluorescent images of endothelial GFP expression (GFP expression driven by the Nestin promoter) within the XPA1-RFP tumors after resection. Images taken 15 days post SOI. Scale bar=200 µm. (FIG. 5F) Plot of tumor vessel density from images acquired as in FIG. 5E. Blood vessels imaged as in 5E were converted to length (mm) and normalized to the tumor volume (mm$^3$), *p=0.01.

(FIG. 6A) 1 uwh represents the co-crystal structure of sorafenib with BRAF and 1xkk is the co-crystal structure of GW 572016 and EGFR. The sequence identity of the PDGFRβ and BRAF kinase domains (if the insert SEQ ID NO.1: LQHHSD-KRRPPSAELYSNALPVGLPLPSHVSLT-GESDGGYMDMSKDESVDYVPMLDMKGD-VKYADIESSNYMAPYDNYVPSAPERTCRATLINESPVL in PDGFRβ is excluded) is 29.1%, and overall similarity is 47.3% (opening gap penalty 15, extension gap penalty 1, using the program EMBOSS Align of EBI). (FIG. 6B) Because of the absence of sufficient crystallographic information for the activation loop in PDGFRβ, it can be modeled with a variety of possible loop conformations. By modeling the conformation of the activation loop in PDGFRβ near Gly857 using EGFR kinase (pdb id 1xkk) as a template, we observe that Gly857 will be located in close proximity to the phenyl ring of 6. Further addition of any atoms in the para position would be sterically hindered by the loop. This would be predicted to create an unstable position of 6 in the protein and potentially explains why 4-Cl is not tolerated for PDGFRβ activity.

FIG. 7A-G show illustrative results from compound 6 inhibiting RAF activity in ECs, active B-RAF V600E, phosphorylation of C-RAF S338, and heterodimerization of B-/C-RAF without affecting FGFR or VEGFR. (FIG. 7A) Western analysis comparing compound 3 and compound 6 (10 µM) inhibition of bFGF or VEGF (50 ng/ml, 5 min stimulation) induced phosphorylation of ERK in serum starved HUVECs as described herein. ERK2 staining is shown for the loading control. (FIG. 7B) 1205Lu Melanoma cells which endogenously express constitutively active B-RAF V600E were starved overnight and treated for 1 h with compound 6 (10 µM) to determine inhibition of the oncogenic B-RAF activity as measured by phosphorylation of MEK and ERK. (FIG. 7C) Phosphorylation of C-RAF within the activation segment at S338 or at the 14-3-3 binding site, S259, was determined by Western analysis. Endothelial cells were serum starved overnight and pretreated with compound 6 for 1 h before stimulation with either bFGF or VEGF at 50 ng/ml for 5 min. (FIG. 7D) Immunoprecipitation and Western analysis of B-RAF/C-RAF heterodimerization. HUVECs were serum starved overnight and treated with compounds as described in FIG. 7B above. After growth factor stimulation with bFGF (F) or VEGF (V), C-RAF was immunoprecipitated (agarose conjugated C-RAF Ab, Santa Cruz) from 400 µg of protein from total cell lysates and the presence of B-RAF (Santa Cruz) in the immunoprecipitate was determined by Western blotting. Corresponding phosphorylation of ERK in the whole cell lysates (WCL) is shown in the bottom panel. Total ERK2 and total C-RAF were included in the blots as loading controls. (FIG. 7E) Human umbilical vein endothelial cells (HUVECs) or human vascular smooth muscle cells (VSMC) were pretreated with DMSO, compound 6, or sorafenib for 1 h followed by 5 minute stimulation with growth factor and lysis in RIPA buffer. 500 µg of protein was incubated with 3 µg of antibody (sc-432 for PDGFRβ and sc-6251 Flk-1/KDR, both from Santa Cruz; and #05-149 from Upstate for FGFR1) for 1 h at 4° C. before the addition of Protein A/G PLUS agarose beads (Santa Cruz). To measure autophosphorylation, immunoblots were carried out with a phospho-tyrosine antibody (PY-20, Santa Cruz) for one hour and detected with chemiluminescence. Membranes were stripped and reprobed for total receptor levels of PDGFRβ, Flk-1/KDR, and FGFR1, respectively (sc-339, sc-504, and 05-149, from Santa Cruz and Upstate, respectively). (FIG. 7F) Immunoprecipitation and Western analysis of B-RAF/C-RAF dimerization in XPA-1 pancreatice cancer cells. Exmeplary compound 6 appears to disrupt RAF dimerization. (FIG. 7G). Immunoprecipitation and Western analysis of B-RAF/C-RAF dimerization in XPA-1 pancreatice cancer cells by exemplary compounds 6 and 37. Both compounds prevent RAF dimerization and pS338-CRAF in XPA-1 cells.

FIG. 8A-D illustrate labeling of the Tgfli1-egfp zebrafish vasculature and quantification of the drug treatment effect on the ISV volume. (FIG. 8A) Images were taken from FIG. 3A with major vascular structures labeled. In the head: MCeV, middle cerebral vein; MsV, mesencephalic vein; PHS, primary head sinus; 10C, inner optic circle; PrA, prosencephalic artery. In the tail: DLAV, dorsal longitudinal anastomotic vessel; DA, dorsal aorta; PCV, posterior cardinal vein; ISV, intersegmental vessel; VTA, vertebral artery. (FIG. 8B) Representative views of zebrafish embryos treated as in FIG. 3A (images represent merged phase and GFP fluorescence views of the head and trunk regions of Tg:fli1-EGFP embryos). Scale bar=200 µm. (FIG. 8C) Quantification of ISV volume from embryos treated as in FIG. 3A. (FIG. 8D) Quantification of ISV volume from embryos treated as in FIG. 3B. To measure the intersegmental vessel (ISV) volume, individual ISVs were digitally isolated using the Imaris countersurface/isosurface functions. 30 independent ISVs from 4 independent embryos were used for the measurement. Reported+/−sem.

(FIG. 9A) Compound 6 inhibits bFGF induced angiogenesis in the mouse Matrigel model. Mice (n=5) were injected in the flank with growth-factor depleted Matrigel loaded with 200 ng bFGF and treated for 5 days with 50 mg/kg compound 6 via ip administration twice daily (bid). On day 5 after implantation of the Matrigel, the mice were administered FITC-lectin to label blood vessels. The plugs were removed and visualized by confocal microscopy followed by homogenization and quantification of total FITC. Error bars represent ±SEM. (FIG. 9B) compound 6 inhibits phosphorylation of ERK in blood vessels. Thin sections (5 µm) of the Matrigel plugs were immunostained for vessels with an EC mix (anti-Flk, anti-CD31, anti-VE-Cadherin, and anti-endoglin). Matrigel sections were immunostained for phospho-ERK to detect in vivo inhibitory activity of compound 6 by confocal microscopy. (FIG. 9C) 6 inhibits phosphorylation of PDGFRβY751 in stromal cells. Thin sections (5 µm) of the Matrigel plugs were immunostained for pericytes and fibroblast with α-smooth muscle actin and for phospho-PDGFRβ Y751 levels. ECs were immunostained with anti-CD31. (FIG. 9D) compound 6 induces apoptosis in the endothelium but not surrounding stromal cells in the Matrigel plugs. Thin sections (5 µm) of the Matrigel plugs were immunostained for vessels with an EC mix (described as in 9B). TOPRO-3 was used as a nuclear counterstain and TUNEL staining was used to detect apoptotic nuclei. Images were taken using confocal laser scanning microscopy. (n=4 plugs/group in 9B, 9C, 9D). Scale bars=200 µm (9A,9C,9D); 100 µm for (9B).

(FIG. 10A) Real-time fluorescent imaging of SN12C-RFP renal cells orthotopically injected into the flanks of nu/nu mice. Mice were treated with either vehicle or compound 6 (100 mg/kg, po, qd). Drug treatments were started 7 days after orthotopic injection and tumor growth was visualized every 7 days by whole animal imaging. The images shown are of 4 mice in the vehicle and drug treated groups on day 26. Scale bar=10 mm. (FIG. 10B) At the end of the study, both the left tumor bearing kidney and right kidney were extracted and weighed. The graph shows the mean difference in weight between the tumor-bearing kidney and the normal kidney in each animal. n=6 animals/group. *p=0.05.

(FIG. 11A) Mouse carotid arteries were wire-injured as described in the Methods. Animals (n=4/group) were treated the following day for 14 days with either vehicle or compound 6 (100 mg/kg, po, qd). The carotid artery was excised on day 14, sectioned, and visualized with hematoxylin and eosin staining (FIG. 11B) Intimal/medial ratios were measured for mice treated with vehicle and compound 6, *p<0.001. (FIG. 11C) The corresponding percent stenosis (reflecting luminal narrowing) was calculated as described herein, *p<0.01. Error bars are reported as ±SEM. (FIG. 11D) PDGFRβ autophosphorylation in the injured arteries was measured on day 14, 4 h post-dose.

(FIG. 12A) Images of local lymph node lymphangiogenesis model between saline and VEGF-C matrigel. (FIG. 12B) Compound 6 clearly showed inhibition of lymphangiogenesis.

FIG. 13A-C demonstrate the growth inhibitory properties of exemplary compounds on tumor cells. (FIG. 13A) Compound 6 was profiled in the NCI60 panel by the NCI Developmental Therapeutics Program and demonstrated an average growth inhibitory concentration (GI50) of 490 nM with potent growth inhibition across the entire panel of cell lines. Additionally, compounds 6, 35, or 37 (FIG. 13B) were compared to sorafenib, PLX 4720 or L779,450 (FIG. 13C) in a cell proliferation assay.

(FIG. 15A) Microscopic analysis of tumor cells exposed to compound 6 revealed that the cells appeared rounded and arrested in mitosis, whereas cells treated with sorafenib maintained their adhesive properties with evidence of intact mitotic function. Brightfield images of XPA-1 cells treated for 20 hours with PD0325901, compound 3, sorafenib, or compound 6 at 5 μM or paclitaxel at 200 nM. (FIG. 15B) Compound 3, sorafenib, and the MEK inhibitor (PD0325901) do not demonstrate this effect and the cells appear similar to DMSO treated control. Scale bar, 20 μm.

FIG. 18A-C demonstrate that exemplary compound 6 inhibits phosphorylation of S338 in breast cancer, which correlates with breast cancer tumor growth suppression. In FIG. 18A, the MDA-MB-231 tumors were treated for three consecutive days, and the tumors were resected 1 h following the final vehicle or compound 6 dose and stained for phosphorylation on CRAF S338. FIG. 18B displays the tumor growth profile after treatment with compound 6 or vehicle. FIG. 18C shows the pS338 CRAF levels in the MDA-MB231 cells in vitro. The cells were treated with DMSO (Ctrl), compound 6, or sorafenib at 5 μM for 6 h and cell lysates were resolved on 10% SDS-PAGE and immunoblotting was performed with the following antibodies: pS338 CRAF (Cell Signaling), CRAF (BD Pharmingen), and Actin (Sigma), all diluted 1:1000.

FIG. 19A-C demonstrate high potency of exemplary compounds 6 and 31-37 in cell viability assays against tumor cells A549 (FIG. 19A), T47D (FIG. 19B), and MDA-MB231 (FIG. 19C).

DETAILED DESCRIPTION OF THE INVENTION

Figure 1:
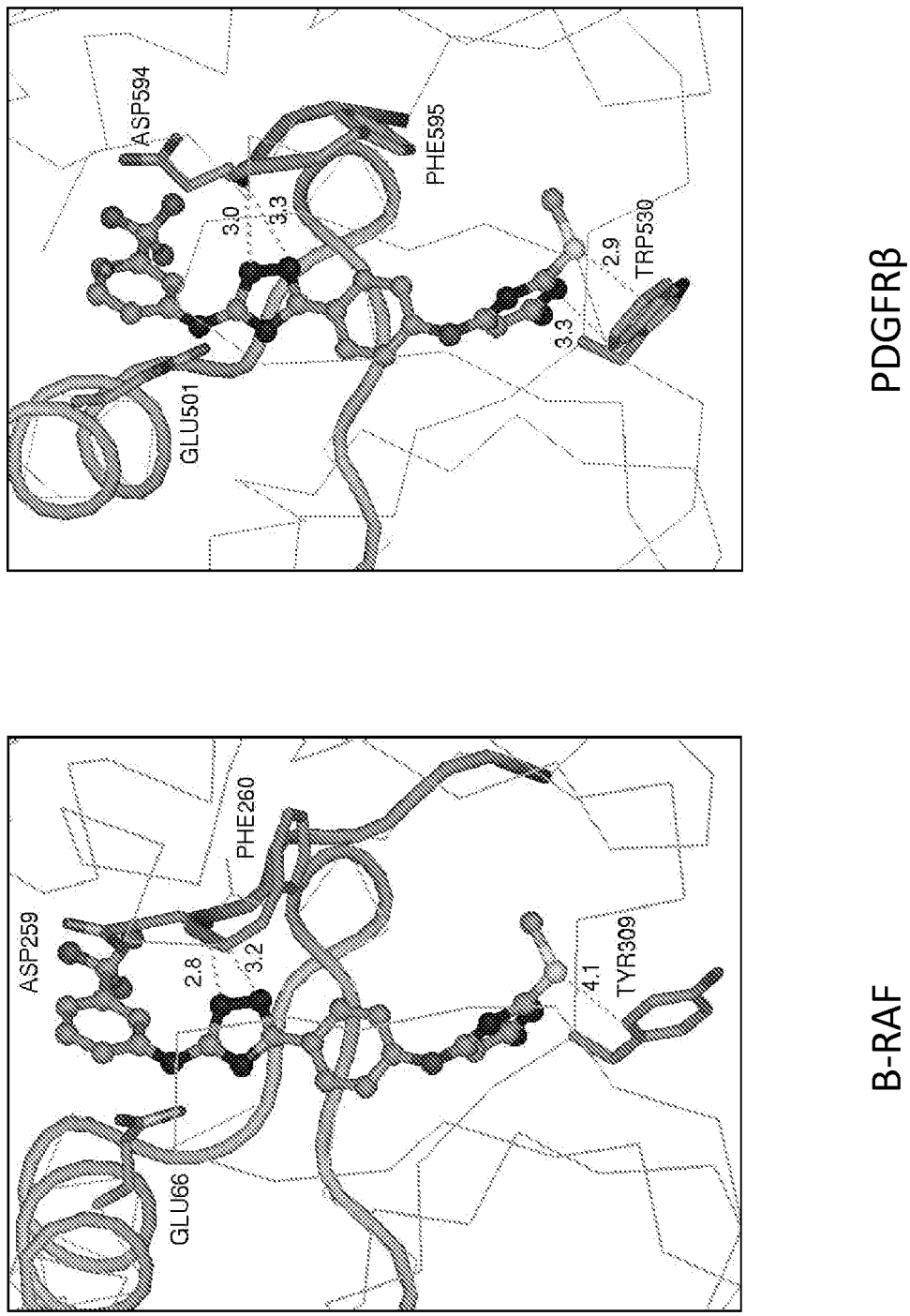
FIG. 1A-1F illustrate molecular modeling and assay screening to compounds for dual targeting of PDGFRβ and RAF.

RAF kinase is an important convergent point downstream of FGFR and VEGFR2 signaling in endothelial cells and plays a critical role in endothelial cell survival during angiogenesis. The stromal compartment is a major contributor to angiogenesis and tumor growth. This includes pericytes associated with the newly forming endothelium, which stabilize the vasculature and promote vascularization. PDGFRβ is a receptor tyrosine kinase (RTK) that is essential for promoting proper pericyte function, which stabilizes blood vessels and enables vessel maturation. PDGFRβ signaling potentiates pericyte recruitment to newly forming vessels and the secretion of pro-angiogenic molecules such as VEGFA, FGF2, and Ang1 in the local microenvironment. This promotes vessel stabilization and remodeling of the immature vascular network to a highly ordered network. Maintenance of the vascular compartment is dependent upon paracrine loops such as the secretion of PDGF-BB and FGF2, which lead to increased expression of FGFR1 on VSMCs and PDGFRα/β on ECs, respectively. Therefore, the homeostasis of the mural and vascular compartments is critical for efficient angiogenesis.

Thus inhibiting these two compartments simultaneously would initiate a potent inhibition of angiogenesis. While broad-spectrum receptor tyrosine kinase inhibitors are available, the goal was to design compounds with a narrow kinase profile to selectively inhibit relevant pathways involved in neovascularization. RAF kinase was targeted since this kinase is a downstream of multiple RTKs and is required for EC proliferation and survival, and PDGFRβ is a critical for pericyte recruitment and vessel maturation.

Due to the hydrophobic interactions and specific hydrogen bonding required for type II inhibition, the allosteric site adjacent to the kinase active site may be utilized to improve specificity over the type I Inhibitors that interact solely with the active kinase conformation in the highly conserved hinge region. Imatinib (1) and sorafenib (2) were co-crystallized with their respective targets, B-RAF and Abl kinase domains, and shown to interact in part with the allosteric site in the "DFG-out" conformation—referred to as "type II" inhibition. Based on the binding mode of imatinib (1) and sorafenib (2), compounds of an amino-triazole scaffold designed to target the allosteric site of both PDGFRβ and B-RAF using a combination of in silico screening and in vitro bioassays were prepared.

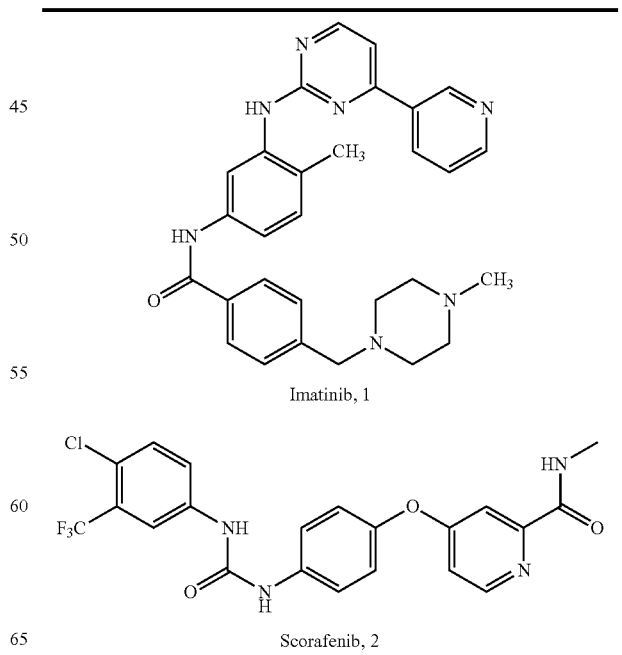

Imatinib, 1

Scorafenib, 2

-continued

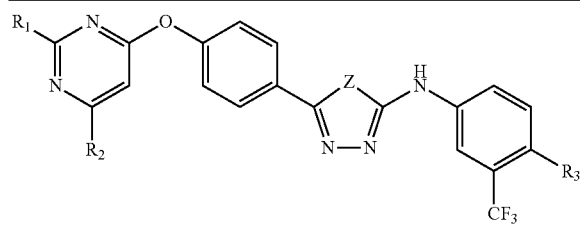

| Compound | R₁ | R₂ | R₃ | Z |
|---|---|---|---|---|
| 3 | H | NH₂ | H | NH |
| 4 | NH₂ | NH₂ | H | NH |
| 5 | NH₂ | NH₂ | Cl | NH |
| 6 | MeS | NH₂ | H | NH |
| 7 | MeS | H | H | NH |
| 8 | MeS | NH₂ | Cl | NH |
| 9 | NH₂ | MeO | H | NH |
| 10 | NH₂ | NH₂ | H | O |
| 11 | MeS | NH₂ | H | O |
| 13 | MeS | H | Cl | NH |
| 14 | MeS(O)₂ | NH₂ | H | NH |
| 15 | SEt | NH₂ | H | NH |
| 16 | S-tert-Bu | NH₂ | H | NH |
| 17 | NH₂ | S-tert-Bu | Cl | NH |
| 18 | MeS | H | Br | O |
| 19 | NH₂ | SMe | F | NH |
| 20 | NH₂ | SEt | I | NH |
| 21 | Et | NH₂ | Cl | NH |
| 22 | CF₃S | H | Cl | NH |
| 23 | NH₂ | CF₃S | H | NH |
| 24 | CF₃S | NH2 | H | NH |
| 25 | CF₃S | NH2 | Cl | NH |
| 26 | CF₃S | H | H | NH |
| 27 | NH₂ | MeO | Cl | NH |
| 28 | H | NH₂ | Cl | NH |
| 29 | NH₂ | H | H | NH |
| 30 | MeO | NH2 | H | NH |

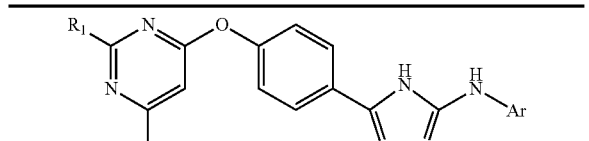

| Compound | R₁ | R₂ | Ar | Z' |
|---|---|---|---|---|
| 31 | SMe | NH₂ | 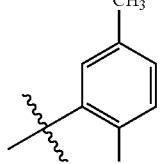 | N |
| 32 | EtO | NH₂ | 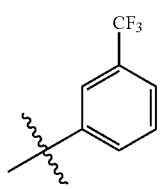 [SMILES: *c1cccc(C(F)(F)F)c1] | N |

-continued

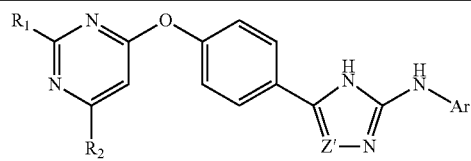

| Compound | R₁ | R₂ | Ar | Z' |
|---|---|---|---|---|
| 33 | MeS | NH₂ | 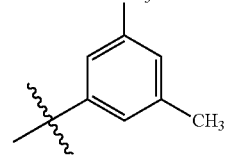 | N |
| 34 | MeS | NH₂ | 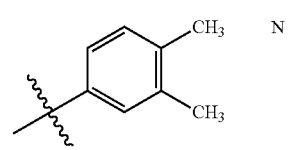 | N |
| 35 | MeS | NH₂ | 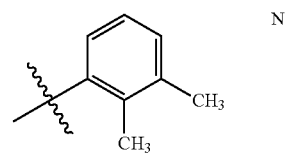 | N |
| 36 | MeS | NH2 | 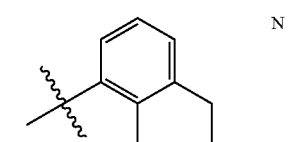 | N |
| 37 | MeS | NH₂ | 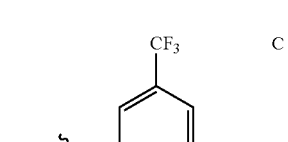 | C |

Among them, compound 6, would have been disregarded using traditional in vitro ATP-dependent kinase assays; at 10 μM, compound 6 did not inhibit any of its targets in this screening format (data not shown). For PDGFRβ, the cellular IC50 and biochemical Kd matched quite well as both were approximately 500 nM (FIG. 1B and Table 3), demonstrating a significant difference between the activity of compound 6 in cell-based vs. activated kinase assays. This is not surprising since the recombinant enzymes are not subject to the same conformational inactivation as the intact cell-associated enzymes. Although compound 6 is predicted to stabilize the inactive conformation of PDGFRβ or B-RAF, it might not be expected to suppress the activity of a recombinant activated form of this enzyme in vitro that is not subject to negative regulation. Similarly, imatinib, is 200-fold more active against the Abl kinase domain when the activation loop is unphosphorylated.

Figure 3A:
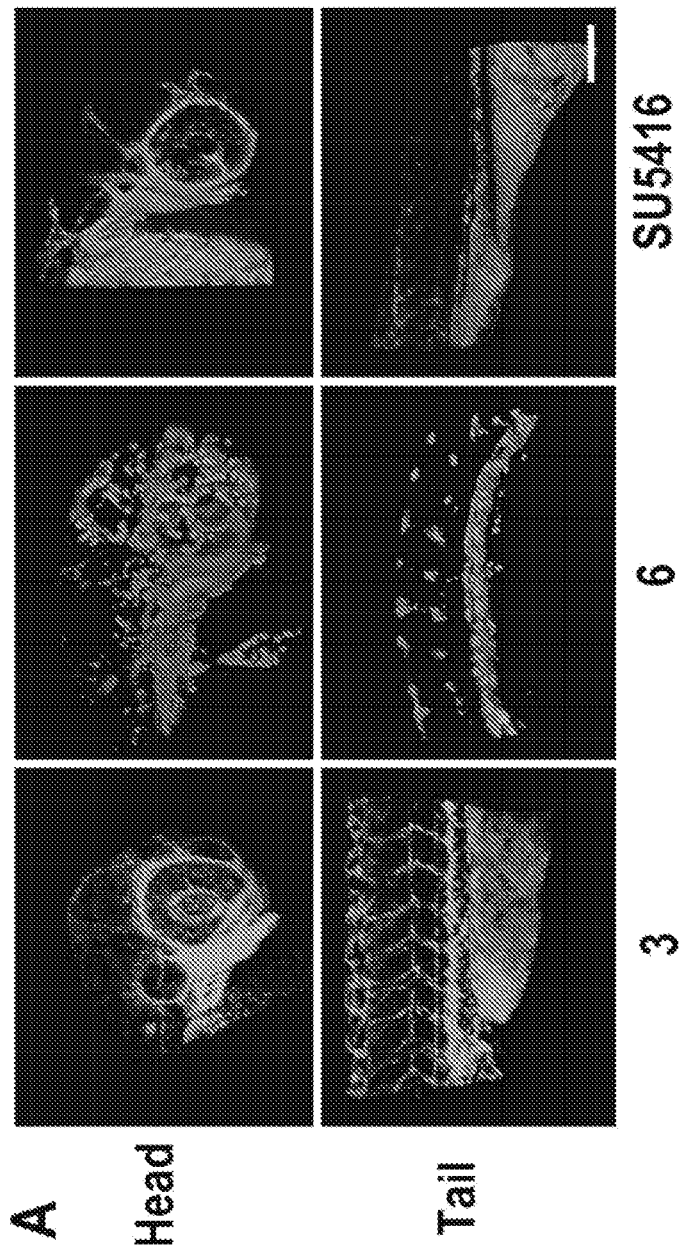
FIG. 3A-3D illustrate the effect of compound 6 regarding angiogenesis in the zebrafish.
Figure 3B:
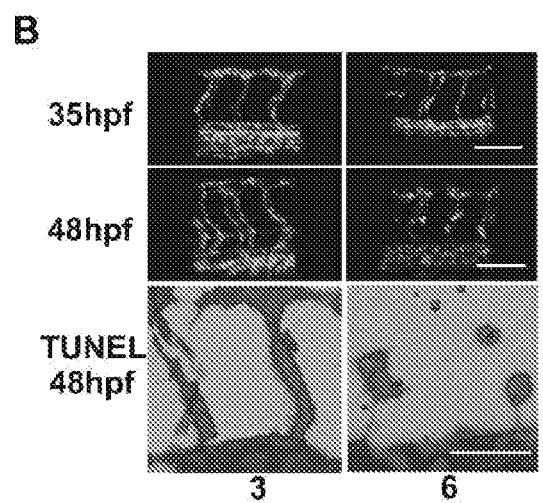

Among these compounds, compound 6 does not inhibit activated kinases in vitro and possesses dual inhibition of PDGFRβ/RAF activity that produces a potent anti-angiogenic effect which is not seen with the inhibition of either target alone. Combination of separate inhibitors of PDGFRβ and RAF reproduces the anti-angiogenic effects of compound 6 in both the zebrafish in vivo and a pericyte/endothelial cell tube formation assay in vitro, and further validates the dual targeting of PDGFRβ and RAF as a synergistic approach. Additionally, compound 6 suppresses tumor growth in orthotopic tumor models of pancreatic and renal cell carcinoma. While compound 6 inhibited cellular PDGFR and RAF, it also disrupted Flt3 and KIT (Table 3). However, Flt3 and KIT are not essential to the biological activity of compound 6 since compound 3, which blocks Flt3, Kit, and PDGFR but does not inhibit RAF, failed to disrupt vessel formation (FIG. 3A-B). This result further supports the synergy of inhibiting both PDGFR and RAF for increased anti-angiogenic activity as observed in FIG. 4 using completely different chemotypes.

Similarly, the allosteric site adjacent to the kinase active site in pseudokinases (e.g., HER3, EphB6, CCK4, KSR, Trb3, GCN2, TRRAP, LIK and CASK), proteins having a kinase-like domain, may be utilized to modulate diverse cellular processes of the pseudokinases.

In accordance with the present invention, the development of selective inhibitors directed against PDGFRβ and RAF (e.g. A-RAF, B-RAF and C-RAF), and define a synergistic combination which leads to effective inhibition of angiogenesis and tumor growth are discovered. Although new clinically approved kinase inhibitors work through broad-spectrum inhibition and opportune target combinations, invention methods are provided to narrow the kinase profile to selective combinations which provide great synergy. This approach will ultimately increase the therapeutic window of these agents and improve the chance of providing therapeutic efficacy with minimal side effects.

Process of Preparing Exemplary Compounds

The exemplary compounds described herein, in some instances, are prepared according to the known procedures or the novlel procedures disclosed herein.

In some embodiments, there are provided processes for preparing a triazole compound of formula I:

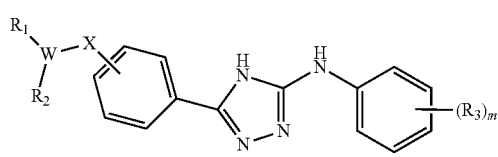

(I)

comprising reacting a compound of formula II,

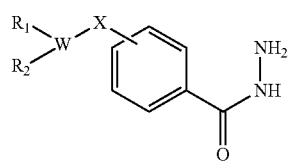

(II)

with a compound of formula (III),

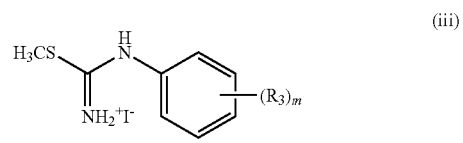

(iii)

in the presence of a base, wherein W is selected from the group consisting of pyridine, pyridazine, pyrimidine, pyrazine, triazine, quinoline, isoquinoline, cinnoline, quinazoline, quinoxaline, 1,2,4-benzotriazine and azaindole; X is O, S or NH; $R_1$ and $R_2$ are independently a hydrogen, optional substituted alkyl, halogen, optional substituted amine, —$NH_2$, —OH, optional substituted alkoxy, optional substituted thioalkyl, —$SCF_3$, optional substituted alkylsulfinyl or an optional substituted alkylsulfonyl; $R_3$ is independently a hydrogen, halogen substituted $C_{1-6}$ alkyl, or halogen substituted $C_{1-6}$ alkoxy, or, optionally, two $R_3$ are joined to form a 5 to 7 membered carbocycle; and m is 1-5. (See scheme 1)

Scheme 1. Triazole formation reaction

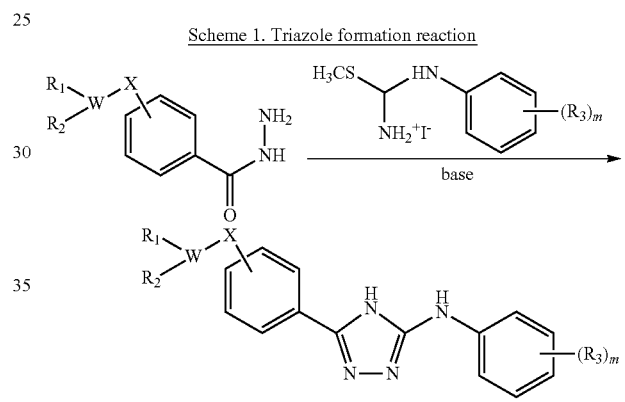

In one embodiment, the triazole formation is achieved with good yield under suitable solvent with a base, preferable an amine base; more preferable a 2,6-lutidine. In certain embodiments, the molar ratio of the compound of formula II to the compound of formula III is in the range from 0.6:1 to 0.9:1.

The triazole formation provided herein is applicable to many hydrazide precursors. For example, the reaction is applicable where W is pyridine, pyridazine, pyrimidine, pyrazine, triazine, quinoline, isoquinoline, cinnoline, quinazoline, quinoxaline, 1,2,4-benzotriazine, azaindole, or the like. The linkage between W and the phenyl ring can be an ether, thioether or amine linkage. The S-methylthiourea of formula (III) is prepared in situ from its thiourea precursor upon methylation (e.g. MeI). When suitable solvent (determined by the solubility of the hydrazide precursors and the in situ S-methylthiourea) and base are used, good yield with satisfactory purity can be achieved. The triazole compounds can then go to next step directly (e.g. salts preparation) without time-consuming and/or labor-intensive column chromatography.

For example, without limitation, a skilled artisan may use the following hydrazide precursors.

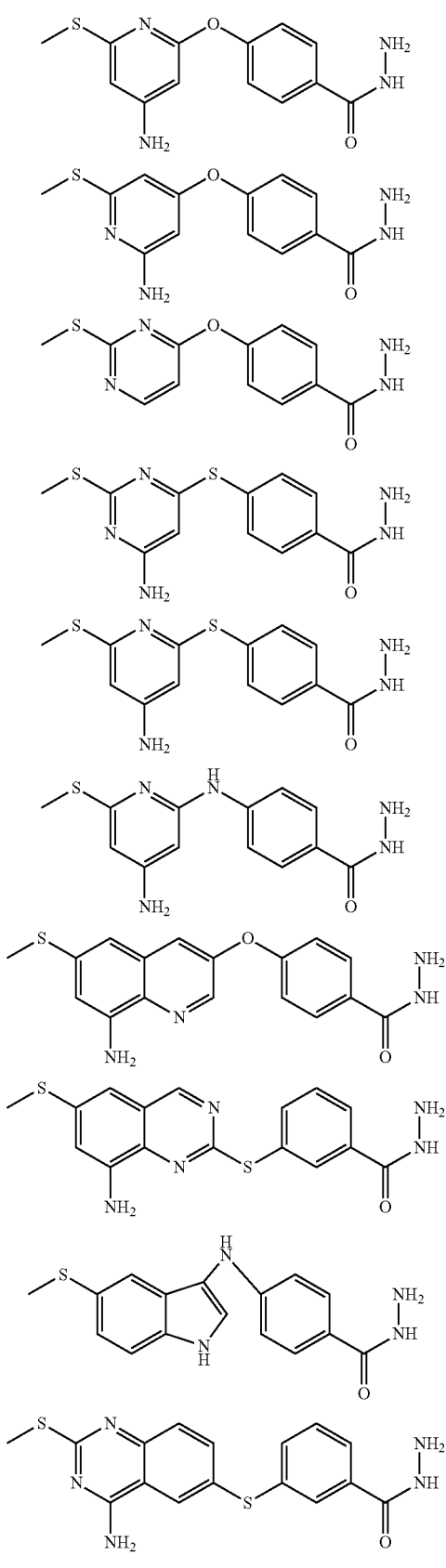

In some embodiments, a compound of formula I, preferably of formula Ia,

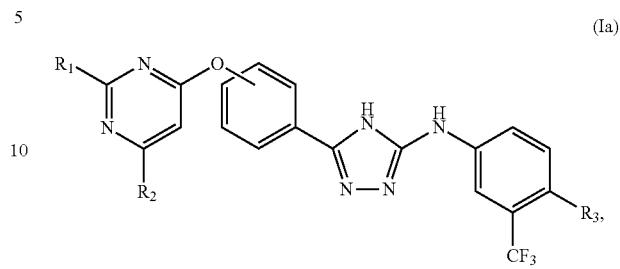

can be prepared from reacting a compound of formula IIa,

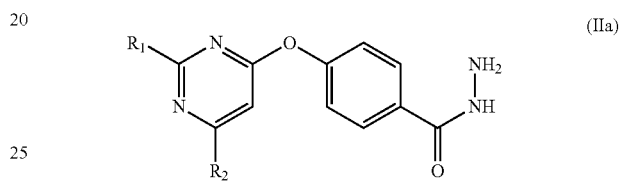

with a compound of formula (IIIa),

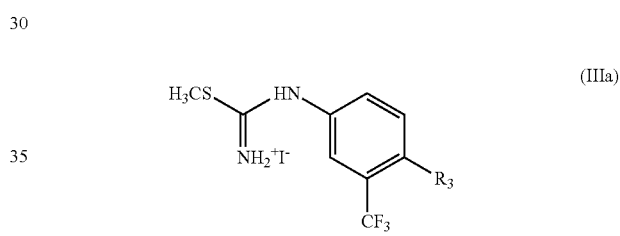

in the presence of a base (Scheme 2), wherein $R_1$ and $R_2$ are independently a hydrogen, optional substituted alkyl, halogen, optional substituted amine, —$NH_2$, —OH, optional substituted alkoxy, optional substituted thioalkyl, —$SCF_3$, optional substituted alkylsulfinyl or an optional substituted alkylsulfonyl and $R_3$ is a hydrogen, halogen substituted $C_{1-6}$ alkyl, or halogen substituted $C_{1-6}$ alkoxy. In certain embodiments, the molar ratio of the compound of formula IIa to the compound of formula IIIa is in the range from 0.6:1 to 0.9:1. The processes have been optimized to provide compounds of formula (Ia) with satisfactory purity and thus require little or no chromatographic purification. In general, after the processes, the crude is ready for next step, e.g., to prepare its salts.

Scheme 2. Triazole formation from pyrimidine hydrazide precursors.

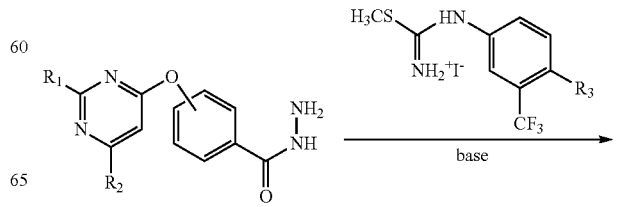

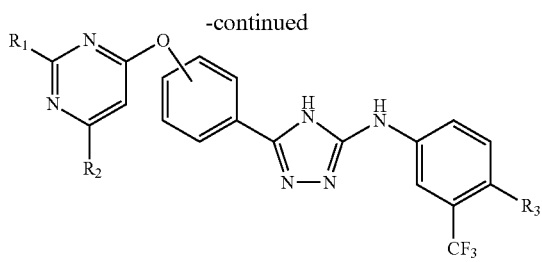

In some embodiments, a compound of formula I, preferably of formula Ib,

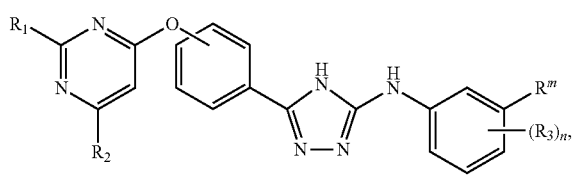

can be prepared from reacting a compound of formula IIa,

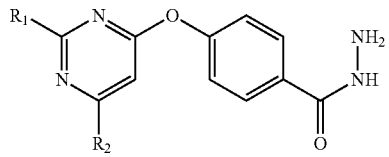

with a compound of formula (IIIb),

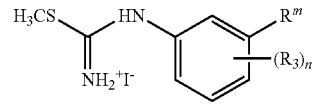

in the presence of a base, wherein $R_1$ and $R_2$ are independently a hydrogen, optional substituted alkyl, halogen, optional substituted amine, —$NH_2$, —OH, optional substituted alkoxy, optional substituted thioalkyl, —$SCF_3$, optional substituted alkylsulfinyl or an optional substituted alkylsulfonyl; $R^m$ is $C_{1-6}$ alkyl, or halogen substituted $C_{1-6}$ alkyl; $R_3$ is independently a hydrogen, $C_{1-6}$ alkyl, halogen substituted $C_{1-6}$ alkyl, halogen substituted $C_{1-6}$ alkoxy, or $C_{3-10}$ cycloalkyl; or, optionally, $R^m$ and $R_3$ are joined to form a five to seven membered carbocycle; and n is 0-4. In certain embodiments, the molar ratio of the compound of formula IIa to the compound of formula IIIb is in the range from 0.6:1 to 0.9:1. The processes have been optimized to provide compounds of formula (Ib) with satisfactory purity and thus require little or no chromatographic purification. In general, after the processes, the crude is ready for next step, e.g., to prepare its salts.

Nature of the base was found to be important to maximize the yield. In some embodiments, the base used for the processes is an amine base, preferably a 2,6-lutidine.

It is also determined that the choice of solvent would affect the purity and the yield of the triazole formation. In some embodiments, the solvent used for the processes of triazole formation herein is acetonitrile, DMF, N-methyl-pyrrolid-2-one (NMP), $^tBuOH$ or $^iPrOH$.

In other embodiments, there are provided processes of preparing compounds of formula (I), (Ia) or (Ib) wherein $R_1$ is a hydrogen, —$NH_2$, optional substituted alkoxy, optional substituted thioalkyl, —$SCF_3$, optional substituted alkylsulfinyl or an optional substituted alkylsulfonyl. For example, $R_1$ may be —H, —$NH_2$, —OMe, —OEt, —SMe, —SEt, —$S^tBu$, —$SO_2Me$, —$SCF_3$, or the like.

In other embodiments, there are provided processes of preparing compounds of formula (I), (Ia) or (Ib) wherein $R_2$ is a hydrogen, $NH_2$, or an optional substituted alkoxy. For example, $R_2$ may be —H, —$NH_2$, —NHMe, —OMe, —OEt, —$OCF_3$, or the like.

In other embodiments, there are provided processes of preparing compounds of formula (I), (Ia) or (Ib) wherein $R_1$ and $R_2$ are independently an optional substituted amine. For example, $R_1$ and/or $R_2$ may be —$NH_2$, —NHMe, or the like.

In other embodiments, there are provided processes of preparing compounds of formula (I), (Ia) or (Ib) wherein $R_1$ is an optional substituted thioalkyl and $R_2$ is an optional substituted amine. For example, $R_1$ may be —SMe, —SEt, —$S^tBu$, —$SCF_3$, or the like and $R_2$ may be —$NH_2$, —NHMe, or the like. In certain embodiments, $R_1$ is a MeS and $R_2$ is a $NH_2$.

In the case of 1,2,4-triazoles, there exist three tautomeric structures, as shown below:

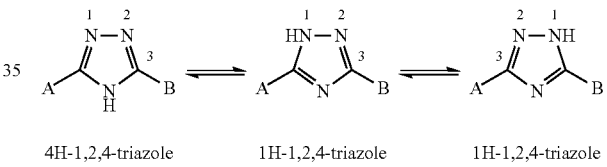

Which tautomeric structure is prevailing depends on the substituents on the triazole moiety and on the reaction conditions. As known to those having ordinary skill in the art, typically, 1H-1,2,4-triazole is the most common tautomeric form, especially if an amino substituent is attached to the ring. Even though all three tautomeric structures can be present, all the generic structures and all the examples having 1,2,4-triazole moiety are shown herein in one tautomeric form, such as 4H-1,2,4-triazole, for simplicity and for the comparison with its direct analogues, such as examples containing 1,3,4-oxadiazole moiety. Using only 4H-tautomeric form to draw the structures for the sake of simplicity, does not imply that the triazole compounds provided herein exist in that particular tautomeric form.

In according with the present invention, there are provided processes for preparing a compound of formula IV:

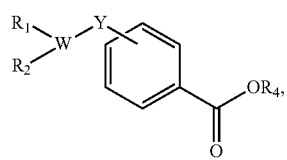

comprising reacting a compound of formula V,

with a compound of formula (VI),

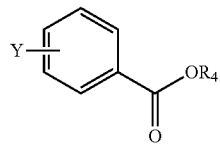

in the presence of a base wherein L is a leaving group e.g., a chloride, tosylate or other suitable leaving group; Y is —SH, —OH, or —NH$_2$; R$_1$ and R$_2$ are independently hydrogen, optional substituted alkyl, halogen, optional substituted protected amine, optional substituted alkoxy, optional substituted thioalkyl, CF$_3$S, optional substituted alkylsulfinyl or optional substituted alkylsulfonyl and R$_4$ is a C$_{1-6}$ alkyl. A compound of formula IV is then converted to a hydrazide suitable for triazole formation (Scheme 3).

Scheme 3 Preparation of hydrazide precursors

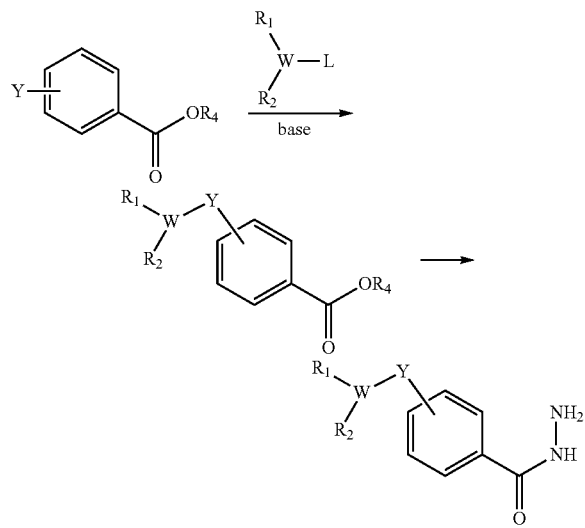

In certain embodiments, the compound of formula IV is a compound having the structure of formula IVa:

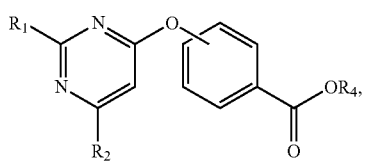

and the compound of formula V is a compound having the structure of Va,

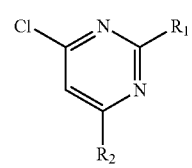

and the compound of formula VI is an alkyl hydroxybenzoate. The processes for preparing a compound of formula IV provided herein are under very mild conditions, e.g. at about 25-35° C. (room temperature) when R$_1$ and/or R$_2$ are a Boc protected amine. The processes have been optimized to provide compounds of formula IV or IVa with satisfactory purity and thus require little or no chromatographic purification. In general, after the processes, the crude can be used for next step.

In some embodiments, the base used for the processes of preparing compounds of formula IV or IVa is an amine base; preferably a 1,4-diazabicyclo[2.2.2]octane. In other embodiments, methyl 4-hydroxybenzoate is used in the processes.

In other embodiments, there are provided processes of preparing compounds of formula IV or IVa wherein R$_1$ is a hydrogen, optional substituted protected amine, optional substituted alkoxy, optional substituted thioalkyl, CF$_3$S, optional substituted alkylsulfinyl or an optional substituted alkylsulfonyl. For example, R$_1$ may be —H, —NH$_2$, —OMe, —OEt, —SMe, —SEt, —S$^t$Bu, —SO$_2$Me, —SCF$_3$, or the like.

In other embodiments, there are provided processes of preparing compounds of formula IV or IVa wherein R$_2$ is a hydrogen, optional substituted protected amine, or an optional substituted alkoxy. For example, R$_2$ may be —H, —NH$_2$, —NHMe, —OMe, —OEt, —OCF$_3$, or the like.

In other embodiments, there are provided processes of preparing compounds of formula IV or IVa wherein R$_1$ and R$_2$ are independently an optional substituted protected amine; preferably the optional substituted protected amine is protected by an acid labile protecting group such as Boc. For example, R$_1$ and/or R$_2$ may be —NH$_2$, —N(Boc)Me, —N(Boc)$_2$, or the like. Preferably, R$_1$ and R$_2$ are independently a —N(Boc)$_2$.

In other embodiments, there are provided processes wherein R$_1$ is an optional substituted thioalkyl and R$_2$ is an optional substituted protected amine, preferably an amine with an acid labile protecting group such as -Boc. For example, R$_1$ may be —SMe, —SEt, —S$^t$Bu, —SCF$_3$, or the like and R$_2$ may be —NH(Boc), —N(Boc)Me, N(Boc)$_2$, or the like. In some embodiments, there are provided processes of preparing compounds of formula IV or IVa wherein R$_1$ is a —SMe and R$_2$ is a —N(Boc)$_2$.

Examples of Methods of Dosing and Treatment Regimens

In one aspect, the compositions containing the compounds (i.e., allosteric kinase inhibitors described herein) are administered for prophylactic and/or therapeutic treatments. In therapeutic applications, the compositions are administered to a patient already suffering from a disease, disorder, or condition, in an amount sufficient to cure or at least partially arrest the symptoms of the disease, disorder, or condition. Amounts effective for this use will depend on the severity and course of the disease, disorder, or condition, previous therapy, the patient's health status, weight, and response to the drugs, and the judgment of the treating physician.

In prophylactic applications, compositions containing the compounds (i.e., allosteric kinase inhibitors described herein) are administered to a patient susceptible to or otherwise at risk of a particular disease, disorder or condition. Such an amount is defined to be a "prophylactically effective amount or dose." In this use, the precise amounts also depend on the patient's state of health, weight, and the like. In some embodiments, when used in a patient, effective amounts for this use depend on the severity and course of the disease, disorder or condition, previous therapy, the patient's health status and response to the drugs, and the judgment of the treating physician.

In some embodiments, the case wherein the patient's condition does not improve, upon the doctor's discretion the administration of the compounds (i.e., allosteric kinase inhibitors described herein) are administered chronically, that is, for an extended period of time, including throughout the duration of the patient's life in order to ameliorate or otherwise control or limit the symptoms of the patient's disease, disorder, or condition.

In some embodiments, wherein the patient's status does improve, upon the doctor's discretion the administration of the compounds (i.e., allosteric kinase inhibitors described herein) are given continuously; alternatively, the dose of drug being administered is temporarily reduced or temporarily suspended for a certain length of time (i.e., a "drug holiday"). In other embodiments, the length of the drug holiday varies between 2 days and 1 year, including by way of example only, about 2 days, about 3 days, about 4 days, about 5 days, about 6 days, about 7 days, about 10 days, about 12 days, about 15 days, about 20 days, about 28 days, about 35 days, about 50 days, about 70 days, about 100 days, about 120 days, about 150 days, about 180 days, about 200 days, about 250 days, about 280 days, about 300 days, about 320 days, about 350 days, or about 365 days. In further embodiments, the dose reduction during a drug holiday is from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's condition has occurred, a maintenance dose is administered if necessary. Subsequently, in other embodiments, the dosage or the frequency of administration, or both, are reduced, as a function of the symptoms, to a level at which the improved disease, disorder or condition is retained. In further embodiments, patients will, however, require intermittent treatment on a long-term basis upon any recurrence of symptoms.

In other embodiments, the amount of a given agent that corresponds to such an amount varies depending upon factors such as the particular compound, disease, disorder, or condition and its severity, the identity (e.g., weight) of the subject or host in need of treatment, but nevertheless is routinely determined in a manner according to the particular circumstances surrounding the case, including, e.g., the specific agent being administered, the route of administration, the condition being treated, and the subject or host being treated. In some embodiments, however, doses employed for adult human treatment are typically in the range of about 0.02 to about 5000 mg per day or about 1 to about 1500 mg per day. In further embodiments, the desired dose is conveniently presented in a single dose or as divided doses administered simultaneously (or over a short period of time) or at appropriate intervals, for example as two, three, four or more sub-doses per day.

In some embodiments, the pharmaceutical composition described herein are in unit dosage forms suitable for single administration of precise dosages. In unit dosage form, the formulation is divided into unit doses containing appropriate quantities of one or more compound. in other embodiments, the unit dosage is in the form of a package containing discrete quantities of the formulation. Non-limiting examples are packaged tablets or capsules, and powders in vials or ampoules. In another embodiment, aqueous suspension compositions are packaged in single-dose non-reclosable containers. In further embodiments, multiple-dose reclosable containers are used, in which case it is typical to include a preservative in the composition. By way of example only, formulations for parenteral injection are presented in unit dosage form, which include, but are not limited to ampoules, or in multi-dose containers, with an added preservative.

The daily dosages appropriate for the compounds (i.e., allosteric kinase inhibitors described herein) described herein are from about 0.01 to about 2.5 mg/kg per body weight. An indicated daily dosage in the larger mammal, including, but not limited to, humans, is in the range from about 0.5 mg to about 100 mg, conveniently administered in divided doses, including, but not limited to, up to four times a day or in extended release form. Suitable unit dosage forms for oral administration include from about 1 to about 50 mg active ingredient. The foregoing ranges are merely suggestive, as the number of variables in regard to an individual treatment regime is large, and considerable excursions from these recommended values are not uncommon. In further embodiments, such dosages are altered depending on a number of variables, not limited to the activity of the compound used, the disease, disorder, or condition to be treated, the mode of administration, the requirements of the individual subject, the severity of the disease, disorder, or condition being treated, and the judgment of the practitioner.

In yet further embodiments, toxicity and therapeutic efficacy of such therapeutic regimens are determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and in some embodiments is expressed as the ratio between $LD_{50}$ and $ED_{50}$. In other embodiments, the data obtained from cell culture assays and animal studies is used in formulating a range of dosage for use in human. In some embodiments, the dosage of such compounds lies within a range of circulating concentrations that include the $ED_{50}$ with minimal toxicity. In yet further embodiments, the dosage varies within this range depending upon the dosage form employed and the route of administration utilized.

Lymphangiogenesis, Angiogenesis and/or Growth of a Tumor

Provided herein are methods for inhibiting or preventing lymphangiogenesis, angiogenesis and/or growth of a tumor, which comprises contacting the tumor with a compound that (i) stabilizes a protein kinase in the inactive state and (ii) is not an ATP competitive inhibitor of the protein kinase in the active state. In some embodiments, the compound for the methods is a selective type II inhibitor; preferably a selective type II inhibitor of RAF kinase (e.g. B-RAF kinase); more preferably the compound is also a selective type II inhibitor of a PDGF receptor. In some embodiments, the compound for the methods modulates A-RAF. In other embodiments, the compound for the methods inhibits the heterodimerization of BRAF with CRAF. In some embodiments, the compound inhibits the phosphorylation of S338 of C-RAF. In another embodiment, the compound does not inhibit active kinases selected from the group B-RAF, C-RAF, VEGFR1, VEGFR2, Flt3, Kit, and PDGFRβ. In some embodiments, the compound is an allosteric inhibitor of PDGFRα, PDGFRβ, Flt3 and/or c-Kit. In some embodiments, the compound has the structure

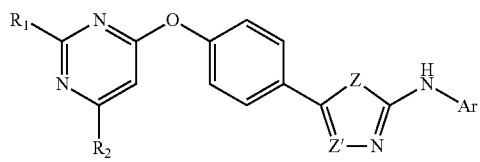

wherein $R_1$ and $R_2$ are independently hydrogen, optional substituted alkyl, halogen, optional substituted amine, $NH_2$, optional substituted alkyoxy, optional substituted thioalkyl, $CF_3S$, optional substituted alkylsulfinyl or optional substituted alkylsulfonyl; Z is NH, S or O; Z' is N or C; and Ar is phenyl or bicyclic phenyl optionally substituted with one or more substituents selected from $C_{1-6}$ alkyl, halogen substituted $C_{1-6}$ alkyl, halogen substituted $C_{1-6}$ alkoxy, and $C_{3-10}$ cycloalkyl. In certain embodiments, the compound has the structure

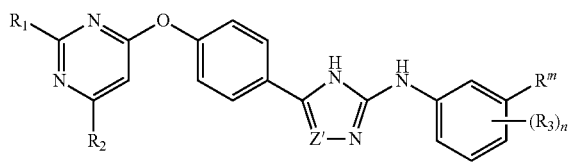

wherein $R^m$ is $C_{1-6}$ alkyl, or halogen substituted $C_{1-6}$ alkyl; and $R_3$ is independently a hydrogen, $C_{1-6}$ alkyl, halogen substituted $C_{1-6}$ alkyl, halogen substituted $C_{1-6}$ alkoxy, or $C_{3-10}$ cycloalkyl; or, optionally, $R^m$ and $R_3$ are joined to form a five to seven membered carbocycle; and n is 0-4. In certain embodiments, the compound has the structure

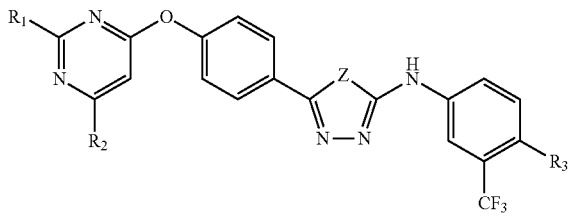

wherein $R_3$ is hydrogen or halogen; and Z is NH, S or O. In another embodiment, the compound is selected from

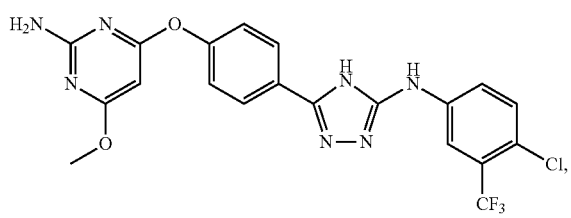

-continued

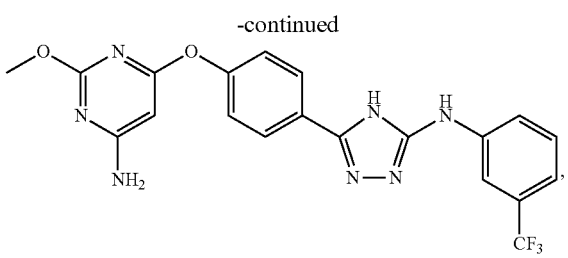

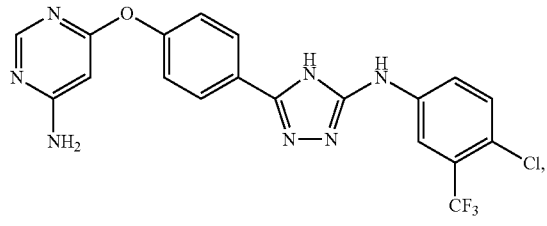

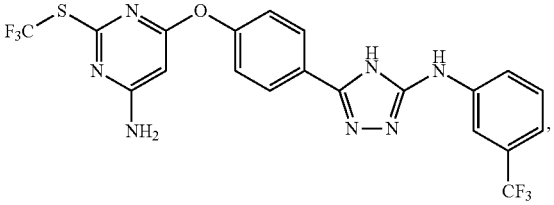

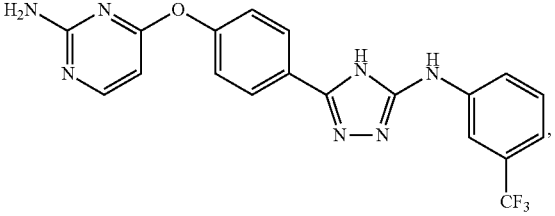

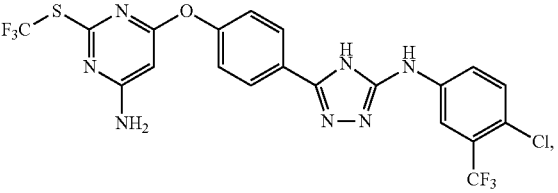

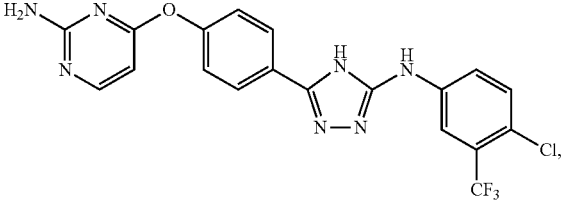

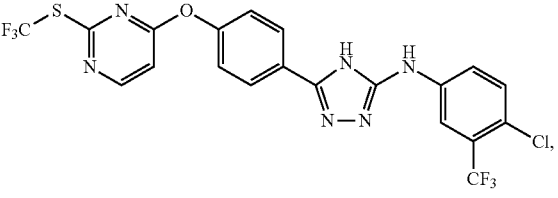

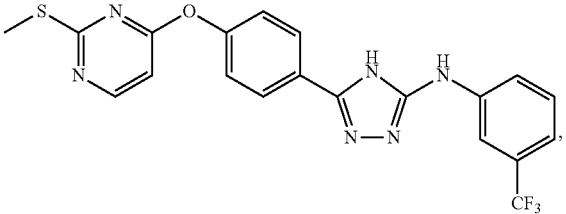

-continued
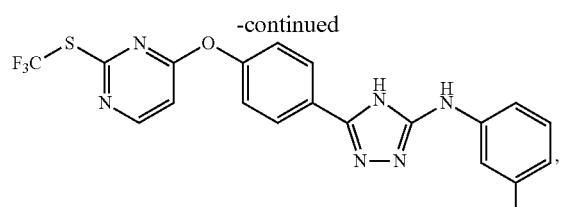
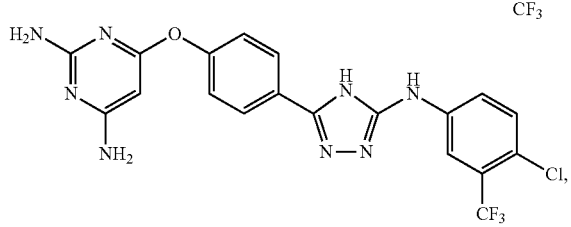
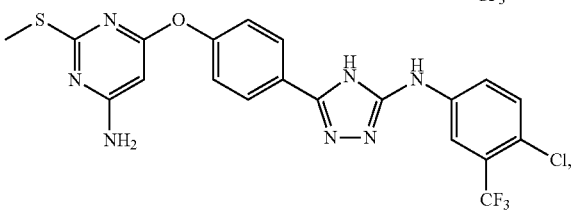
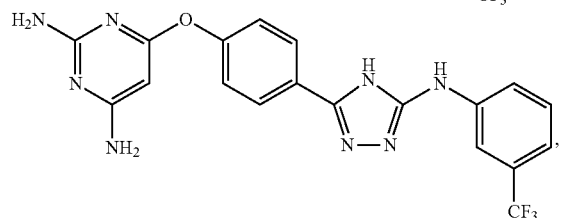
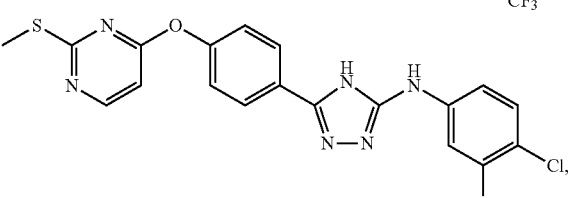
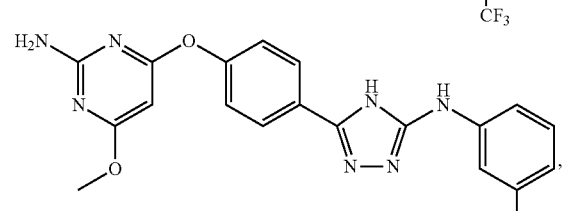
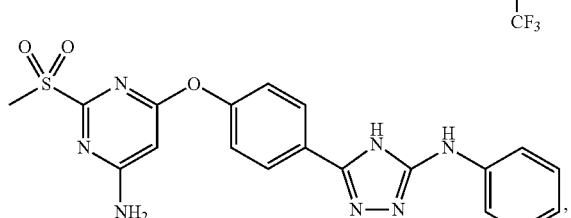
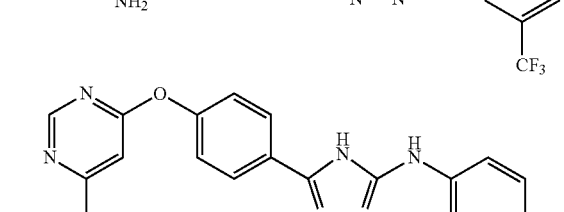
-continued
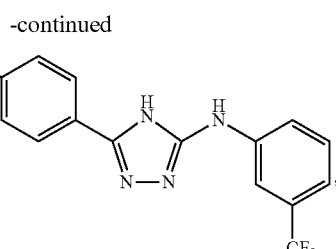
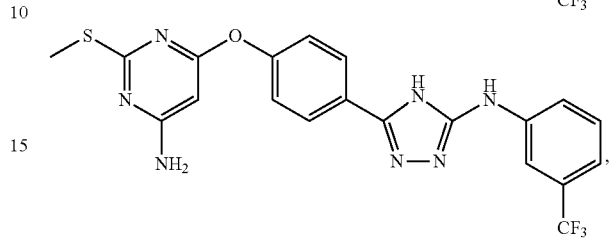
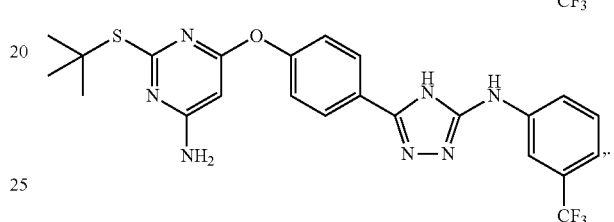
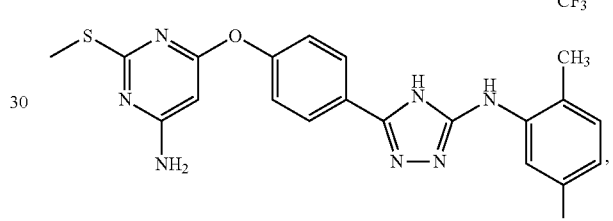
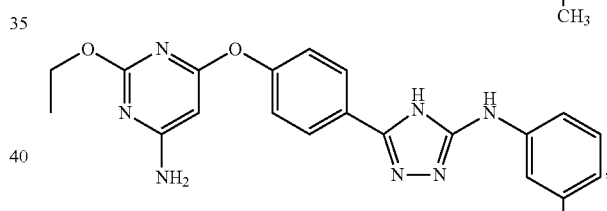
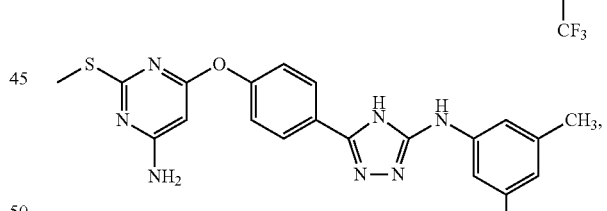
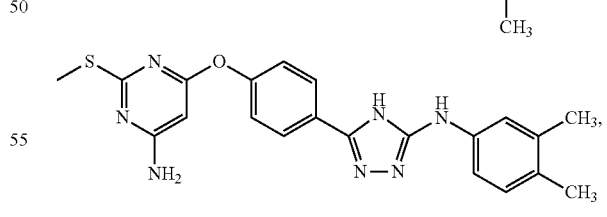
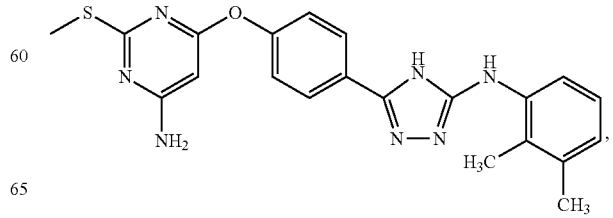

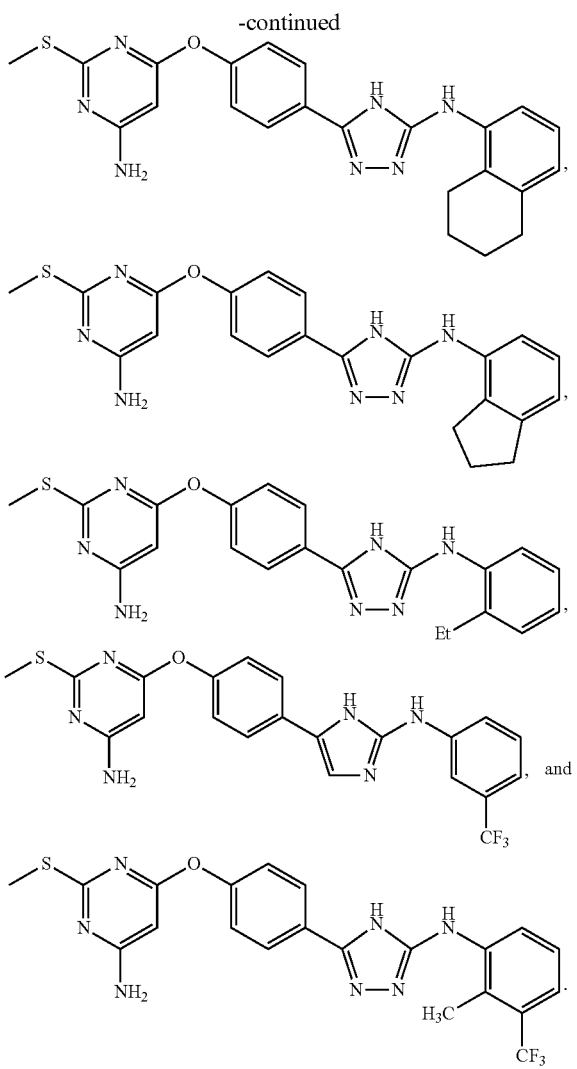

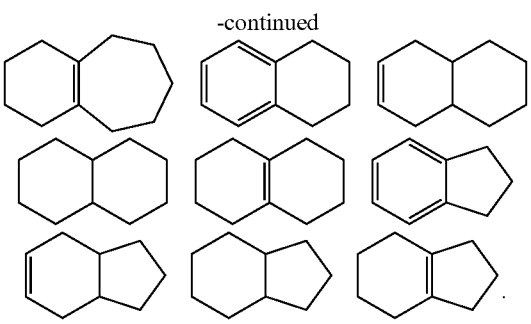

The term "alkyl" as used herein, means a straight, branched chain, or cyclic (in this case, it would also be known as "cycloalkyl") hydrocarbon containing from 1-10 carbon atoms. Illustrative examples of alkyl include, but are not limited to, methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, and n-decyl.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e a heteroatom). Heterocycle includes heteroaryl and heterocycloalkyl. Carbocycles and heterocycles can be optionally substituted. The following illustrates a few exeamplary carbocycles

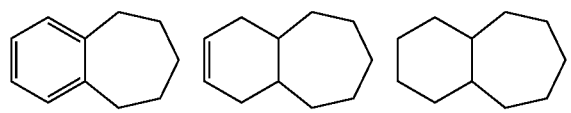

The term "optionally substituted" as defined herein, means the referenced group is substituted with zero, one or more substituents as defined herein.

As used herein, the term "sulfinyl" refers to a —S(=O)—R, where R is selected from the group consisting of alkyl, cycloalkyl, aryl, heteroaryl (bonded through a ring carbon) and heterocycloalkyl (bonded through a ring carbon).

As used herein, the term "sulfonyl" refers to a —S(=O)$_2$—R, where R is selected from the group consisting of alkyl, cycloalkyl, aryl, heteroaryl (bonded through a ring carbon) and heterocycloalkyl (bonded through a ring carbon).

The lymphatic vascular system plays an important role in the maintenance of tissue fluid homeostasis, in the afferent phase of the immune response, and in the metastatic spread of cancers. Vascular endothelial growth factor-C (VEGF-C) and VEGF-D are secreted glycoproteins that activate VEGF receptor-2 (VEGFR-2) and VEGFR-3 (Achen et al., (1998) *Proc. Natl. Acad. Sci. USA* 95: 548-553; Joukov et al., (1996) *EMBO J.* 15: 290-298)—cell surface receptor tyrosine kinases that are expressed predominantly on blood vascular and lymphatic endothelia respectively (for review see Stacker et al., *FASEB J.* 16: 922-934, 2002). VEGFR-3 signals for lymphangiogenesis (Veikkola, et al., (2001) *EMBO J.* 20: 1223-1231) whereas VEGFR-2 is thought to signal for angiogenesis. Human VEGF-C and VEGF-D stimulate both angiogenesis and lymphangiogenesis in vivo (See e.g. Byzova et al., (2002) *Blood* 99: 4434-4442; Veikkola et al., (2001) *EMBO J.* 20: 1223-1231; Marconcini et al., (1999) *Proc. Natl. Acad. Sci. USA* 96: 9671-9676).

There is increasing evidence that lymphatic vessels also actively participate in acute and chronic inflammation. Lymphangiogenesis has also been observed in experimental models of chronic airway inflammation. UVB irradiation of the skin also results in enhanced expression of vascular endothelial growth factor (VEGF)-A, and systemic blockade of VEGF-A led to diminished UVB-induced lymphatic vessel abnormalities and skin inflammation in mice, indicating that VEGF-A-mediated impairment of lymphatic vessel function promotes edema formation and inflammation. Accordingly, selective type II inhibitor of protein kinase (e.g. B-RAF kinase) stabilizing a protein kinase in the inactive state with a compound that is not ATP competitive inhibitors of the protein kinase in the active state, can be used to block the activation of VEGF-C and VEGF-D and thereby inhibit angiogenesis, lymphangiogenesis and other biological effects induced by partially processed or fully processed VEGF-C or VEGF.

Pseudokinase

In some embodiments, the methods described here for treating cancer in a human subject comprising administering to a patient in need a compound that binds a pseudokinase. In certain embodiments, the pseudokinase is a kinase suppressor of Ras (KSR).

Several structural and sequence homology studies of protein kinase domains have revealed a consensus of what are the common motifs that are required for catalytic activity. In some instances, these comprise residues that are required for nucleotide (ATP) binding, metal ion (Mg2+) binding and residues required for phosphoryl group transfer. There are 518 known human protein kinases, representing the third most common functional domain. Interestingly, about 10% of the kinome appear to lack at least one of the motifs required for catalysis and have been termed pseudokinases.

Several studies show that mutations affecting pseudokinase domains underlie the dysregulation of catalytic activity of several clinically-important kinases, including LKB1, Raf and Jak2, by their partner pseudokinase regulators, STRAD, KSR and the Jak2 JH2 domain, respectively. These studies provide a link between pseudokiase-mediated dysregulation of signal transduction and a number of diseases including cancers and blood cell malignancies. Exemplary pseudokinases are provided herein.

STRADα

The Step 20 related adaptor (STRADα and STRAβ) isoforms are part of the LKB1 heterotrimeric tumour suppressor complex. Together with the adaptor protein MO25, STRAD activates the LKB1 kinase through an allosteric mechanism that does not require LKB1 activation loop phosphorylation. (Zeqiraj et al., Science 2009; 326(5960): 1707-1711) Despite the changes in the glycine-rich loop, (the third consensus glycine being replaced by Met83, the crystal structure of STRADα revealed that STRADα is capable of binding ATP with low nanomolar affinity, and retains a kinase fold that that is typical of the canonical 'active' kinase conformation.(Zegiraj et al., PLoS Biol 2009;7(6):e1000126) The active conformation of STRADα was shown to be modulated by its binding partner MO25, as well as ATP. Loss of ATP and MO25 binding impinges on the ability of STRAD to activate the LKB1 kinase. This suggests that the 'active' conformation of STRADα plays a key role.

ILK

Integrin-linked kinase (ILK) is a 59 kDa protein originally identified while conducting a yeast-two hybrid screen with integrin β1 as the bait protein (Hannigan et al., 1996). Since its discovery, ILK has been associated with multiple cellular functions including cell migration, cell proliferation, cell-adhesions, signal transduction. Integrin-linked kinase (ILK), interacts with the cytoplasmic domain of beta-1 integrin. This gene encodes a serine/threonine protein kinase with 4 ankyrin-like repeats, which associates with the cytoplasmic domain of beta integrins and acts as a proximal receptor kinase regulating integrin-mediated signal transduction. Multiple alternatively spliced transcript variants encoding the same protein have been found for this gene. ILK is part of a heterotrimeric complex together with PINCH and parvin (the so-called IPP complex). See e.g., Legate, et al., Nat Rev Mol Cell Biol 2006; 7(1):20-31. A recent crystal structure of ILK bound to α-Parvin has uncovered the molecular basis of ILK function and explains why ILK is incapable of phosphorylating any substrates (Fukuda et al., Mol Cell 2009; 36(5):819-830). A striking feature of the ILK-α-parvin complex structure is the presence of ATP in the ILK nucleotide binding pocket, despite several non-conservative substitutions of crucial glycine residues in the glycine-rich loop.

HER3

HER3/ErbB3 is a member of the human epidermal growth family (HER) of tyrosine kinase receptors that also includes HER1/ErbB1, HER2/ErbB2 and HER4/ErbB4. Of the four members, HER3 is classified as a pseudokinase because it lacks two of the eleven residues important for catalysis. Upon ligand binding to the EGF receptor, the intracellular kinase domains undergo homodimerisation and heterodimerisation resulting in the formation of active asymmetric dimmers. ErbB3/Her3 is an enzyme that in humans is encoded by the ERBB3 gene. This gene encodes a member of the epidermal growth factor receptor (EGFR) family of receptor tyrosine kinases. This membrane-bound protein has a neuregulin binding domain but not an active kinase domain. It therefore can bind this ligand but not convey the signal into the cell through protein phosphorylation. However, it does form heterodimers with other EGF receptor family members which do have kinase activity. Heterodimerization leads to the activation of pathways which lead to cell proliferation or differentiation. Amplification of this gene and/or overexpression of its protein have been reported in numerous cancers, including prostate, bladder, and breast tumors.

VRK3

VRK3 (vaccinia related kinase 3) lacks catalytic activity owing to the substitution of six out of eleven active site residues. The structure of VRK3 reveals how non-conservative substitutions of these catalytic motifs compromise VRK3 catalytic competence. Of detrimental effect to ATP binding and hence catalytic activity, are the substitution of a small glycine residue from the glycine-rich loop (residue Asp175) and residue Gln177. It is predicted that the substitution clashes with the phosphate moiety of ATP. Consistent with these structural observations, VRK3 is incapable of binding nucleotides. The VRK3 structure is similar to the structure of the closely related active kinase VRK2. Recent studies suggest that VRK3 direct binding inhibits the vaccinia H1-related (VHR) phosphatase, a dual-specificity phosphatase that dephosphorylates and inactivates ERK (See for example, Kang, et al., Nat Cell Biol 2006; 8(8):863-869; Kang, et al., Biochim Biophys Acta 2008; 1783(1):49-58). Thus, VRK3 regulates MAP kinase signalling through inhibition of ERK activity.

KSR

The kinase suppressor of Ras (KSR) family of proteins comprise a conserved group of molecular scaffolds that function as modulators of Ras signaling by bringing together the different components of the Raf/MEK/ERK cascade. These predicted pseudokinases act as scaffolds bringing together the three components of the MAP kinase pathway (MAP-KKK, MAPKK and MAPK), thus regulating signalling output and potentiation. The pseudokinase domain of KSR1 binds MEK and RAF, whereas ERK is recruited to the signalling complex via a conserved domain N-terminal to the pseudokinase domain. In addition, recent work that established KSR2 as an important scaffold (similar to KSR1) of MAP kinase signalling, reveals KSR2 can be regulated by dephosphorylation by calcineurin in response to changing Ca2+ levels. (Dougherty, et al., Mol Cell 2009; 34(6):652-662) KSR proteins are similar to members of the Raf family of S/T kinases, and as such are included in the tyrosine-like kinase (TLK) group of kinases. All KSR proteins identified so far have all or some of five distinct domains named Conserved Area (CA) 1 to CA5.

Treatment of Cancer

In some embodiments, the methods described here for treating cancer in a human subject comprise administering to a patient in need a compound that (i) stabilizes a protein kinase in the inactive state and (ii) is not an ATP competitive inhibitor of the protein kinase in the active state. In certain embodiments, the cancer is resistant, refractory or non-responsive to a type I inhibitor of the protein kinase. In certain embodiments, the cancer is resistant, refractory or non-responsive to a pan-RAF kinase drug or an ATP-competitive inhibitor. In certain embodiments, the cancer is resistant, refractory or non-responsive to a drug selected from Sorafenib, PLX4032, XL281, RAF265, 885-A, ZM336372, L-779450, AZ628, AAL881, LBT613, MCP110, 17-DMAG, CI1040, AZD6244/ARRY142886, PD0325901, SB590885, DP3346, and DP2514. In certain embodiment, the cancer is resistant, refractory or non-responsive to a VEGF-targeted therapy. In certain embodiments, the cancer is associated with a mutant form of RAF kinase; preferably the mutant form is a BRAF kinase selected from a mutant T5291, T529N, G464A, G464E, G464V, G466A, G466E, G466V, G469A, G469E, N581S, E586K, F595L, G596R, L597V, L597R, T5991, V600E, and K601E. In another embodiment, the mutant form is a CRAF gatekeeper mutant selected from T421N and T4211. In other embodiments, the cancer is selected from melanoma, breast cancer, colon cancer, pancreatic cancer, lung cancer (e.g. non-small cell lung cancer), kidney cancer, glioblastoma, and colon cancer. In certain embodiments, the cancer is characterized by stroma rich tumors. In certain embodiments, the cancer has a mutant or aberration selected from N-Ras, B-RAF(V600E), B-RAF/Ras, HER1, K-Ras, or PI3K. In certain embodiments, the cancer exhibits up-regulation of the RAF-MEK-ERK pathway. In some embodiments, the compound for the methods is a selective type II inhibitor; preferably a selective type II inhibitor of RAF kinase (e.g. B-RAF kinase); more preferably the compound is also a selective type II inhibitor of a PDGF receptor. In some embodiments, the compound modulates A-RAF. In other embodiments, the compound for the methods inhibits the heterodimerization of BRAF with CRAF. In some embodiments, the compound inhibits the phosphorylation of S338 of C-RAF. In another embodiment, the compound does not inhibit active kinases selected from the group B-RAF, C-RAF, VEGFR1, VEGFR2, Flt3, Kit, and PDGFRβ. In some embodiments, the compound arrests tumor cells in G2/M.

In some embodiments, the compound is an allosteric inhibitor of PDGFRα, PDGFRβ, Flt3 and/or c-Kit. In some embodiments, the compound comprises an amino-triazole scaffold. In some embodiments, the compound has the structure

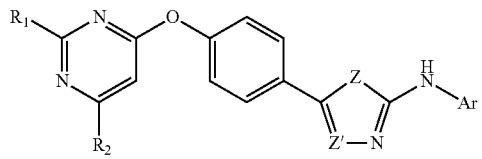

wherein $R_1$ and $R_2$ are independently hydrogen, optional substituted alkyl, halogen, optional substituted amine, $NH_2$, optional substituted alkyoxy, optional substituted thioalkyl, $CF_3S$, optional substituted alkylsulfinyl or optional substituted alkylsulfonyl; Z is NH, S or O; Z' is N or C; and Ar is phenyl or bicyclic phenyl optionally substituted with one or more substituents selected from $C_{1-6}$ alkyl, halogen substituted $C_{1-6}$ alkyl, halogen substituted $C_{1-6}$ alkoxy, and $C_{3-10}$ cycloalkyl. In certain embodiments, the compound has the structure

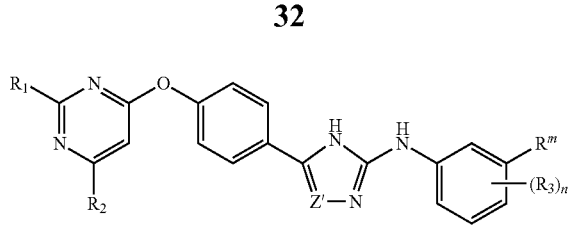

wherein $R^m$ is $C_{1-6}$ alkyl, or halogen substituted $C_{1-6}$ alkyl; and $R_3$ is independently a hydrogen, $C_{1-6}$ alkyl, halogen substituted $C_{1-6}$ alkyl, halogen substituted $C_{1-6}$ alkoxy, or $C_{3-10}$ cycloalkyl; or, optionally, $R^m$ and $R_3$ are joined to form a five to seven membered carbocycle; and n is 0-4. In certain embodiments, the compound has the structure

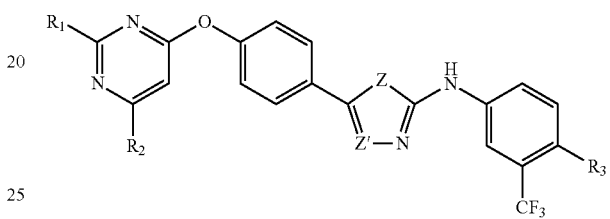

wherein $R_3$ is hydrogen or halogen; and Z is NH, S or O. In another embodiment, the compound is selected from

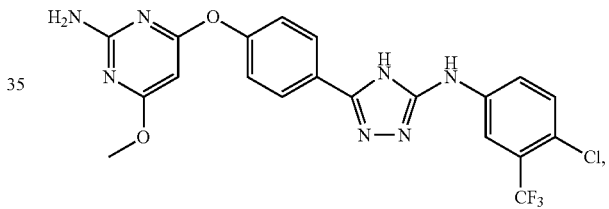

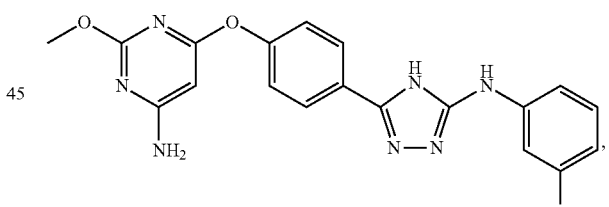

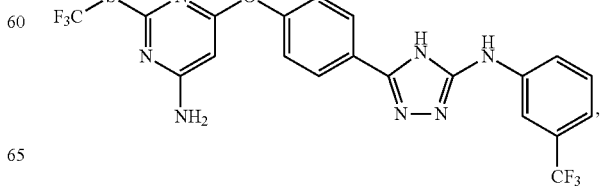

33
-continued
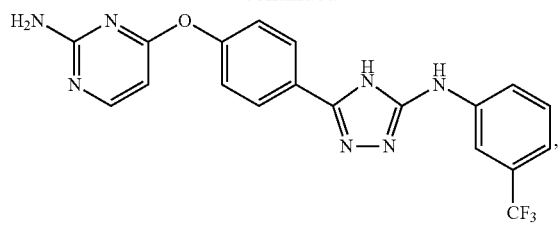
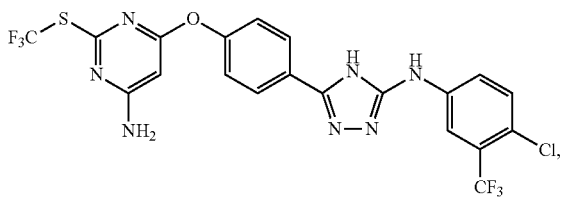
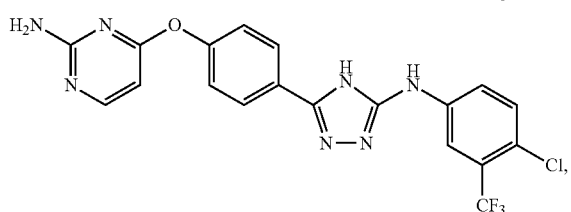
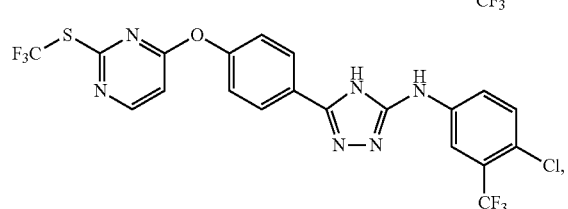
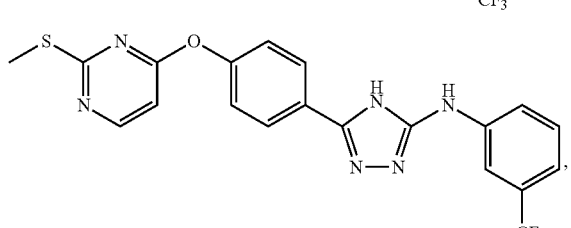
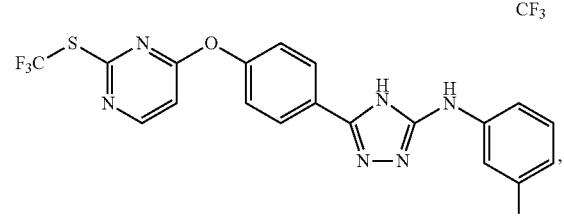
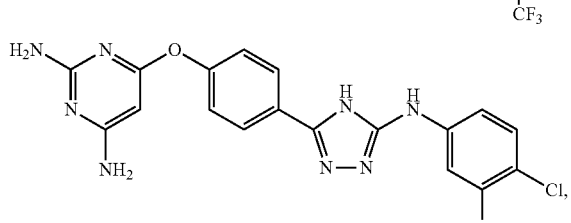
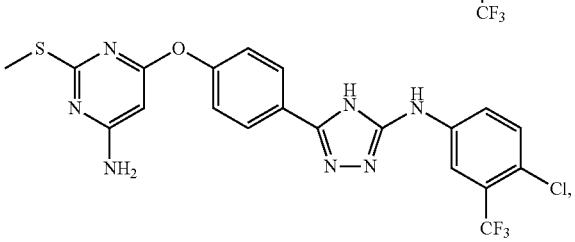
34
-continued
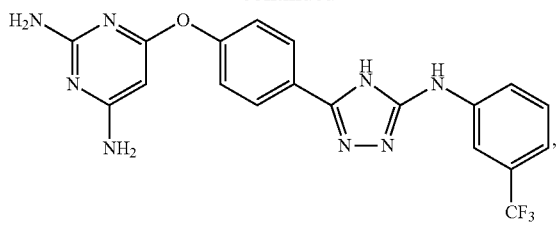
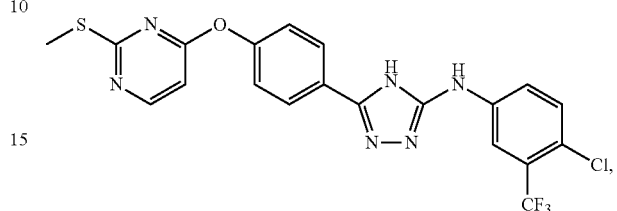
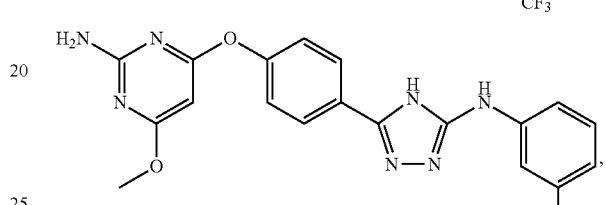
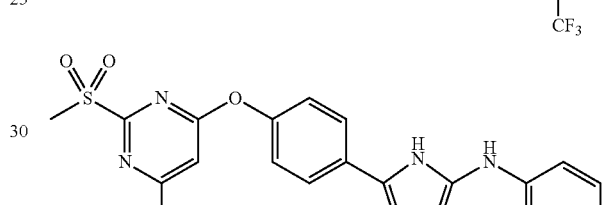
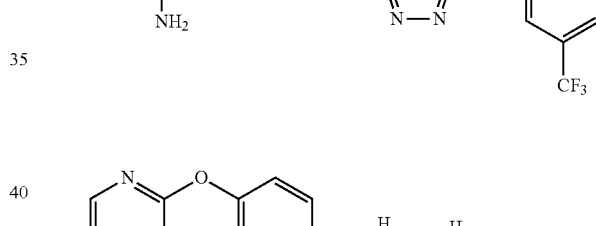
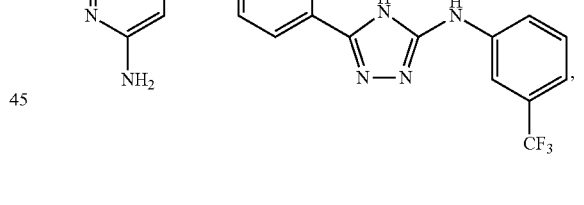
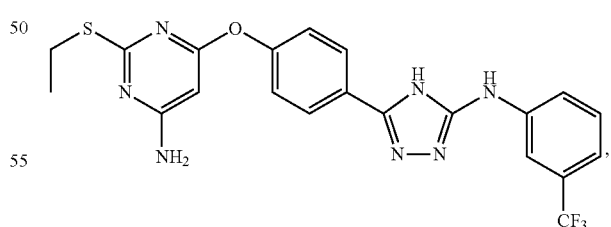
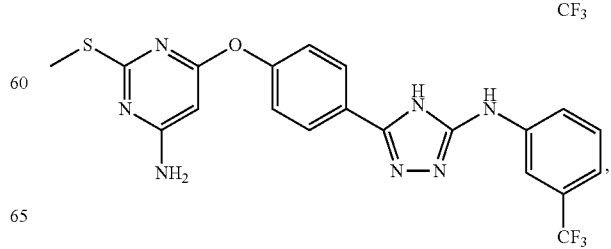

-continued

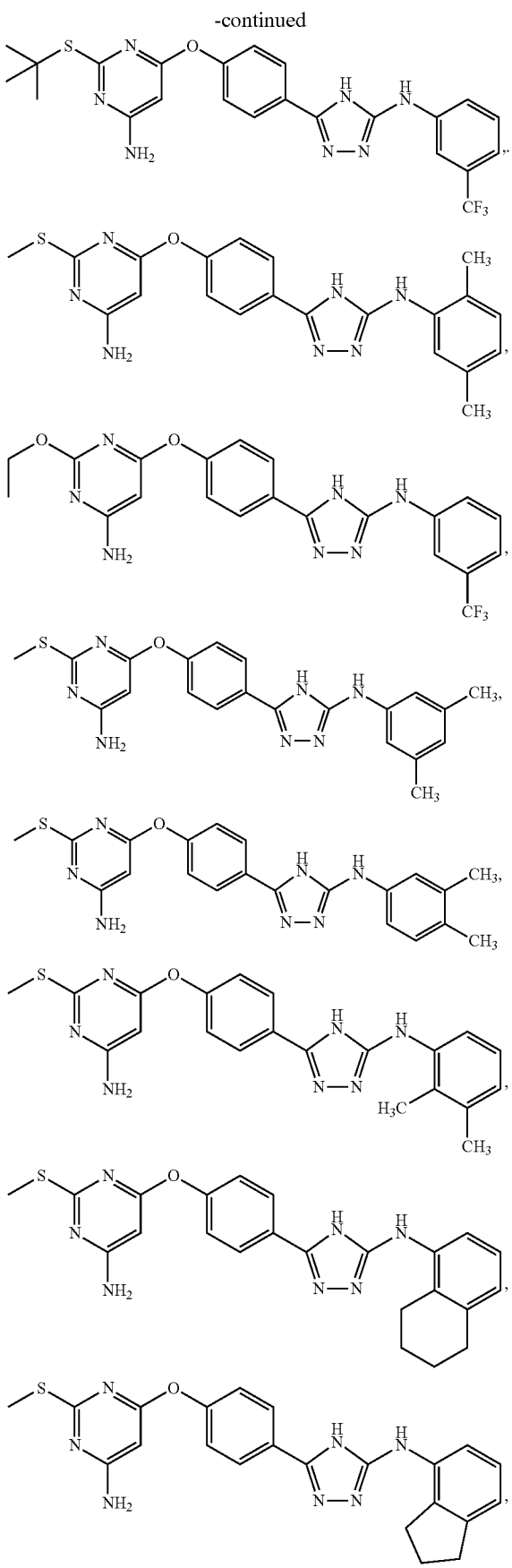

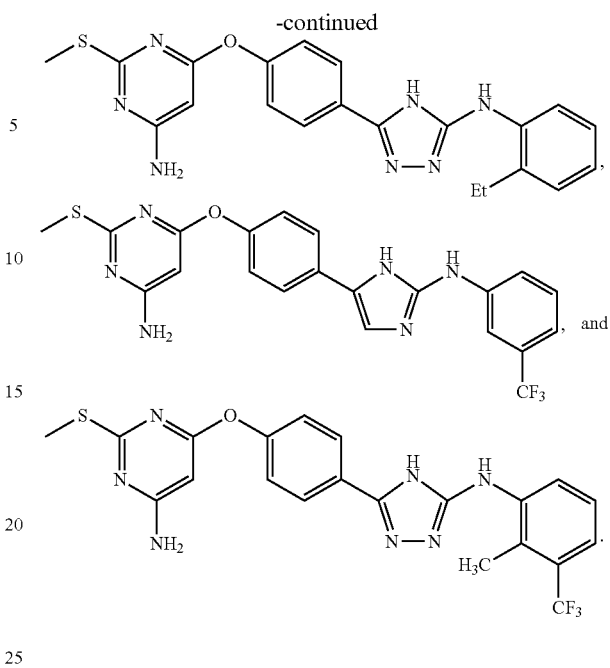

In certain embodiments, the compound is administered orally to the patient in need. In some embodiments, the patient is also provided with a therapy selected from anti-angiogenic therapy, chemotherapy or radiation therapy. In other embodiments, the response of the patient to the compound is monitored by inhibition of the phosphorylation of S338 of CRAF.

In some embodiments, cancers that are treated by the methods provided herein include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastom, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiforme, oligodendroglioma, schwannoma, retinoblastoma, congenital tumors), spinal cord (neurofibroma, meningioma, glioma, sarcoma); Gynecological: uterus (endometrial carcinoma), cervix (cervical carcinoma, pre-tumor cervical dysplasia)! ovaries (ovarian carcinoma [serous cystadenocarcinoma, mucinous cystadenocarcinoma, endometrioid tumors, celioblastoma, clear cell carcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles, dysplastic nevi, lipoma, angioma, dermatofibroma, keloids, psoriasis; and Adrenal glands: neuroblastoma.

In some embodiments, acute myelocytic leukemia (AML) and/or acute lymphocytic leukemia (ALL) are treated using compounds (i.e., allosteric kinase inhibitors described herein) in monotherapy or combination therapy.

ASK1-Mediated Apoptosis

In other embodiments, the methods described here for preventing inhibition of ASK1-mediated apoptosis in a cell comprise contacting the cell with a compound that (i) stabilizes the protein kinase in the inactive state and (ii) is not an ATP competitive inhibitor of the protein kinase in the active state. In some embodiments, the compound for the methods is a selective type II inhibitor; preferably a selective type II inhibitor of RAF kinase (e.g. B-RAF kinase); more preferably the compound is also a selective type II inhibitor of a PDGF receptor. In some embodiments, the compound for the methods modulates A-RAF. In other embodiments, the compound for the methods inhibits the heterodimerization of BRAF with CRAF. In some embodiments, the compound inhibits the phosphorylation of S338 of C-RAF. In another embodiment, the compound does not inhibit active kinases selected from the group B-RAF, C-RAF, VEGFR1, VEGFR2, Flt3, Kit, and PDGFRβ. In some embodiments, the compound is an allosteric inhibitor of PDGFRα, PDGFRβ, Flt3 and/or c-Kit. In some embodiments, the compound described herein arrests tumor cells in G2/M. For example, exemplary compound 6 arrests tumor cells such as HCT-116, Mia-Paca2, FG, XPA-1, BXPC3, MDA-231 and U251 in G2/M. In some embodiments, the compound has the structure

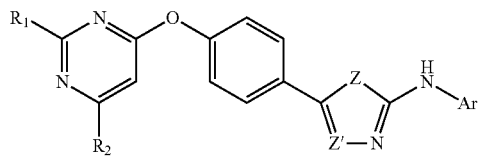

wherein $R_1$ and $R_2$ are independently hydrogen, optional substituted alkyl, halogen, optional substituted amine, $NH_2$, optional substituted alkyoxy, optional substituted thioalkyl, $CF_3S$, optional substituted alkylsulfinyl or optional substituted alkylsulfonyl; Z is NH, S or O; Z' is N or C; and Ar is phenyl or bicyclic phenyl optionally substituted with one or more substituents selected from $C_{1-6}$ alkyl, halogen substituted $C_{1-6}$ alkyl, halogen substituted $C_{1-6}$ alkoxy, and $C_{3-10}$ cycloalkyl. In certain embodiments, the compound has the structure

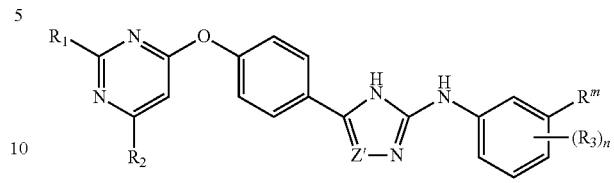

wherein $R^m$ is $C_{1-6}$ alkyl, or halogen substituted $C_{1-6}$ alkyl; and $R_3$ is independently a hydrogen, $C_{1-6}$ alkyl, halogen substituted $C_{1-6}$ alkyl, halogen substituted $C_{1-6}$ alkoxy, or $C_{3-10}$ cycloalkyl; or, optionally, $R^m$ and $R_3$ are joined to form a five to seven membered carbocycle; and n is 0-4. In certain embodiments, the compound has the structure

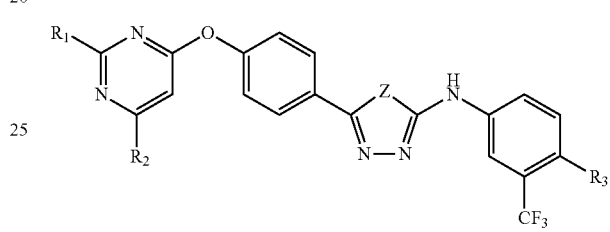

wherein $R_3$ is hydrogen or halogen; and Z is NH, S or O. In another embodiment, the compound is selected from

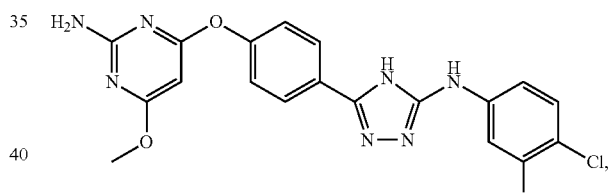

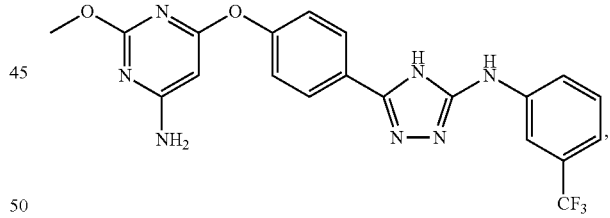

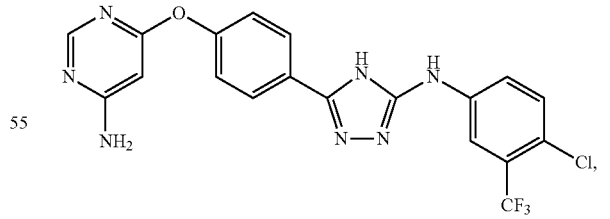

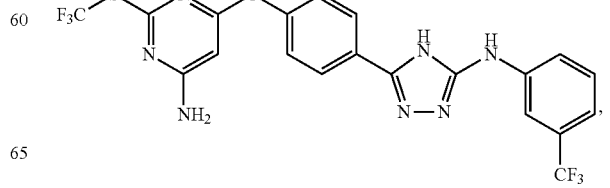

39
-continued
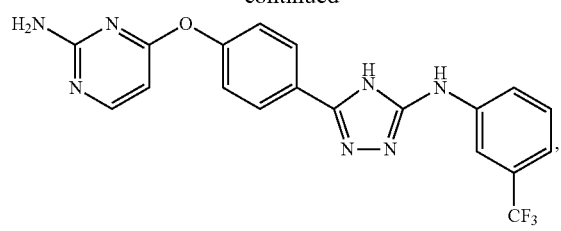
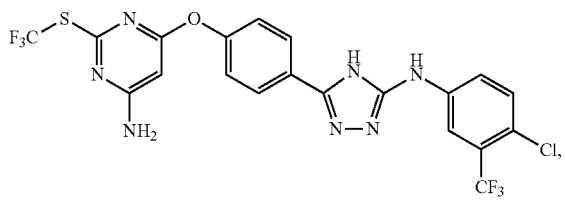
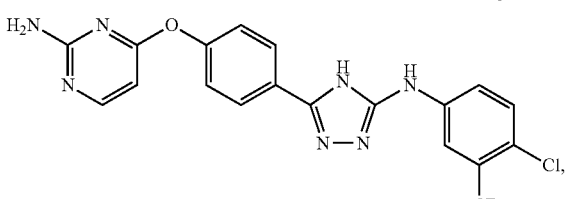
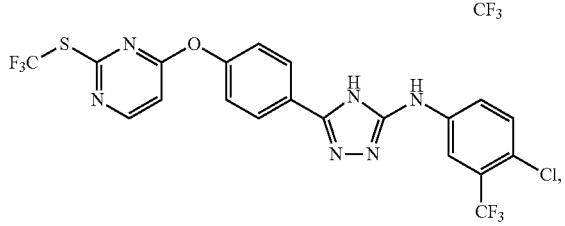
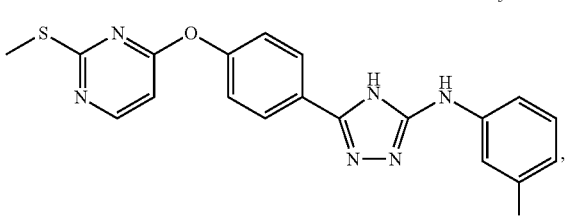
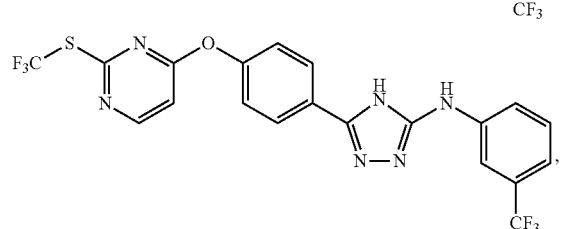
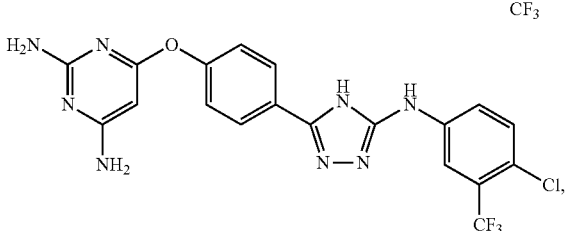
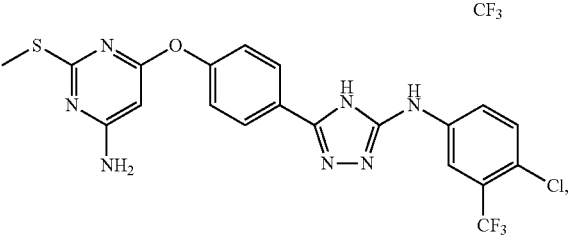
40
-continued
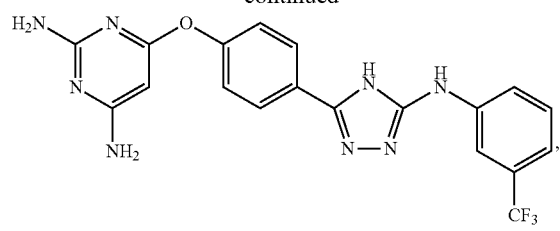
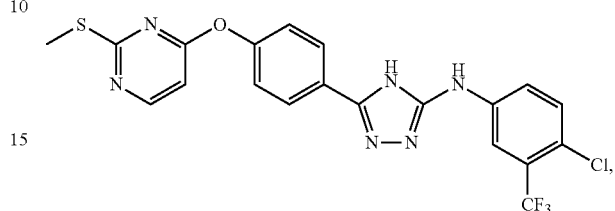
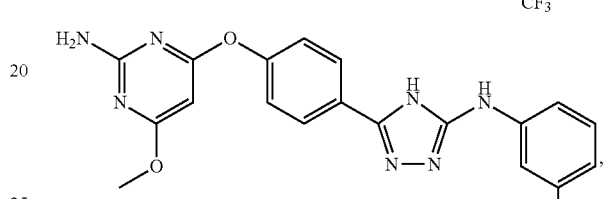
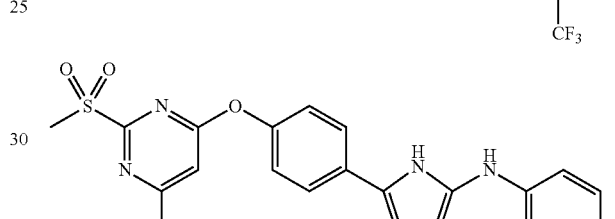
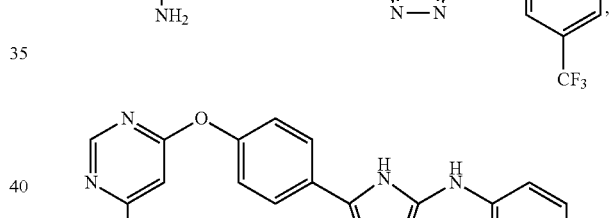
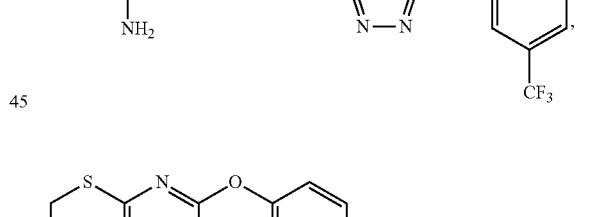
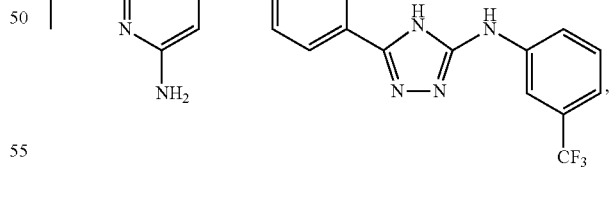
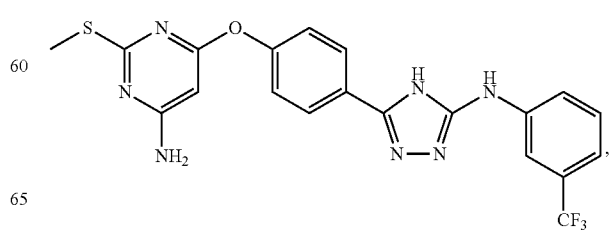

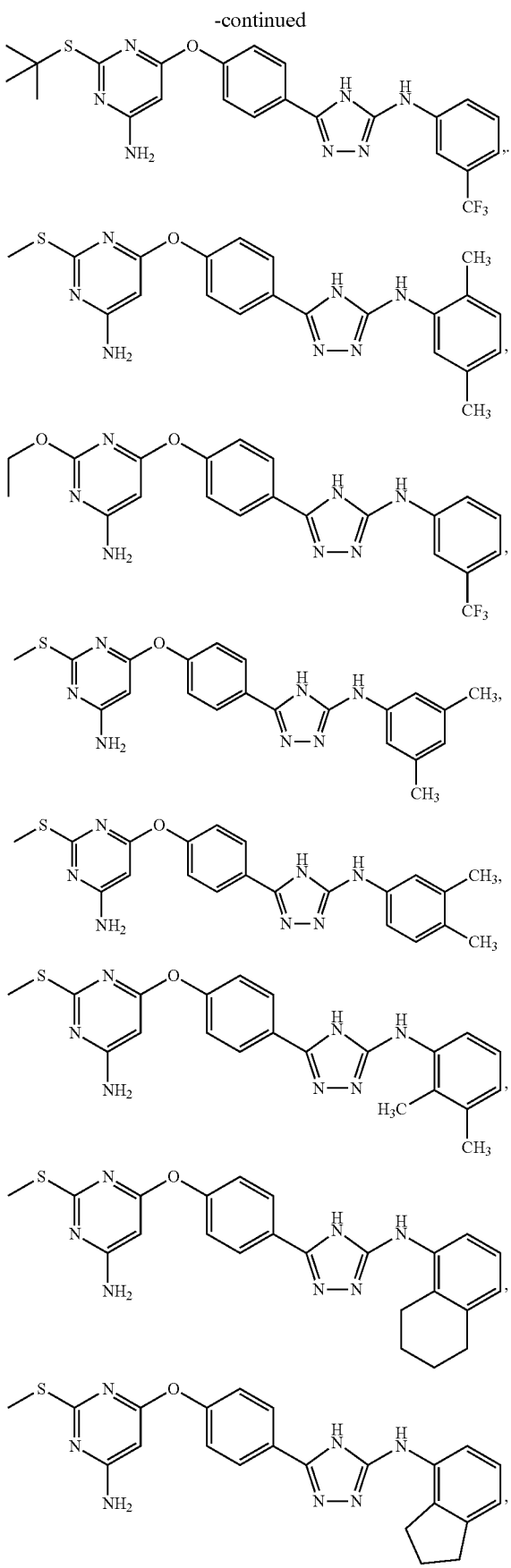

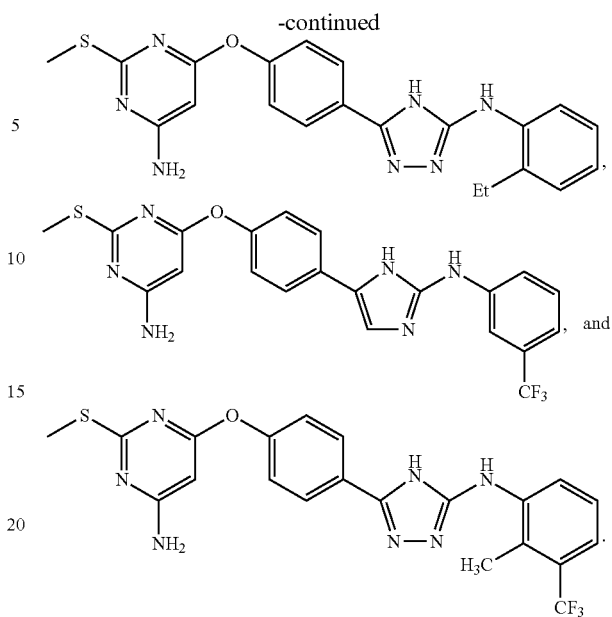

Apoptosis or programmed cell death is a physiologic process that plays a central role in normal development and tissue homeostasis. Many factors interact in complex pathways to lead to cell death or cell survival. Genotoxic stress induced by anticancer drugs can lead to apoptosis of both angiogenic endothelia cells and proliferating tumor cells. However, growth factors such as basic fibrolast growth factor (bFGF) and VEGF present within the tumor microenvironment by suppressing apoptotic mechanisms in these cells. It was identified that apoptosis signal-regulating kinase 1 (ASK1) can be a target of bFGF-mediated survival signaling in ECs (Alavi, et al. (2007) Cancer Res 67:(6) 2766). Specifically, it is thought that bFGF stimulation promotes the formation of a Raf-1/ASK1 complex at the mitochondria, inhibits ASK1 kinase activity, and protects ECs from genotoxic stress. Mutation of the Raf-1 activation domain (SS338/9AA) not only prevents Raf-1/ASK1 complex formation but also abolishes bFGF-mediated EC protection from genotoxic stress. Thus, selective type II inhibitors protein kinase, stabilizing a protein kinase in the inactive state with a compound that are not ATP competitive inhibitors of the protein kinase in the active state, which block ASK1 at the mitochondria would prevent stress-mediated apoptosis.

Sensitizing a Cell to an Extrinsic Stress

In some embodiments, the methods described herein are used to sensitize a cell to an extrinsic stress comprising contacting a cell (before or after exposing the cell to a stress) with a compound that (i) stabilizes the protein kinase in the inactive state and (ii) is not an ATP competitive inhibitor of the protein kinase in the active state. In certain embodiments, the stress is selected from hypoxia, chemotherapy, radiotherapy or glucose/nutrient starvation. In some embodiments, the compound for the methods is a selective type II inhibitor; preferably a selective type II inhibitor of RAF kinase (e.g. B-RAF kinase); more preferably the compound is also a selective type II inhibitor of a PDGF receptor. In some embodiments, the compound modulates A-RAF. In other embodiments, the compound for the methods inhibits the heterodimerization of BRAF with CRAF. In some embodiments, the compound inhibits the phosphorylation of S338 of C-RAF. In another embodiment, the compound does not inhibit active kinases selected from the group B-RAF, C-RAF, VEGFR1, VEGFR2, Flt3, Kit, and PDGFRβ. In some embodiments, the compound is an allosteric inhibitor of PDGFRα, PDGFRβ, Flt3 and/or c-Kit. In some embodiments, the compound has the structure

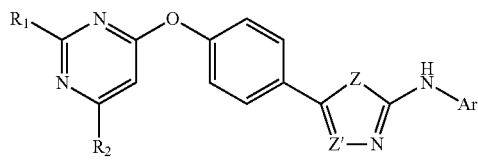

wherein $R_1$ and $R_2$ are independently hydrogen, optional substituted alkyl, halogen, optional substituted amine, $NH_2$, optional substituted alkyoxy, optional substituted thioalkyl, $CF_3S$, optional substituted alkylsulfinyl or optional substituted alkylsulfonyl; Z is NH, S or O; Z' is N or C; and Ar is phenyl or bicyclic phenyl optionally substituted with one or more substituents selected from $C_{1-6}$ alkyl, halogen substituted $C_{1-6}$ alkyl, halogen substituted $C_{1-6}$ alkoxy, and $C_{3-10}$ cycloalkyl. In certain embodiments, the compound has the structure

wherein $R^m$ is $C_{1-6}$ alkyl, or halogen substituted $C_{1-6}$ alkyl; and $R_3$ is independently a hydrogen, $C_{1-6}$ alkyl, halogen substituted $C_{1-6}$ alkyl, halogen substituted $C_{1-6}$ alkoxy, or $C_{3-10}$ cycloalkyl; or, optionally, $R^m$ and $R_3$ are joined to form a five to seven membered carbocycle; and n is 0-4. In certain embodiments, the compound has the structure

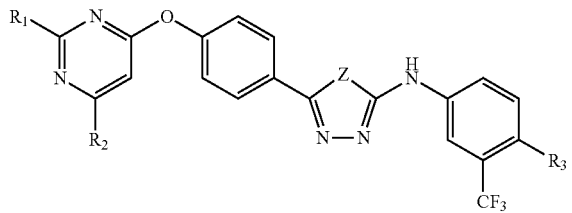

wherein $R_3$ is hydrogen or halogen; and Z is NH, S or O. In another embodiment, the compound is selected from

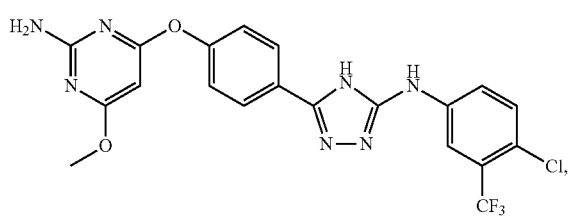

-continued

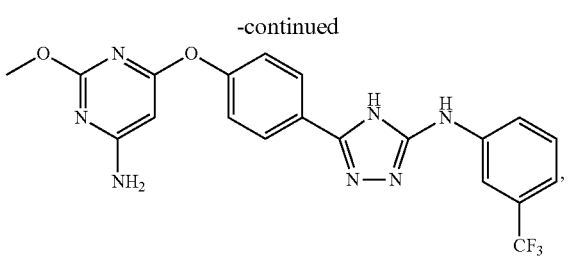

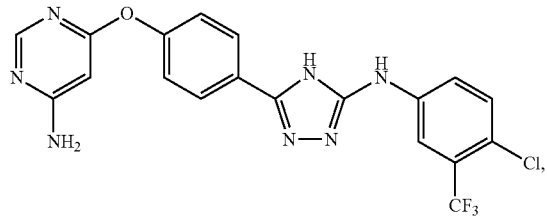

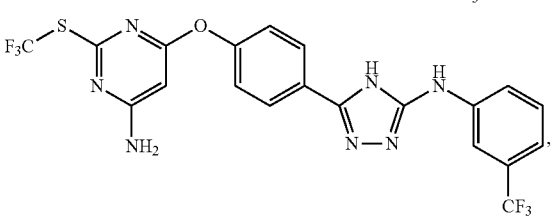

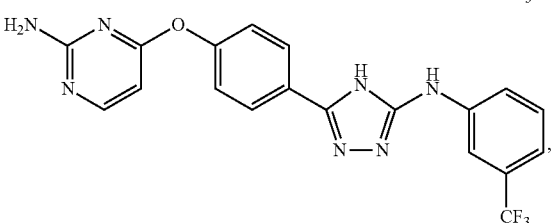

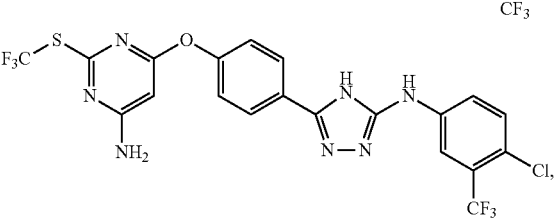

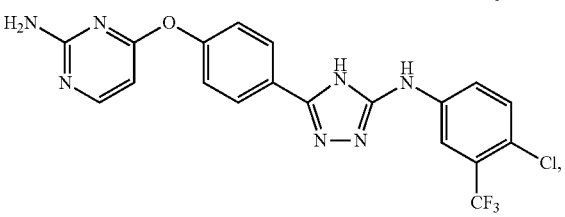

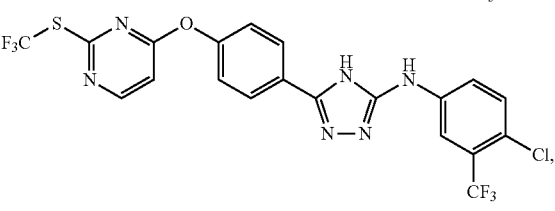

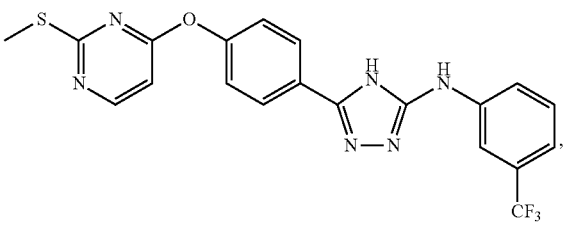

45
-continued
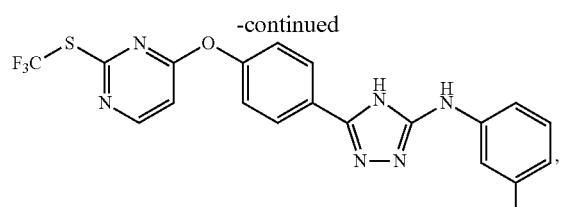
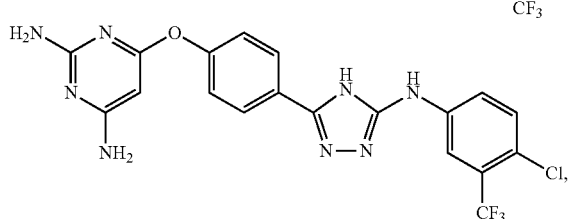
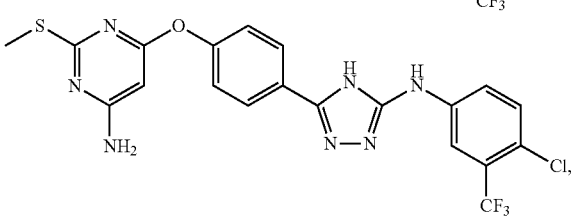
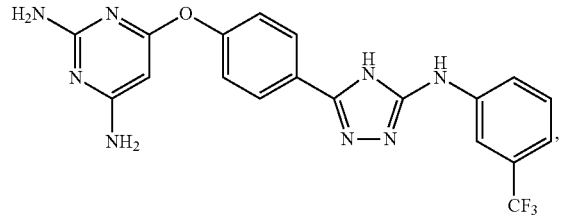
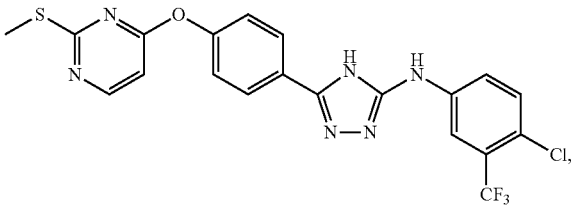
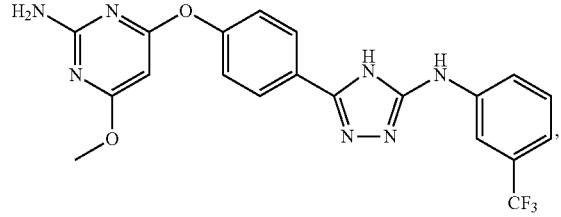
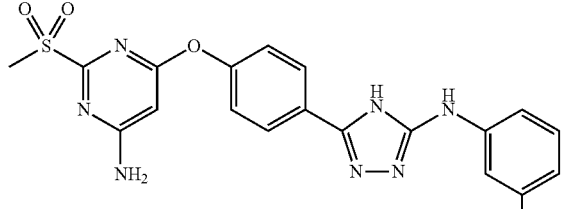
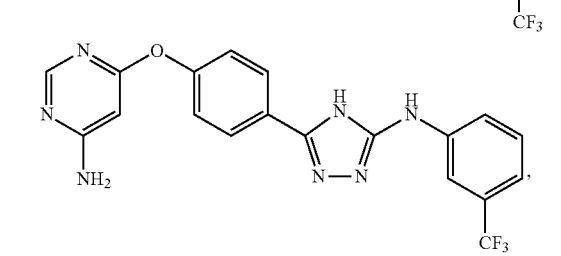
46
-continued
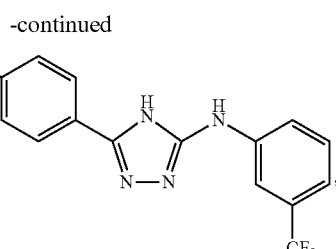
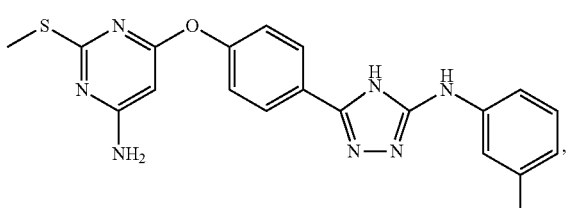
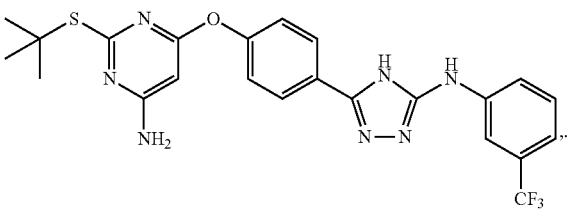
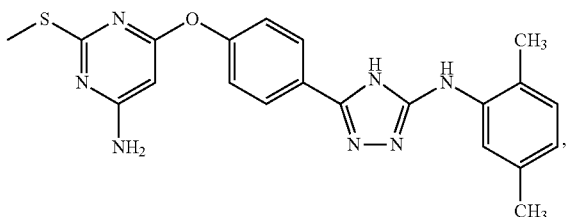
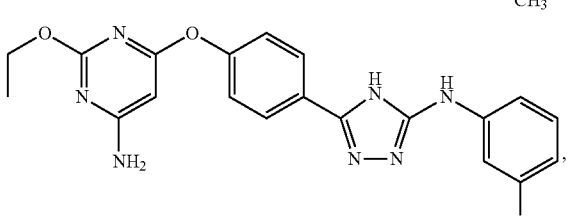
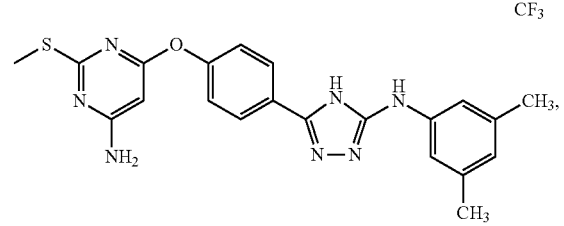
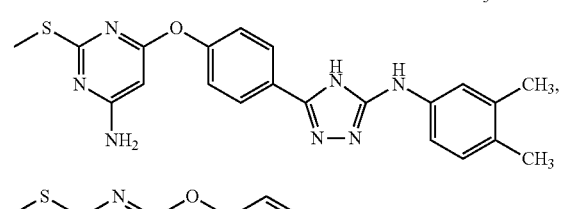
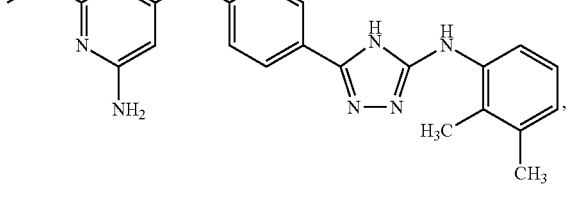

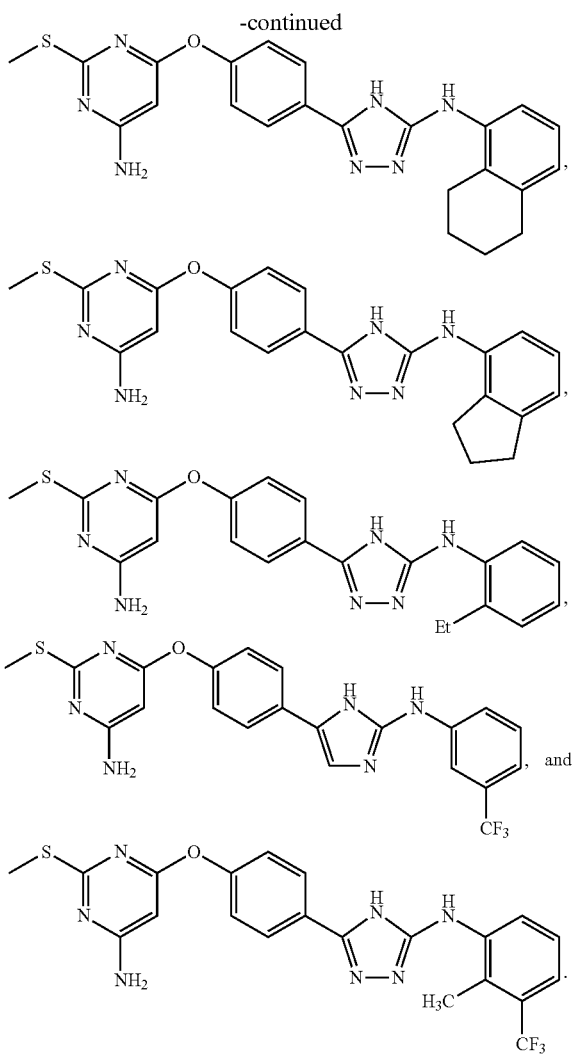

Combination Treatments

In general, the compositions described herein and, in embodiments where combinational therapy is employed, other agents do not have to be administered in the same pharmaceutical composition, and in some embodiments, because of different physical and chemical characteristics, are administered by different routes. In some embodiments, the initial administration is made according to established protocols, and then, based upon the observed effects, the dosage, modes of administration and times of administration is modified by the skilled clinician.

In some embodiments, therapeutically-effective dosages vary when the drugs are used in treatment combinations. Combination treatment further includes periodic treatments that start and stop at various times to assist with the clinical management of the patient. For combination therapies described herein, dosages of the co-administered compounds vary depending on the type of co-drug employed, on the specific drug employed, on the disease, disorder, or condition being treated and so forth.

It is understood that in some embodiments, the dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in other embodiments, the dosage regimen actually employed varies widely and therefore deviates from the dosage regimens set forth herein.

Combinations of compounds (i.e., allosteric kinase inhibitors described herein) with other anti-cancer or chemotherapeutic agents are intended to be covered. In some embodiments, examples of such agents are found in *Cancer Principles and Practice of Oncology* by V. T. Devita and S. Hellman (editors), 6$^{th}$ edition (Feb. 15, 2001), Lippincott Williams & Wilkins Publishers. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors, nitrogen mustards, nitroso ureas, angiogenesis inhibitors, inhibitors of cell proliferation and survival signaling pathway, apoptosis inducing agents, agents that interfere with cell cycle checkpoints, agents that interfere with receptor tyrosine kinases (RTKs), integrin blockers, NSAIDs, PPAR agonists, inhibitors of inherent multidrug resistance (MDR), anti-emetic agents, agents useful in the treatment of anemia, agents useful in the treatment of neutropenia, immunologic-enhancing drugs, biphosphonates, aromatase inhibitors, agents inducing terminal differentiation of neoplastic cells, γ-secretase inhibitors, cancer vaccines, and any combination thereof.

"Estrogen receptor modulators" refers to compounds that interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpr-opanoate, 4,4'-dihydroxybenzophenone-2,4-dinitrophenyl-hydrazone, and SH646.

In some embodiments, estrogen receptor modulators are tamoxifen and raloxifene.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine-(chloro)platinum(II)]-tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)-benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)-ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB, 8aa,9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',':6,7)colchic(2,3-d)-1,3-dioxol-6-one, 2,3-(methylenedioxy)-5-methyl-7-hydroxy-8-methoxybenzo [c]-phenanthridinium, 6,9-bis[(2-aminoethyl)-amino]benzo [g]isoquinoline-5,10-dione, 5-(3-aminopropylamino)-7,10-dihydroxy-2-(2-hydroxyethylaminomethyl)-6H-pyrazolo[4, 5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2-, 1-c]quinolin-7-one, and dimesna.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxy-cytidine, N-[5-(2,3-dihydro-benzofuryl)sulfonyl]-N'-(3,4-dichlorophenyl)urea, N6-[4-deoxy-4-[$N^2$-[2(E),4(E)-tetradecadienoyl]-glycylamino]-L-glycero-B-L-manno-heptopyranosyl]-adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 1'-acetyl-8-(carbamoyloxymethyl)-4-formyl-6-methoxy-14-oxa-1,1'-diazatetracyclo(7.4.1.0.0)-tetradeca-2, 4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which in some embodiments are delivered via recombinant virus-mediated gene transfer.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2(1H)-quinolinone, (−)-6-[amino(4-chloropheny-1)(1-methyl-1H-imidazol-5-yl) methyl]-4-(3-chlorophenyl)-1-methyl-2(1H)-quinolinone, (+)-6-[amino(4-chlorophenyl)(1-methyl-1H-imidazol-5-yl) methyl]-4-(3-chlorophenyl)-1-methyl-2(1H)-quinolinone, 5(S)-n-butyl-1-(2,3-dimethyl-phenyl)-4-[1-(4-cyanobenzyl)-5-imidazolylmethyl]-2-piperazinone, (5)-1-(3-chlorophenyl)-4-[1-(4-cyanobenzyl)-5-imidazolylmethyl]-542-(ethanesulfonyl)-methyl)-2-piperazinone, 5(S)-n-butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-yl-ethyl)carbamoyl]-piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2] bipyridin-5'-ylmethyl]-3H-imidazol-4-ylmethyl}benzonitrile, 4-{3-[4-(2-oxo-2H-[1,2]bipyridin-5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl]benzonitrile, 18,19-dihydro-19-oxo-5H,17H-6,10:12,16-dimetheno-1H-imidazo[4,3-c][1,11,4] dioxa-azacyclononadecine-9-carbonitrile, (±)-19,20-dihydro-19-oxo-5H-18,21-ethano-12,14-etheno-6,10-metheno-22H-benzo[d]imidazo[4,3-k][1,6,9,12]-oxatriaza-cyclooctadecine-9-carbonitrile, 19,20-dihydro-19-oxo-5H, 17H-18,21-ethano-6,10:12,16-dimetheno-22H-imidazo[3,4-h][1,8,11,14]oxatriazacyclo-eicosine-9-carbonitrile, and (±)-19,20-dihydro-3-methyl-19-oxo-5H-18,21-ethano-12,14-etheno-6,10-metheno-22H-benzo[d]imidazo[4,3-k][1,6,9, 12]oxa-triazacyclooctadecine-9-carbonitrile.

"HMG-CoA reductase inhibitors" refers to inhibitors of 3-hydroxy-3-methylglutaryl-CoA reductase. In some embodiments, compounds which have inhibitory activity for HMG-CoA reductase are readily identified by using known assays. The terms "HMG-CoA reductase inhibitor" and "inhibitor of HMG-CoA reductase" have the same meaning when used herein.

In some embodiments, examples of HMG-CoA reductase inhibitors that are used include but are not limited to lovastatin (MEVACOR®), simvastatin (ZOCOR®), pravastatin (PRAVACHOL®), fluvastatin (LESCOL®), atorvastatin (LIPITOR®) and cerivastatin (also known as rivastatin and BAYCHOL®). In some embodiments, the structural formulas of these and additional HMG-CoA reductase inhibitors that are used in the instant methods are described at page 87 of M. Yalpani, "Cholesterol Lowering Drugs", Chemistry &

Industry, pp. 85-89 (Feb. 5, 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is intended to be covered.

In some embodiments, in HMG-CoA reductase inhibitors where an open-acid form exists, salt and ester forms are formed from the open-acid, and all such forms are included within the meaning of the term "HMG-CoA reductase inhibitor" as used herein. In some embodiments, the HMG-CoA reductase inhibitor is selected from lovastatin and simvastatin. In one embodiment, the HMG-CoA reductase inhibitor is simvastatin.

Herein, the term "pharmaceutically acceptable salts" with respect to the HMG-CoA reductase inhibitor shall mean non-toxic salts of the compounds employed which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl)aminomethane. In other embodiments, further examples of salt forms of HMG-CoA reductase inhibitors include, but are not limited to, acetate, benzenesulfonate, benzoate, bicarbonate, bisulfate, bitartrate, borate, bromide, calcium hydroxyl, camsylate, carbonate, chloride, clavulanate, citrate, dihydrochloride, hydroxyl, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

In other embodiments, ester derivatives of the described HMG-CoA reductase inhibitor compounds act as prodrugs which, when absorbed into the bloodstream of a warm-blooded animal, cleave in such a manner as to release the drug form and permit the drug to afford improved therapeutic efficacy.

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232, 632. Examples of reverse transcriptase inhibitors include delaviridine, efavirenz, GS-840, HB Y097, lamivudine, nevirapine, AZT, 3TC, ddC, and ddI. It has been reported that HIV protease inhibitors, such as indinavir or saquinavir, have potent anti-angiogenic activities and promote regression of Kaposi sarcoma.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib, valecoxib, and rofecoxib, carboxyamidotriazole, combretastatin A-4, squalamine, 6-O-chloroacetyl-carbonyl)-fumagillol, thalidomide, angiostatin, troponin-1, angiotensin II antagonists, and antibodies to VEGF.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]-methyl]-1H-1,2,3-triazole-4-carboxamide, CM101, squalamine, combretastatin, RP14610, NX31838, sulfated mannopentose phosphate, 7,7-(carbonyl-bis[imino-N-methyl-4,2-pyrrolocarbonyl-imino[N-methyl-4,2-pyrrole]-carbonylimino]-bis-(1,3-naphthalene disulfonate), and 3-[(2,4-dimethylpyrrol-5-yl)methylene]-2-indolinone (SU5416).

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of CD20 (rituximab), inhibitors of cytokine receptors, inhibitors of MET, inhibitors of PDK (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCl-779 and Ariad AP23573). Such agents include small molecule inhibitor compounds and antibody antagonists.

"Apoptosis inducing agents" include, but not limited to, activators of TNF receptor family members (including the TRAIL receptors).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include, but not limited to, tyrosine kinase inhibitors such as inhibitors of c-Kit, Eph, PDGF, Flt3 and c-Met. Further agents include inhibitors of RTKs. Examples of "tyrosine kinase inhibitors" include, but not limited to, N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]-quinazoline, N-(3-ethynylphenyl)-6,7-bis(2-methoxyethoxy)-4-quinazolinamine, BIBX1382,2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, ST1571, CEP2563, 4-(3-chlorophenylamino)-5,6-dimethyl-7-H-pyrrolo[2,3-d] pyrimidinemethane sulfonate, 4-(3-bromo-4-hydroxyphenyl)amino-6,7-dimethoxyquinazoline, 4-(4'-hydroxyphenyl) amino-6,7-dimethoxyquinazoline, SU6668, SU11248, STI571A, N-4-chlorophenyl-4-(4-pyridylmethyl)-1-phthalazinamine, and EMD121974.

Compounds (i.e., allosteric kinase inhibitors described herein) are also useful in combination with platelet fibrinogen receptor (GP Iib/IIIa) antagonists, such as tirofiban, to inhibit metastasis of cancerous cells. Tumor cells also activate platelets largely via thrombin generation. This activation is associated with the release of VEGF. The release of VEGF enhances metastasis by increasing extravasation at points of adhesion to vascular endothelium (Amirkhosravi, 1999, *Platelets* 10: 285-292).

As used above, "integrin blockers" refers to compounds which selectively antagonize, inhibit or counteract binding of a physiological ligand to the $\alpha_v\beta_3$ integrin, to compounds which selectively antagonize, inhibit or counter-act binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$; $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of a $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Combinations with compounds other than anti-cancer compounds are also encompassed in the instant methods. For example, combinations of the compounds (i.e., allosteric kinase inhibitors described herein) with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. More recently, PPAR-γ agonists have been shown to inhibit the angiogenic response to VEGF in vitro; both troglitazone and rosiglitazone maleate inhibit the development of retinal neovascularization in mice. Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NPO110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid.

In some embodiments, the compounds (i.e., allosteric kinase inhibitors described herein) are used in combination with gene therapy for the treatment of cancer. In other embodiments, gene therapy is used to deliver any tumor suppressing gene. Examples of such genes include, but are not limited to, p53, which in some embodiments is delivered via recombinant virus-mediated gene transfer, Duc-4, NF-I, NF-2, RB, WT1, BRCA1, BRCA2, a uPA/uPAR antagonist.

In other embodiments, the compounds (i.e., allosteric kinase inhibitors described herein) are also administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

In some embodiments, the compounds (i.e., allosteric kinase inhibitors described herein) are employed in conjunction with anti-emetic agents to treat nausea or emesis, including acute, delayed, late-phase, and anticipatory emesis, which result from use of the compounds (i.e., allosteric kinase inhibitors described herein), alone or with radiation therapy. In further embodiments, for the prevention or treatment of emesis, compounds (i.e., allosteric kinase inhibitors described herein) are used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990, 401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that results upon administration of the instant compounds.

In other embodiments, the compounds (i.e., allosteric kinase inhibitors described herein) are also administered with an agent useful in the treatment of anemia. Such an anemia treatment agent is, for example, a continuous eythropoiesis receptor activator (such as epoetin-a).

In further embodiments, the compounds (i.e., allosteric kinase inhibitors described herein) are also administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

In some embodiments, the compounds (i.e., allosteric kinase inhibitors described herein) are also administered with an immunologic-enhancing drug, such as levamisole, *bacillus* Calmette-Guerin, octreotide, isoprinosine and Zadaxin.

In other embodiments, the compounds (i.e., allosteric kinase inhibitors described herein) are also useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate(Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

In further embodiments, the compounds (i.e., allosteric kinase inhibitors described herein) are also useful for treating or preventing breast cancer in combination with aromatase inhibitors. Examples of aromatase inhibitors include but are not limited to: anastrozole, letrozole and exemestane.

In some embodiments, the compounds (i.e., allosteric kinase inhibitors described herein) are also useful for treating or preventing cancer in combination with siRNA or RNAi therapeutics.

In some other embodiments, the compounds (i.e., allosteric kinase inhibitors described herein) are also useful for treating or preventing cancer in combination with compounds which induce terminal differentiation of the neoplastic cells. Suitable differentiation agents include the following compounds: (a) Polar compounds; (b) Derivatives of vitamin D and retinoic acid; (c) Steroid hormones; (d) Growth factors; (e) Proteases; (f) Tumor promoters; and (g) inhibitors of DNA or RNA synthesis.

"DNA methyltransferase inhibitor" refers to compounds which inhibit the methylation of the DNA base cytosine at the C-5 position of that base by the DNA methyltransferase enzyme. Examples of such DNA methyltransferase inhibitor include DNA methyltransferase inhibitors include 5-azacytosine and Zebularine®.

Examples of an antineoplastic agent include, in general, microtubule-stabilizing agents (such as paclitaxel (also known as Taxol®), docetaxel (also known as Taxotere®, epothilone A, epothilone B, desoxyepothilone A, desoxyepothilone B or their derivatives); microtubule-disruptor agents; alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, caminomycin, daunorubicin, aminopterin, methotrexate, methopterin, dichloro-methotrexate, mitomycin C, porfiromycin, Herceptin®, Rituxan®, 5-fluorouracil, 6-mercaptopurine, gemcitabine, cytosine arabinoside, podophyllotoxin or podo-phyllotoxin derivatives such as colchicines, etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins. In some embodiments, the antineoplastic agents are the taxanes and the antineoplastic agent is paclitaxel.

Radiation Therapy

In some embodiments, the compounds (i.e., allosteric kinase inhibitors described herein) are administered in combination with radiotherapy. Radiotherapy, also called radiation therapy, is the treatment of cancer and other diseases with ionizing radiation. Ionizing radiation deposits energy that injures or destroys cells in an area being treated (a "target tissue") by damaging their genetic material, making it impossible for these cells to continue to grow. Although radiation damages both cancer cells and normal cells, the latter are better able to repair themselves and function properly. In some embodiments, radiotherapy is used to treat localized solid tumors, such as cancers of the skin, tongue, larynx, brain, breast, prostate, colon, uterus and/or cervix. In some embodiments, it is also used to treat leukemia and lymphoma (cancers of the blood-forming cells and lymphatic system, respectively).

One type of radiation therapy commonly used involves photons, "packets" of energy. X-rays, gamma rays are both photon radiation to be used to treat cancer. Depending on the amount of energy they possess, the rays are used to destroy cancer cells on the surface of or deeper in the body. In other embodiments, the higher the energy of the ray beam, the deeper the rays go into the target tissue.

Another technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" includes all forms of radiation, including but not limited to α, β, and γ radiation and ultra violet light, which are capable of directly or indirectly damaging the genetic material of a cell or virus. The term "irradiation" refers to the exposure of a sample of interest to ionizing radiation. Radiotherapy with or without concurrent or sequential chemotherapy is an effective modality for head and neck, breast, skin, anogenital cancers, and certain nonmalignant diseases such as keloid, desmoid tumor, hemangioma, arteriovenous malformation, and histocytosis X. However, the therapeutic benefit is limited by radiation- and chemotherapy-induced mucosal epithelium injuries and cutaneous radiation syndrome (CRS), which include acute reactions of tissue swelling, mucositis, dermatitis, desquamation, and ulceration, and long-term effects of tissue/skin fibrosis, necrosis, and the development of life-threatening sequelae of sarcoma, squamous and basal cell carcinoma.

MEK1/2- and/or ERK1/2-Mediated Cellular Proliferation or Migration

In other embodiments, the methods described here for inhibiting MEK1/2- and/or ERK1/2-mediated cellular proliferation or migration comprise contacting a cell with a compound that (i) stabilizes the protein kinase in the inactive state and (ii) is not an ATP competitive inhibitor of the protein kinase in the active state. In certain embodiments, the compound blocks VEGF- and/or FGF-stimulated endothelial responses in tumor angiogenesis. In some embodiments, the compound for the methods is a selective type II inhibitor; preferably a selective type II inhibitor of RAF kinase (e.g. a B-RAF kinase); more preferably the compound is also a selective type II inhibitor of a PDGF receptor. In other embodiments, the compound for the methods inhibits the heterodimerization of BRAF with CRAF. In some embodiments, the compound inhibits the phosphorylation of S338 of C-RAF. In another embodiment, the compound does not inhibit active kinases selected from the group B-RAF, C-RAF, VEGFR1, VEGFR2, Flt3, Kit, and PDGFRβ. In some embodiments, the compound is an allosteric inhibitor of PDGFRα, PDGFRβ, Flt3 and/or c-Kit. In some embodiments, the compound has the structure

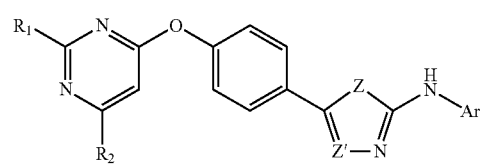

wherein $R_1$ and $R_2$ are independently hydrogen, optional substituted alkyl, halogen, optional substituted amine, $NH_2$, optional substituted alkyoxy, optional substituted thioalkyl, $CF_3S$, optional substituted alkylsulfinyl or optional substituted alkylsulfonyl; Z is NH, S or O; Z' is N or C; and Ar is phenyl or bicyclic phenyl optionally substituted with one or more substituents selected from $C_{1-6}$ alkyl, halogen substituted $C_{1-6}$ alkyl, halogen substituted $C_{1-6}$ alkoxy, and $C_{3-10}$ cycloalkyl. In certain embodiments, the compound has the structure

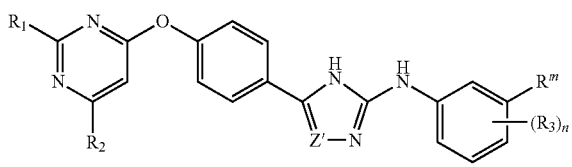

wherein R'" is C$_{1-6}$ alkyl, or halogen substituted C$_{1-6}$ alkyl; and R$_3$ is independently a hydrogen, C$_{1-6}$ alkyl, halogen substituted C$_{1-6}$ alkyl, halogen substituted C$_{1-6}$ alkoxy, or C$_{3-10}$cycloalkyl; or, optionally, R'" and R$_3$ are joined to form a five to seven membered carbocycle; and n is 0-4. In certain embodiments, the compound has the structure

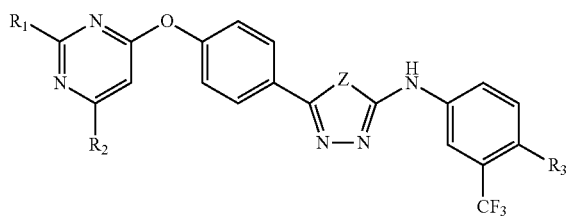

wherein R$_3$ is hydrogen or halogen; and Z is NH, S or O. In another embodiment, the compound is selected from

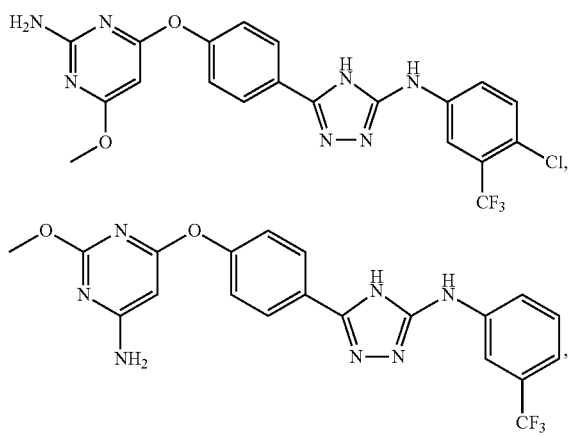

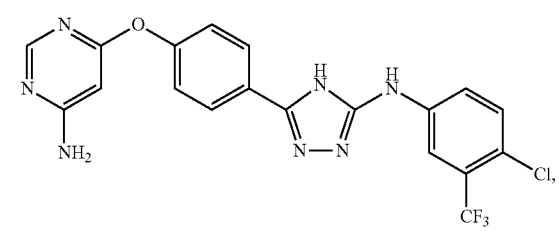

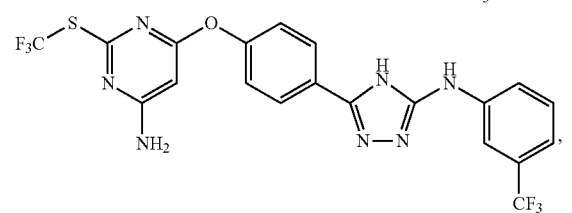

-continued

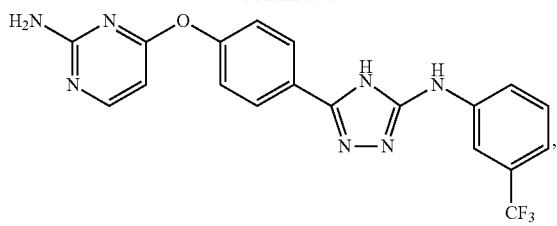

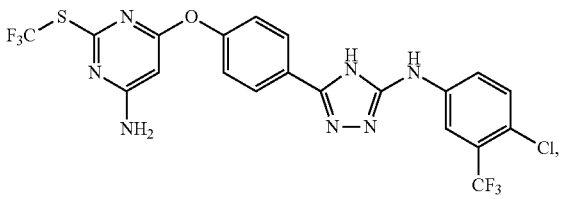

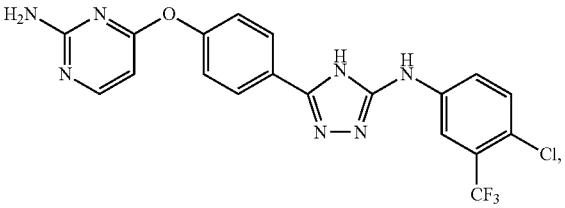

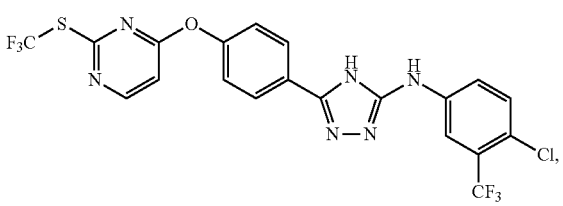

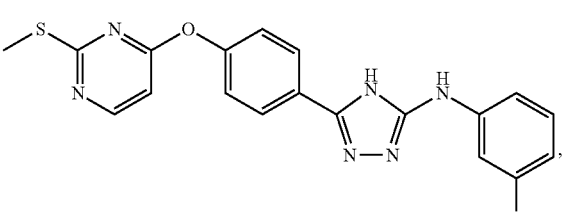

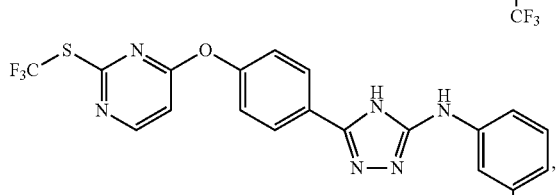

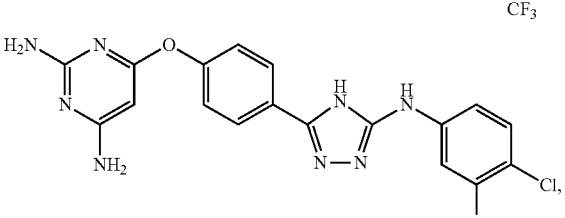

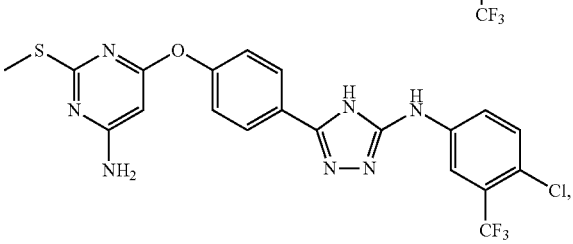

59
-continued
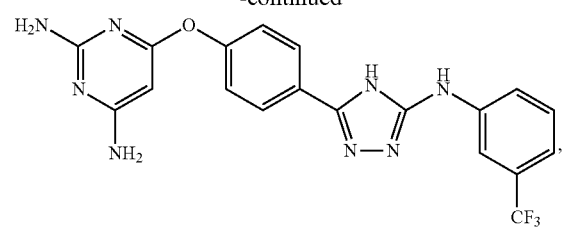
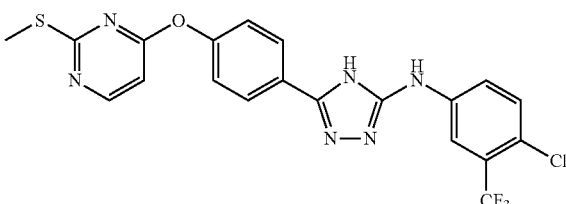
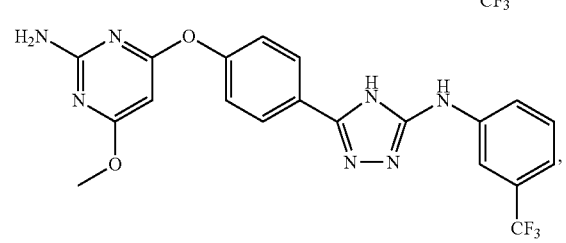
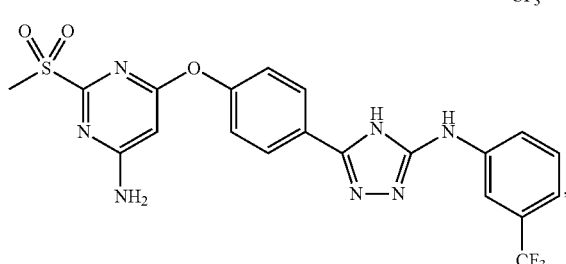
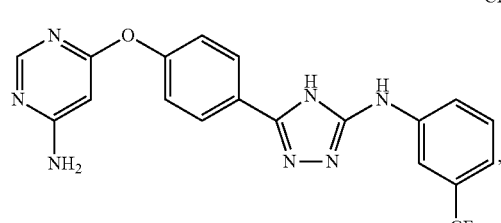
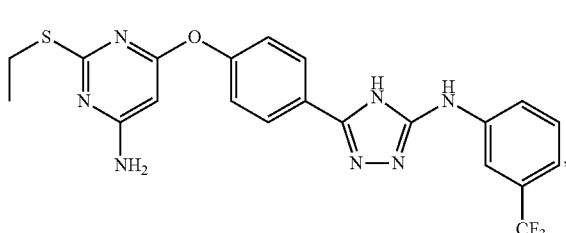
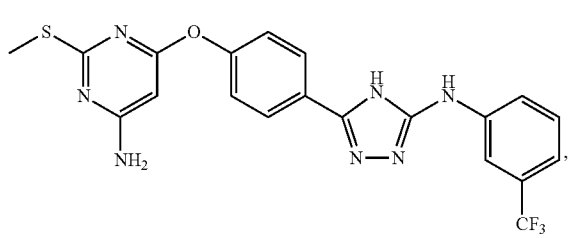
60
-continued
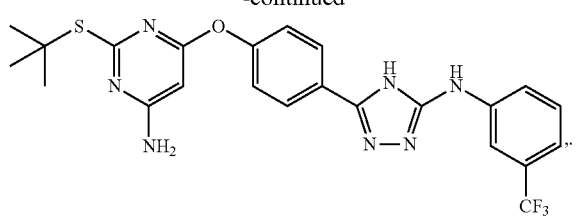
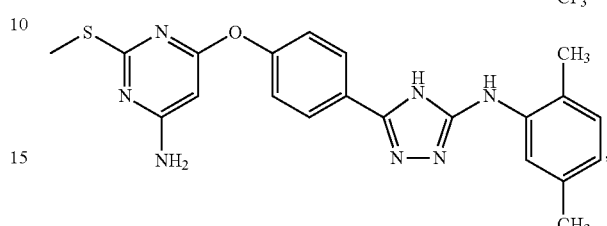
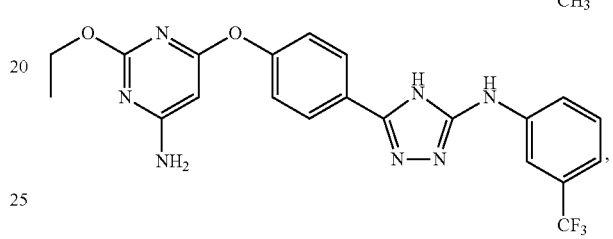
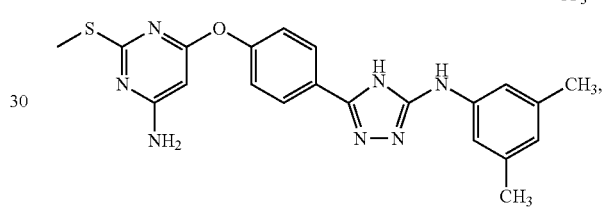
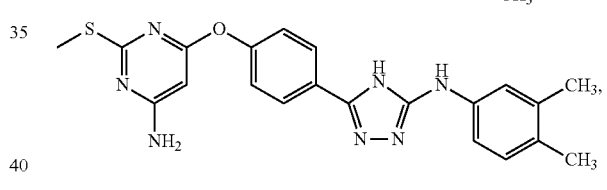
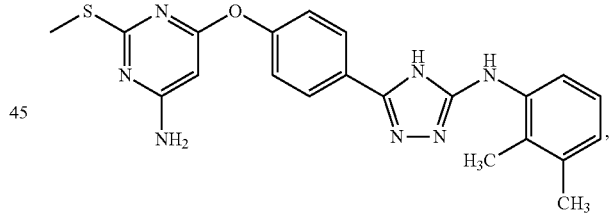
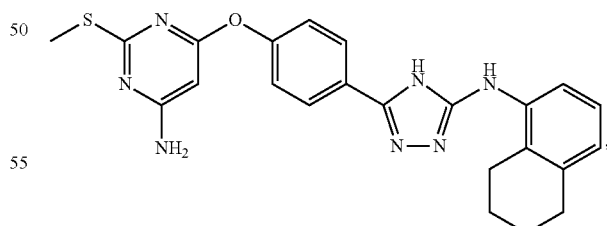
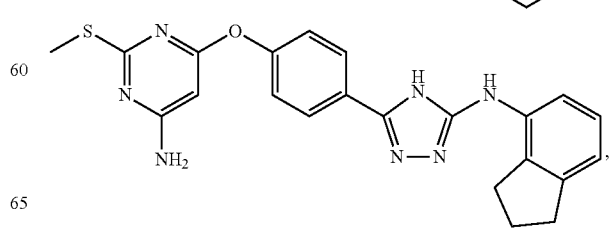

-continued

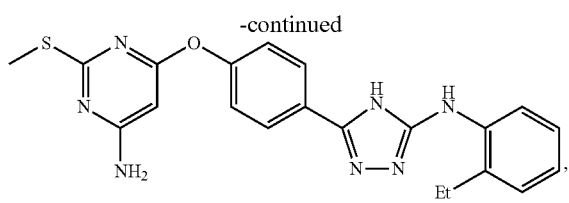

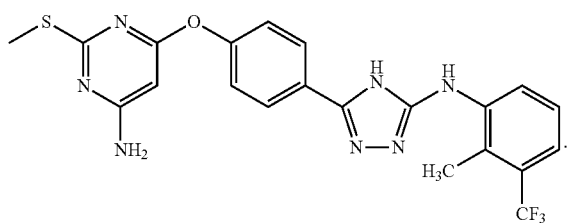

, and

The MAPK/ERK pathway is a signal transduction pathway that couples intracellular responses to the binding of growth factors to cell surface receptors. Receptor-linked tyrosine kinases such as the epidermal growth factor receptor (EGFR) are activated by extracellular ligands. Binding of epidermal growth factor (EGF) to the EGFR activates the tyrosine kinase activity of the cytoplasmic domain of the receptor. The EGFR becomes phosphorylated on tyrosine residues. The basic pathway shown in the figure describes MAPK signaling in cells depending on protein scaffold formation and assembly of complex between B- and C-RAF leading to MEK/ERK activation.

Disruption of B-/C-RAF complex thus inhibits MARK signaling that leads to suppression of angiogenesis. Thus, by employing a compound that (i) stabilizes the protein kinase in the inactive state and (ii) is not an ATP competitive inhibitor of the protein kinase in the active state, inhibition of MEK1/2- and/or ERK1/2-mediated cellular proliferation or migration can be realized.

Treatment of Restenosis

In some embodiments, the present invention provides methods for treating restenosis in a human subject comprising administering to a patient in need a compound that (i) stabilizes a protein kinase in the inactive state and (ii) is not an ATP competitive inhibitor of the protein kinase in the active state. In certain embodiments, the restenosis is intimal hyperplasia-driven restenosis after vascular injury. In some embodiments, the compound for the methods is a selective type II inhibitor of RAF kinase (e.g. B-RAF kinase); more preferably the compound is also a selective type II inhibitor of a PDGF receptor. In some embodiments, the compound modulates A-RAF. In other embodiments, the compound for the methods inhibits the heterodimerization of BRAF with CRAF. In some embodiments, the compound inhibits the phosphorylation of S338 of C-RAF. In another embodiment, the compound does not inhibit active kinases selected from the group B-RAF, C-RAF, VEGFR1, VEGFR2, Flt3, Kit, and PDGFRβ. In some embodiments, the compound is an allosteric inhibitor of PDGFRα, PDGFRβ, Flt3 and/or c-Kit. In some embodiments, the compound has the structure

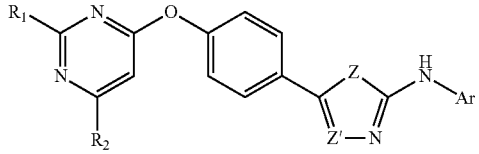

wherein $R_1$ and $R_2$ are independently hydrogen, optional substituted alkyl, halogen, optional substituted amine, $NH_2$, optional substituted alkyoxy, optional substituted thioalkyl, $CF_3S$, optional substituted alkylsulfinyl or optional substituted alkylsulfonyl; Z is NH, S or O; Z' is N or C; and Ar is phenyl or bicyclic phenyl optionally substituted with one or more substituents selected from $C_{1-6}$ alkyl, halogen substi-

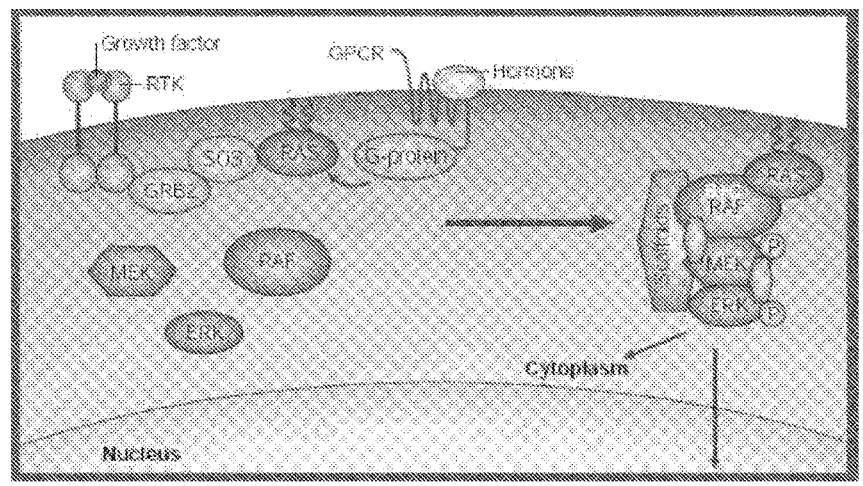

tuted C$_{1-6}$ alkyl, halogen substituted C$_{1-6}$ alkoxy, and C$_{3-10}$cycloalkyl. In certain embodiments, the compound has the structure

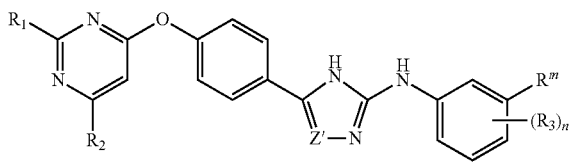

wherein R$^m$ is C$_{1-6}$ alkyl, or halogen substituted C$_{1-6}$ alkyl; and R$_3$ is independently a hydrogen, C$_{1-6}$ alkyl, halogen substituted C$_{1-6}$ alkyl, halogen substituted C$_{1-6}$ alkoxy, or C$_{3-10}$cycloalkyl; or, optionally, R$^m$ and R$_3$ are joined to form a five to seven membered carbocycle; and n is 0-4. In certain embodiments, the compound has the structure

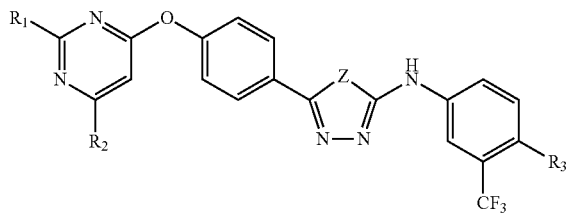

wherein R$_3$ is hydrogen or halogen; and Z is NH, S or O. In another embodiment, the compound is selected from

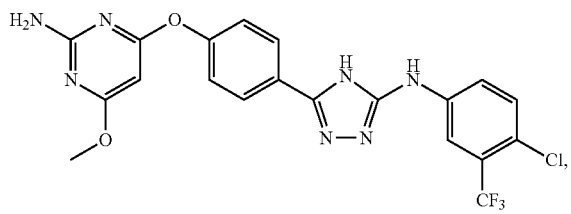

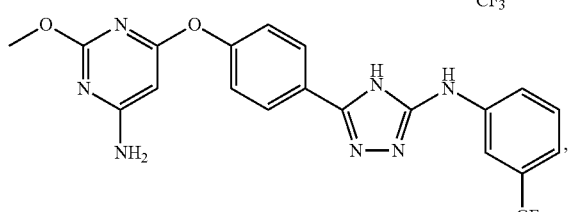

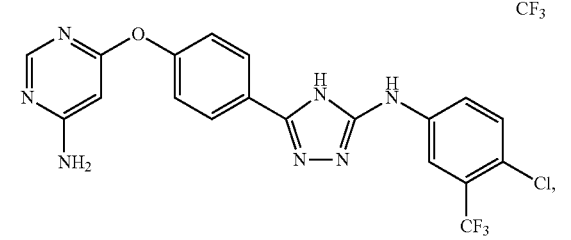

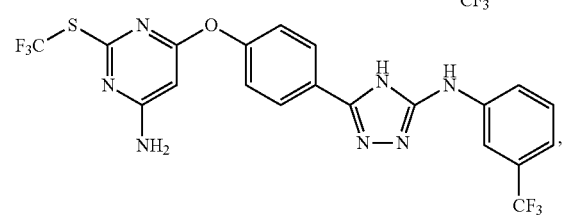

-continued

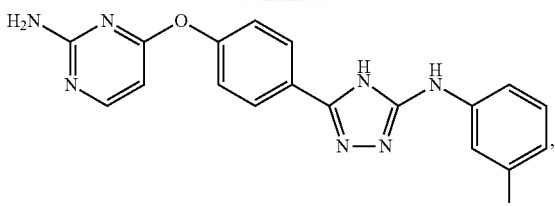

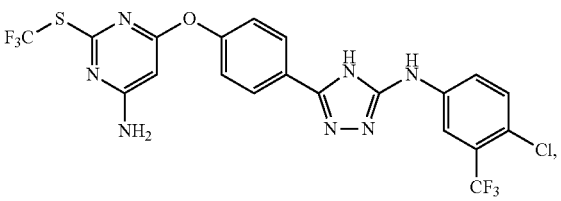

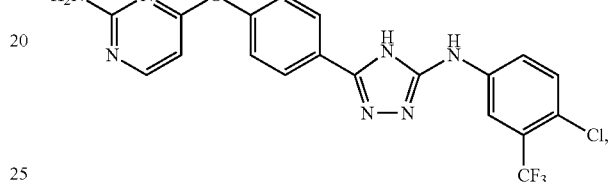

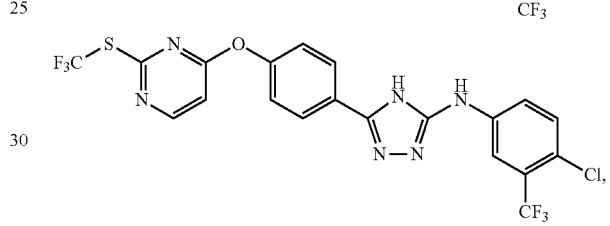

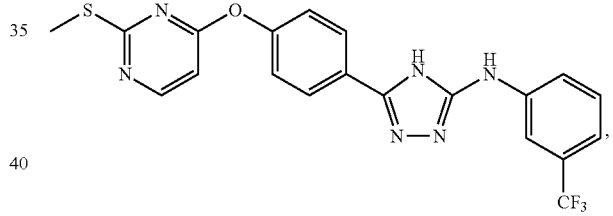

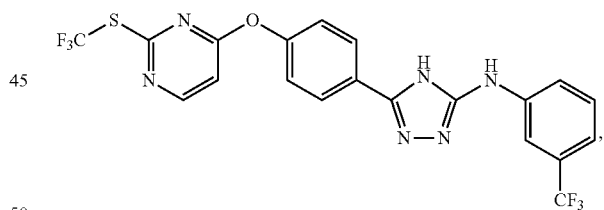

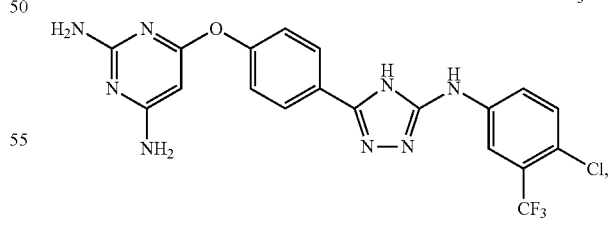

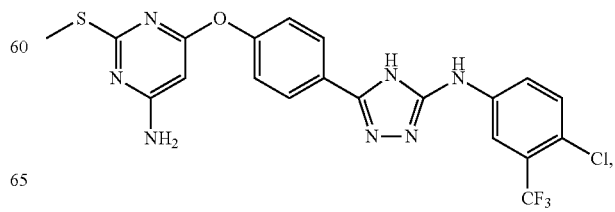

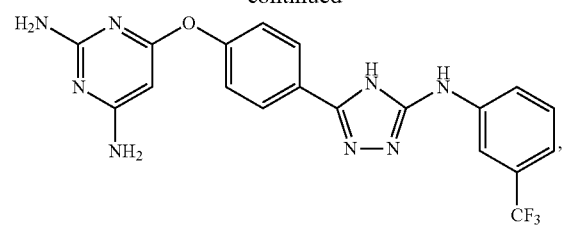
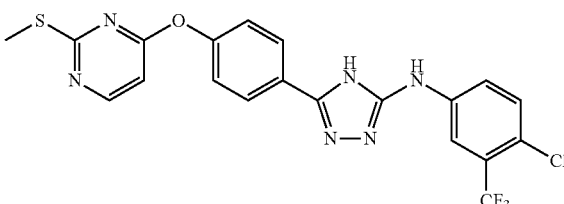
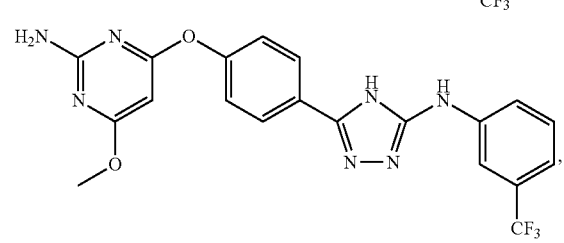
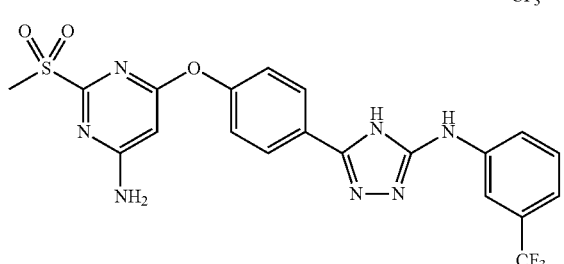
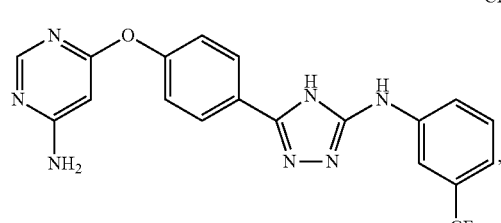
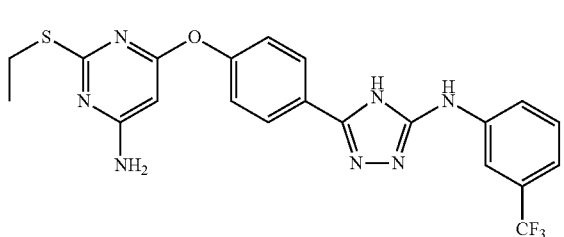
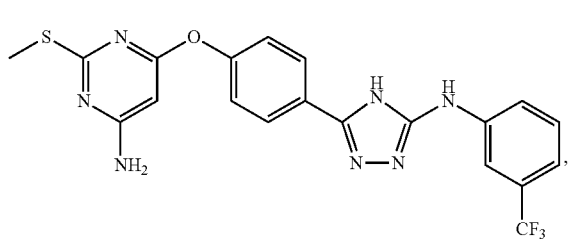
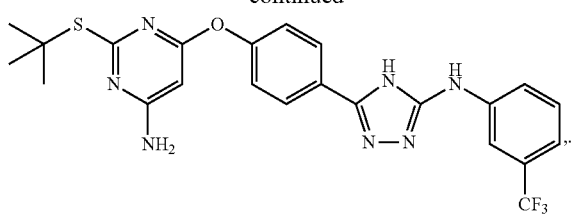
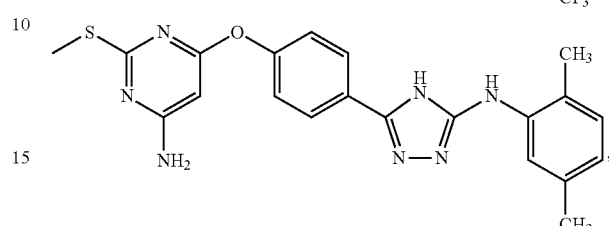
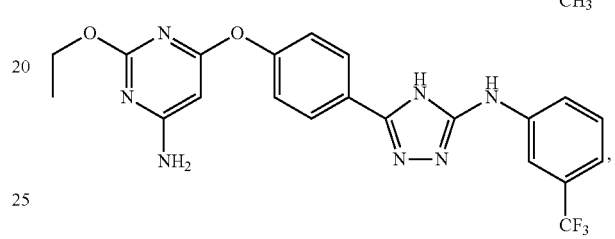
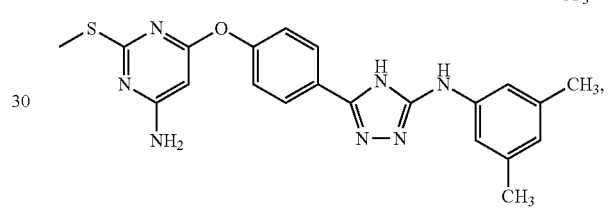
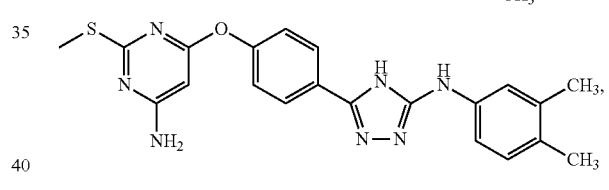
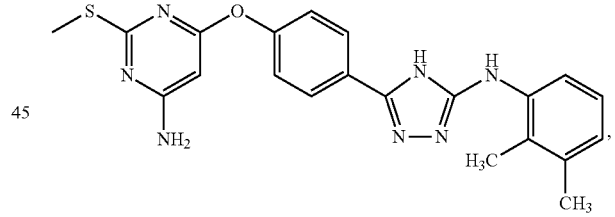
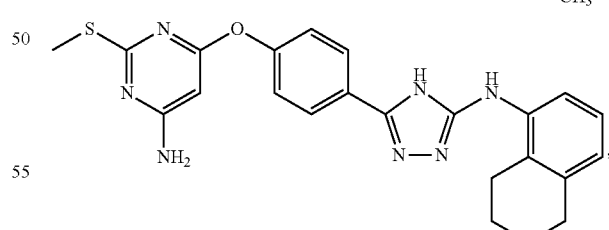
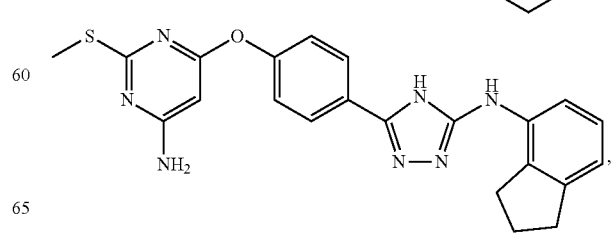

-continued

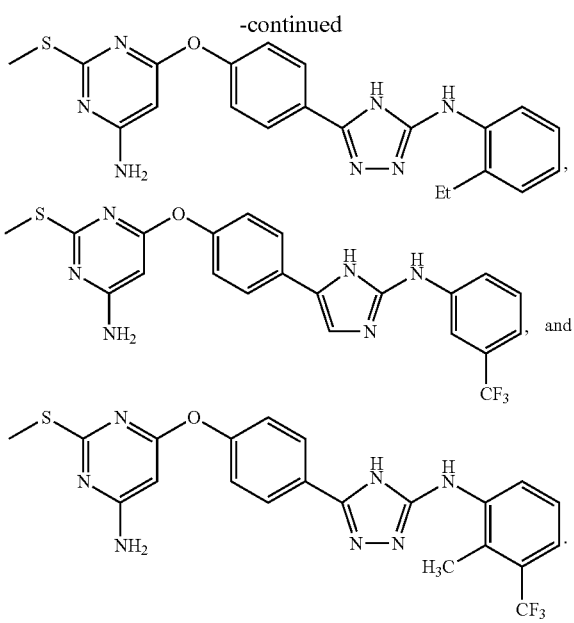

Restenosis literally means the reoccurrence of stenosis, a narrowing of a blood vessel, leading to restricted blood flow. Restenosis usually refers to an artery or other large blood vessel that has become narrowed, received treatment to clear the blockage and subsequently become renarrowed. This is usually restenosis of an artery, or other blood vessel, or possibly a vessel within an organ. Restenosis commonly results from balloon angioplasty and/or stent placement resulting in eventual occlusion of arteries by a process described as neointimal hyperplasia (NIH). After arterial injury, an over-proliferation of vascular smooth muscle cells occurs which has previously been shown to be dependent on both PDGFRα/β (Englesbe, et al. (2004) *J Vasc Surg* 39, 440-6) and MAPK pathway activation (Li, et al. (2005) *Circulation* 111, 1672-8; Pintucci, et al. (2006) *Faseb J* 20, 398-400). Therefore, the combination of PDGFRβ/RAF inhibition would be an ideal treatment for NIH; as such, provided herein compounds that (i) stabilizes a protein kinase in the inactive state and (ii) is not an ATP competitive inhibitor of the protein kinase in the active state which may be selected PDGFRβ/RAF inhibitors. Treatment of Fibrosis Tissue injury initiates a complex series of host wound-healing responses; if successful, these responses restore normal tissue structure and function. If not, these responses can lead to tissue fibrosis and loss of function.

In other embodiments, the methods described here for treating fibrotic diseases in a human subject comprise administering to a patient in need a compound that (i) stabilizes a protein kinase in the inactive state and (ii) is not an ATP competitive inhibitor of the protein kinase in the active state. In certain embodiments, the fibrosis is pulmonary fibrosis. In certain embodiments, the fibrosis is liver fibrosis. In some embodiments, the compound for the methods is a selective type II inhibitor; preferably a selective type II inhibitor of RAF kinase (e.g. B-RAF kinase); more preferably the compound is also a selective type II inhibitor of a PDGF receptor. In some embodiments, the compound for the methods modulates A-RAF. In other embodiments, the compound for the methods inhibits the heterodimerization of BRAF with CRAF. In some embodiments, the compound inhibits the phosphorylation of S338 of C-RAF. In another embodiment, the compound does not inhibit active kinases selected from the group B-RAF, C-RAF, VEGFR1, VEGFR2, Flt3, Kit, and PDGFRβ. In some embodiments, the compound is an allosteric inhibitor of PDGFRα, PDGFRβ, Flt3 and/or c-Kit. In some embodiments, the compound has the structure

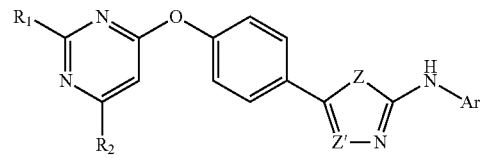

wherein $R_1$ and $R_2$ are independently hydrogen, optional substituted alkyl, halogen, optional substituted amine, $NH_2$, optional substituted alkyoxy, optional substituted thioalkyl, $CF_3S$, optional substituted alkylsulfinyl or optional substituted alkylsulfonyl; Z is NH, S or O; Z' is N or C; and Ar is phenyl or bicyclic phenyl optionally substituted with one or more substituents selected from $C_{1-6}$ alkyl, halogen substituted $C_{1-6}$ alkyl, halogen substituted $C_{1-6}$ alkoxy, and $C_{3-10}$ cycloalkyl. In certain embodiments, the compound has the structure

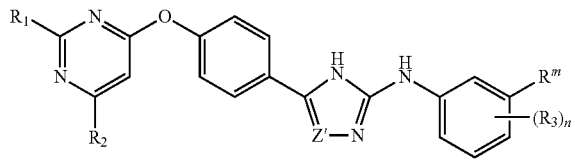

wherein $R^m$ is $C_{1-6}$ alkyl, or halogen substituted $C_{1-6}$ alkyl; and $R_3$ is independently a hydrogen, $C_{1-6}$ alkyl, halogen substituted $C_{1-6}$ alkyl, halogen substituted $C_{1-6}$ alkoxy, or $C_{3-10}$ cycloalkyl; or, optionally, $R^m$ and $R_3$ are joined to form a five to seven membered carbocycle; and n is 0-4. In certain embodiments, the compound has the structure

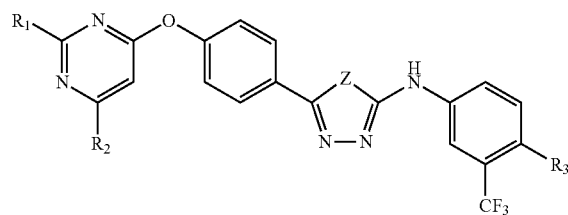

wherein $R_3$ is hydrogen or halogen; and Z is NH, S or O. In another embodiment, the compound is selected from

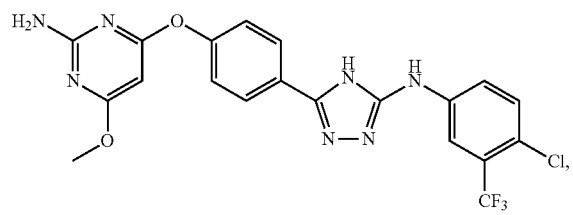

-continued
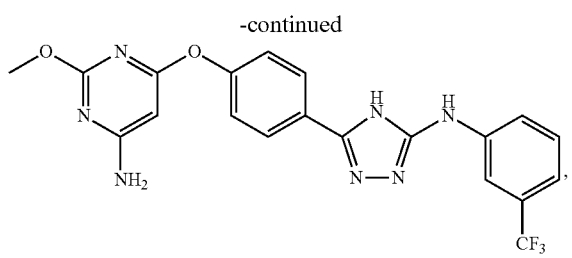
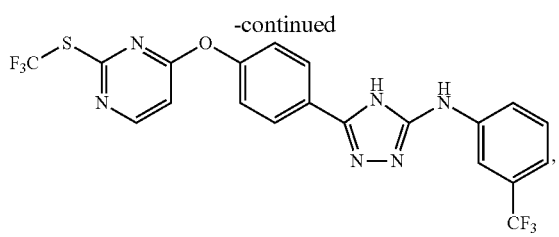
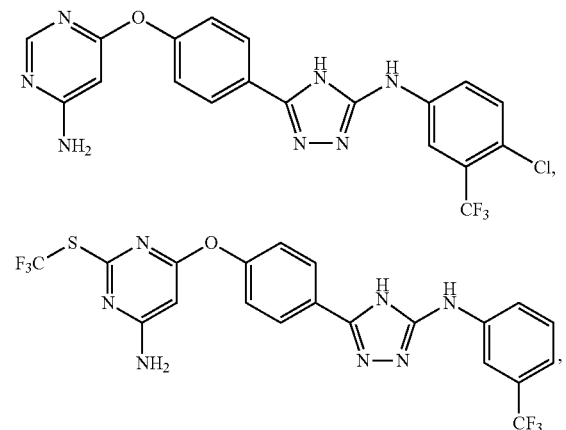
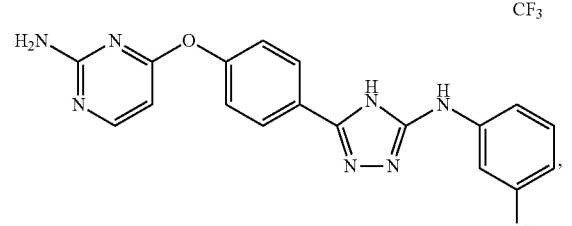
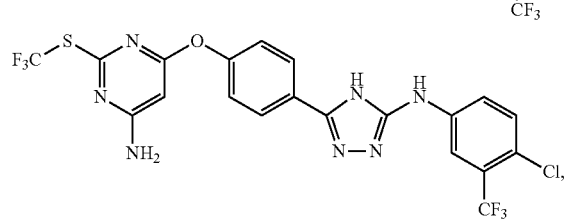
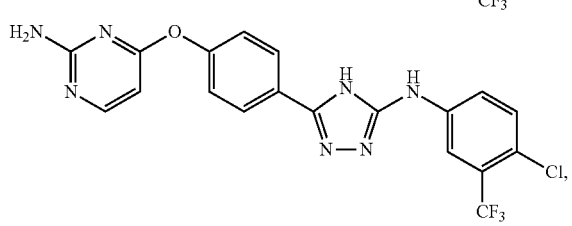
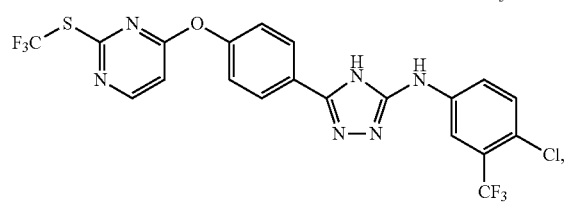
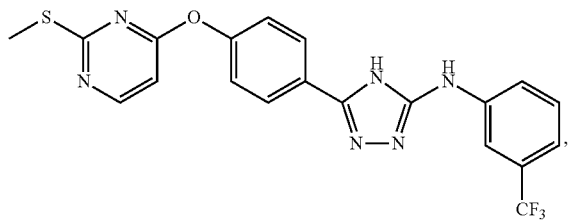
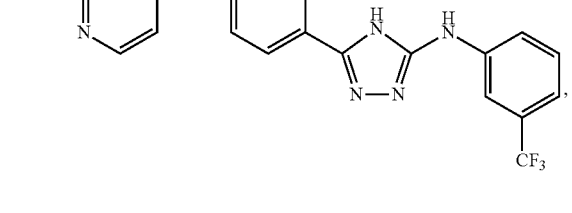

-continued

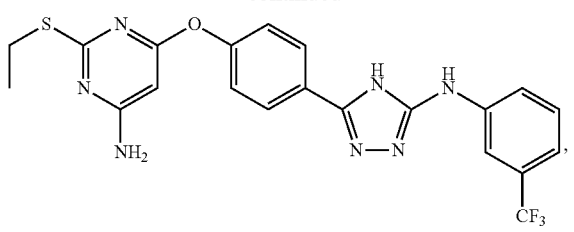

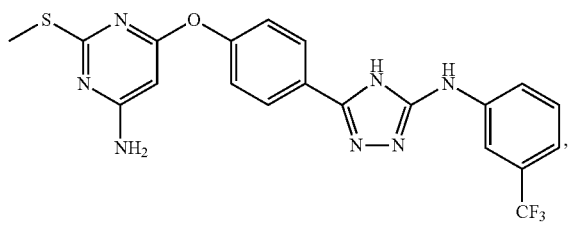

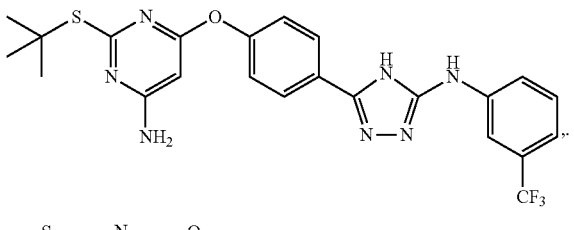

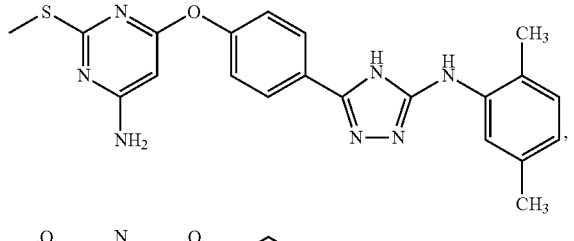

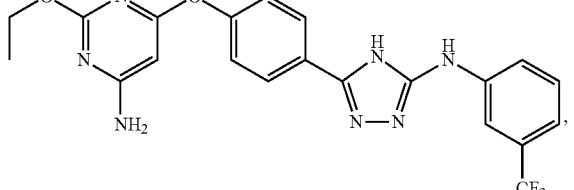

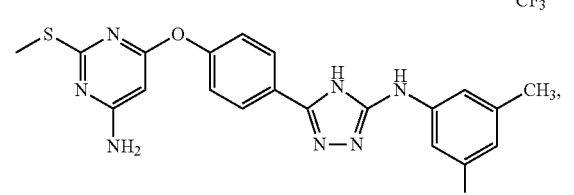

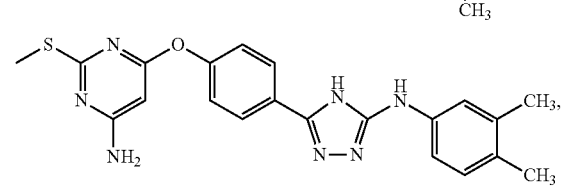

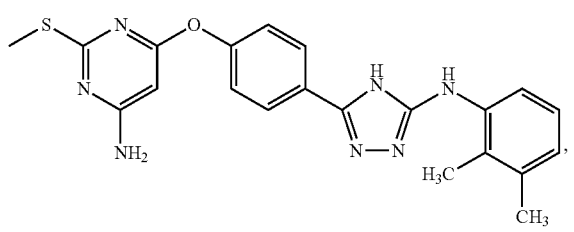

-continued

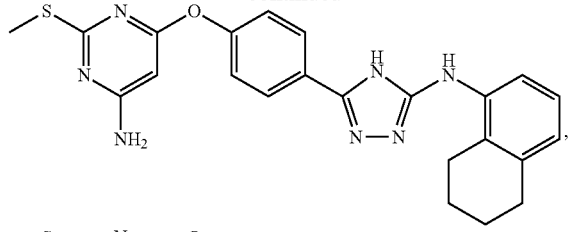

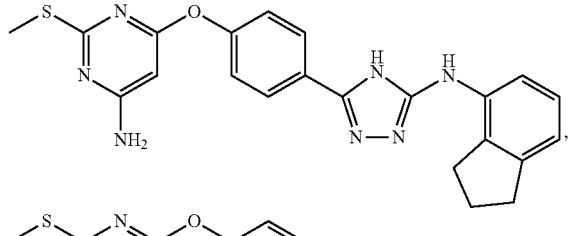

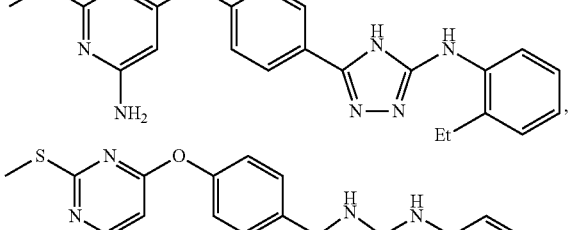

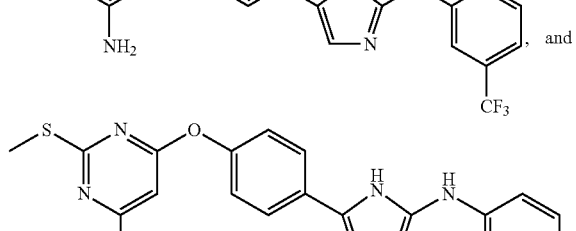, and

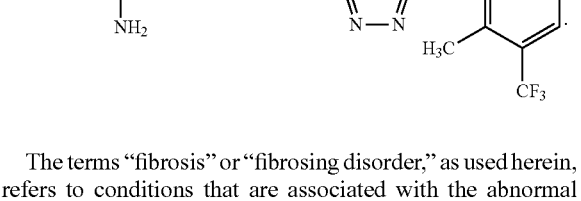.

The terms "fibrosis" or "fibrosing disorder," as used herein, refers to conditions that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract.

Exemplary diseases, disorders, or conditions that involve fibrosis include, but are not limited to: Lung diseases associated with fibrosis, e.g., idiopathic pulmonary fibrosis, pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), scleroderma, chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced); Chronic nephropathies associated with injury/fibrosis (kidney fibrosis), e.g., glomerulonephritis secondary to systemic inflammatory diseases such as lupus and scleroderma, diabetes, glomerular nephritis, focal segmental glomerular sclerosis, IgA nephropathy, hypertension, allograft and Alport; Gut fibrosis, e.g., scleroderma, and radiation induced gut fibrosis; Liver fibrosis, e.g., cirrhosis, alcohol induced liver fibrosis, nonalcoholic steatohepatitis (NASH), biliary duct injury, primary biliary cirrhosis, infection or viral induced liver fibrosis (e.g., chronic HCV infection), and autoimmune hepatitis; Head and neck fibrosis, e.g., radiation induced; Corneal scarring, e.g., LASIK (laser-assisted in situ keratomileusis), corneal transplant, and trabeculectomy; Hypertrophic scarring and keloids, e.g., burn induced or surgical; and Other fibrotic diseases, e.g., sarcoidosis, scleroderma, spinal cord injury/fibrosis, myelofibrosis, vascular restenosis, atherosclerosis, arteriosclerosis, Wegener's granulomatosis, mixed connective tissue disease, and Peyronie's disease.

In one aspect, compounds (i.e., allosteric kinase inhibitors described herein) are administered to a mammal with fibrosis of an organ or tissue or with a predisposition of developing fibrosis of an organ or tissue with one or more other agents that are used to treat fibrosis. In one aspect, the one or more agents include corticosteroids. In one aspect, the one or more agents include immunosuppresants. In one aspect, the one or more agents include B-cell antagonists. In one aspect, the one or more agents include uteroglobin.

Certain Pharmaceutical and Medical Terminology

The term "acceptable" with respect to a formulation, composition or ingredient, as used herein, means having no persistent detrimental effect on the general health of the subject being treated.

The term "antagonist," as used herein, refers to a molecule such as a compound, which diminishes, inhibits, or prevents the action of another molecule or the activity of a receptor site. Antagonists include, but are not limited to, competitive antagonists, non-competitive antagonists, uncompetitive antagonists, partial agonists and inverse agonists.

Competitive antagonists reversibly bind to receptors at the same binding site (active site) as the endogenous ligand or agonist, but without activating the receptor.

Allosteric inhibitors (also known as non-competitive antagonists) bind to a distinctly separate binding site from the agonist, exerting their action to that receptor via the other binding site. Non-competitive antagonists do not compete with agonists for binding. The bound antagonists may result in a decreased affinity of an agonist for that receptor, or alternatively may prevent conformational changes in the receptor required for receptor activation after the agonist binds.

Uncompetitive antagonists differ from non-competitive antagonists in that they require receptor activation by an agonist before they can bind to a separate allosteric binding site.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

The term "carrier," as used herein, refers to relatively non-toxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound (i.e., allosteric kinase inhibitors described herein) and a co-agent, are both administered to a patient simultaneously in the form of a single entity or dosage. The term "non-fixed combination" means that the active ingredients, e.g. a compound (i.e., allosteric kinase inhibitors described herein) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound (i.e., allosteric kinase inhibitors described herein) with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Composition/Formulation

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins1999).

Provided herein are pharmaceutical compositions comprising a compound (i.e., allosteric kinase inhibitors described herein) and a pharmaceutically acceptable diluent(s), excipient(s), or carrier(s). In certain embodiments, the compounds described are administered as pharmaceutical compositions in which a compound (i.e., allosteric kinase inhibitors described herein) is mixed with other active ingredients, as in combination therapy. Encompassed herein are all combinations of actives set forth in the combination therapies section below and throughout this disclosure. In specific embodiments, the pharmaceutical compositions include one or more compounds (i.e., allosteric kinase inhibitors described herein).

A pharmaceutical composition, as used herein, refers to a mixture of a compound (i.e., allosteric kinase inhibitors described herein) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds (i.e., allosteric kinase inhibitors described herein) are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, a compound (i.e., allosteric kinase inhibitors described herein) is formulated in an aqueous solution. In specific embodiments, the aqueous solution is selected from, by way of example only, a physiologically compatible buffer, such as Hank's solution, Ringer's solution, or physiological saline buffer. In other embodiments, a compound (i.e., allosteric kinase inhibitors described herein) is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein, including a compound (i.e., allosteric kinase inhibitors described herein), are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, crosslinked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions of a compound (i.e., allosteric kinase inhibitors described herein) are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In one aspect, compounds (i.e., allosteric kinase inhibitors described herein) are prepared as solutions for parenteral injection as described herein or known in the art and administered with an automatic injector. Automatic injectors, such as those disclosed in U.S. Pat. Nos. 4,031,893, 5,358,489; 5,540,664; 5,665,071, 5,695,472 and WO/2005/087297 (each of which are incorporated herein by reference for such disclosure) are known. In general, all automatic injectors contain a volume of solution that includes a compound (i.e., allosteric kinase inhibitors described herein) to be injected. In general, automatic injectors include a reservoir for holding the solution, which is in fluid communication with a needle for delivering the drug, as well as a mechanism for automatically deploying the needle, inserting the needle into the patient and delivering the dose into the patient. Exemplary injectors provide about 0.3 mL of solution at about a concentration of 0.5 mg to 10 mg of a compound (i.e., allosteric kinase inhibitors described herein) per 1 mL of solution. Each injector is capable of delivering only one dose of the compound.

In still other embodiments, the compounds (i.e., allosteric kinase inhibitors described herein) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds (i.e., allosteric kinase inhibitors described herein) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of a compound (i.e., allosteric kinase inhibitors described herein) is accomplished by means of iontophoretic patches and the like. In certain embodiments, transdermal patches provide controlled delivery of a compound (i.e., allosteric kinase inhibitors described herein). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiment, the transdermal formulations described herein include at least three components: (1) a formulation of a compound (i.e., allosteric kinase inhibitors described herein); (2) a penetration enhancer; and (3) an aqueous adjuvant. In addition, transdermal formulations can include additional components such as, but not limited to, gelling agents, creams and ointment bases, and the like. In some embodiments, the transdermal formulation further include a woven or non-woven backing material to enhance absorption and prevent the removal of the transdermal formulation from the skin. In other embodiments, the transdermal formulations described herein maintain a saturated or supersaturated state to promote diffusion into the skin.

In other embodiments, the compounds (i.e., allosteric kinase inhibitors described herein) are formulated for administration by inhalation. Various forms suitable for administration by inhalation include, but are not limited to, aerosols, mists or powders. Pharmaceutical compositions of a compound (i.e., allosteric kinase inhibitors described herein) are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

Intranasal formulations are known in the art and are described in, for example, U.S. Pat. Nos. 4,476,116, 5,116, 817 and 6,391,452, each of which is specifically incorporated by reference. Formulations, which include a compound (i.e., allosteric kinase inhibitors described herein), which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are found in sources such as REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds described herein, may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

In still other embodiments, the compounds (i.e., allosteric kinase inhibitors described herein) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients is optionally used as suitable and as understood in the art. Pharmaceutical compositions comprising a compound (i.e., allosteric kinase inhibitors described herein) may be manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound (i.e., allosteric kinase inhibitors described herein) described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least compound (i.e., allosteric kinase inhibitors described herein) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, pharmaceutical aqueous suspensions include one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally include solubilizing agents to aid in the solubility of a compound (i.e., allosteric kinase inhibitors described herein). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other pharmaceutical compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other pharmaceutical compositions may include one or more antioxidants to enhance chemical stability where required. Suitable antioxidants include, by way of example only, ascorbic acid and sodium metabisulfite.

In certain embodiments, pharmaceutical aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few hours up to over 24 hours. Depending on the chemical nature and the biological stability of the therapeutic reagent, additional strategies for protein stabilization may be employed.

In certain embodiments, the formulations described herein include one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Assays and Clinical Management

In certain embodiments, provided here are methods for identifying an allosteric inhibitor of RAF kinase comprising contacting a BRAF kinase with a test compound and monitoring the phosphorylation of 5338 of CRAF, wherein a decrease in the phosphorylation of S338 of CRAF relative to non-contacted BRAF kinase indicates that the test compound is an allosteric inhibitor of BRAF kinase. In certain embodiments, the allosteric inhibitor of RAF kinase is a allosteric inihibitor of BRAF kinase.

In certain embodiments, provided here are methods for identifying a therapeutic agent for treating cancer comprising contacting a RAF kinase (e.g. a BRAF) with a test compound and monitoring the phosphorylation of S338 of CRAF, wherein a decrease in the phosphorylation of S338 of CRAF relative to non-contacted BRAF kinase indicates that the test compound is capable of treating cancer.

In some embodiments provided here are methods for monitoring patient pharmacologic response in a chemotherapic treatment comprising monitoring the phosphorylation of S338 of CRAF, wherein a decrease in the phosphorylation of S338 of CRAF relative to non-contacted BRAF kinase indicates that the chemoehtrapic treatment has positive pharmacologic response.

In some embodiments provide uses of pS338-CRAF as a predictive biomarker for clinical management of a cancer treatment. In certain embodiments, a decrease in the phosphorylation of S338 of CRAF relative to non-contacted RAF kinase indicates a likelihood of benefit from said cancer treatment. Biomarkers can be pre-treatment measurements used to characterize the patient's disease state in order to determine whether the patient is a good candidate for certain treatments. These biomarkers are called predictive biomarkers. As shown in the disclosure here, the phosphorylation of S338 of CRAF relative to non-contacted RAF kinase correlate to cancer proliferation. RAF ATP-mimetics induce RAF pS338-CRAF and thus induce RAF dimer formation in cancer cells. Use of pS338-CRAF as a predictive biomarker thus can provide clinical cancer treament mangagement.

Type II inhibitors represent a new paradigm for drug selection as seen with the co-crystal structures of Abl with imatinib (1) and B-RAF with sorafenib (2). The approach of stabilizing the inactive kinase conformation has led to the development of novel inhibitors which stabilize the DFG-out conformation (Liu, et al. (2006) Nature chemical biology 2:358-364, Okram, et al. (2006) Chemistry & biology 13:779-786). As discussed before, mutation of the Raf-1 activation domain (SS338/9AA) not only prevents Raf-1/ASK1 complex formation but also abolishes bFGF-mediated EC protection from genotoxic stress. Thus, by contacting a BRAF kinase with a test compound and monitoring the phosphorylation of S338 of CRAF, wherein a decrease in the phosphorylation of S338 of CRAF relative to non-contacted BRAF kinase would indicate that the test compound is an allosteric inhibitor of BRAF kinase.

EXAMPLES

Animal studies. All animal procedures were conducted in accordance with all appropriate regulatory standards under protocols #SO5018 and #SO6008 approved by the University of California, San Diego Institutional Animal Care and Use Committee.

Computational docking studies and chemical synthesis. The molecular modeling and homology model of PDGFRβ are described as follows. All compounds were synthesized from commercially available starting materials and schemes, synthetic procedures, and purification details are available as follows.

The x-ray crystal structure of B-RAF with BAY43-9006 (sorafenib) was selected for docking studies since it contained the DFG motif of the activation loop in a desirable inactive state (i.e. DFG-out). Moreover this inactive state is stabilized by a small molecule and as a result provides an appropriate ligand-induced conformation for docking with 6. The Docking module of Insightll (Accelrys, San Diego, Calif.) was used to perform ligand docking studies with the previously reported co-crystal structure of B-RAF with BAY 43-9006 (sorafenib). This inactive conformation was chosen since stabilizing the DFG out structure is important for the type II kinase inhibition mode. As a measure of docking accuracy the ligand from the crystal structure, BAY43-9006, was removed and docking from a 2D structure of this molecule was performed and qualitatively interpreted. The homology model of the PDGFRβ kinase module was created based on the crystal structure of VEGFR2 (pdb ID 1Y6B). VEGFR2 and PDGFRβ share 46% sequence identity within the kinase domain. Homology modeling was performed using the Homology module of the Insightll program (Accelrys, San Diego, Calif.). The model underwent 10,000 iteration molecular mechanics minimization with the program Discover (Accelrys, San Diego, Calif.) after its construction. The docking of compound 6 to this structure was performed as described above.

Immunoprecipitation and Immunoblotting.

Following stimulation with bFGF, VEGFA or PDGF-BB, cells were washed 1× with ice-cold PBS and lysed in RIPA buffer. For the PDGFRβ autophosphorylation assay in VSMCs, 500 μg of protein from lysates was incubated with 3 μg of anti-PDGFRβ (sc-432, Santa Cruz Biotechnology) for 1 h at 4° C. and subsequently tumbled overnight with protein A/G beads (Pierce) for immunoprecipitation. For the MAPK assay in HUVECs, standard SDS-PAGE and immunoblotting was performed using antibodies to phospho-MEK S217/S221, phospho-MEK S298, phospho-ERK T202/Y204, phospho-C-RAF S259 and S338 (all from Cell Signaling, Danvers, Mass.), MEK1 (Santa Cruz), ERK2 (SC), and C-RAF(SC). For the PDGFRβ autophosphorylation assay, antibodies to PDGFRβ (sc-339, SC) and HRP-conjugated PY-20 (sc-508, SC) were used to detect total PDGFRβ and phospho-tyrosine levels, respectively. HRP conjugated primary or secondary Abs were detected with SuperSignal ECL (Pierce).

Cell Viability Assays

For XTT assays, cells were grown in 96-well plates overnight and all assays were conducted in growth medium will full serum and additives. Compounds were serially diluted in DMSO and then further diluted into the medium to give the appropriate concentration while minimizing precipitation associated with serial diluting in medium alone Inhibitors were added for 72 h and cell viability was quantified at 450 nm after the addition of 1 mg/ml XTT solution (Sigma-Aldrich) in phenol-red free DMEM medium containing phenoxymethosulfate (Sigma-Aldrich).ABs Dose-response curves were plotted using GraphPad Prism software and $EC_{50}$s were calculated using this program.

Stellate Cell/Endothelial Cell Co-Culture Assay for Endothelial Tube Formation.

Early passage (p<5) human Telomerase Reverse Transcriptase-hepatic stellate cells (Stellate cells), a generous gift from Dr. David Brenner, were labeled with 10 μg/ml red fluorescent dye DiIC(3) (BD Biosciences) for 2 h at 37° C. The stellate cells were washed in PBS and mixed with early passage HUVECs (p<5) at a ratio of 1:4 and mixed into a 3.75 mg/ml Type 1 Rat tail collagen matrix (BD Biosciences) in M-199 media. 30 μl of this mixture was seeded onto each well of a half-area 96 well plate (Corning). The collagen was allowed to polymerize for 30 min at 37° C. and 100 μA of complete EBM-2 media was added to each well. Various inhibitors were serially diluted in DMSO and subsequently added to duplicate wells 6 h post cell seeding. The endothelial tubes were stained at 24 h by adding 2 μl FITC labeled *Ulex europaeus* lectin (Vector labs) per well. The endothelial tubes and the stellate cells were imaged at 48 h with a 10× objective on a confocal microscope. Images were collected across five fields per well. Tube lengths were measured using Metamorph software for each tube for all 10 microscopic fields from the duplicate wells. The % pericyte-covered tube length was calculated from the ratio of tube length sums for the tubes with and without pericyte contact.

Mouse Matrigel™ Model of Angiogenesis

Female Nu/Nu mice were implanted with growth-factor depleted Matrigel (BD Biosciences, San Jose, Calif.) in the flank containing either PBS or 200 ng of bFGF (Peprotech). The following morning mice were treated with 6, control compound, or vehicle (10% HS-15 in 3.3% Dextrose) by intraperitoneal injection on a bid dosing schedule. Five days after matrigel implantation, mice were tail-vein injected with FITC-lectin and plugs were harvested and imaged by confocal microscopy and quantified after homogenization in ice-cold PBS using a fluorescent microplate reader (Tecan Systems, Inc., San Jose, Calif.).

For immunohistochemistry, mice were implanted with matrigel plugs with the same dosing schedule described above. On day 5, the plugs were excised and 5 lam sections were generated. The sections were fixed according to the Apoptag protocol in which immunostaining was added during the TUNEL staining process as well as TO-PRO3 (Invitrogen, Carlsbad, Calif.) for a nuclear counterstain. The sections were labeled with anti phospho-ERK T202/Y204 (Cell Signaling) and an endothelial cell mix consisting of anti-CD31, anti-Flk, anti-VE-Cadherin (all from BD Biosciences, San Jose, Calif.), and anti-endoglin (Millipore). Primary antibodies were added at 1:100 dilutions and the corresponding secondary anti-Rat Ab was added at a 1:250 dilution. The tri-color images were generated with confocal microscopy.

Orthotopic Pancreatic Carcinoma Model

Orthotopic human pancreatic cancer xenografts from the pancreatic cancer cell line XPA1-RFP were established in nude mice by surgical orthotopic implantation (SOI). Briefly, subcutaneous XPA1-RFP tumors in the exponential growth phase were harvested and sectioned into 1 mm$^3$ pieces in serum-free RPMI medium. Mice were anesthetized using 50% ketamine, 38% xylazine and 12% agepromazine maleate injected intramuscularly at a dose of 2 µl/g, and their abdominal wall was sterilized with alcohol. A small incision was then made in the right pararectal line through the skin and peritoneum. The body of the pancreas was exposed and a 1 mm$^3$ tumor fragment was sutured to the pancreas using a single 8-0 nylon surgical suture (Davis-Geck, Inc. Manati, Puerto Rico). The pancreas was then returned to the abdomen and the peritoneum and skin were closed in two layers using 6-0 vicryl surgical suture.

At day 3 after SOI the animals began treatment with twice-daily IP injections of either compound, 6 (50 mg/kg dose in 200 µl total volume), or vehicle control at 12 hour intervals. The animals were weighed and imaged every 3 days starting at day 3 post-SOI using the Olympus OV100 Small Animal Imaging System (Olympus Corp. Tokyo, Japan), containing an MT-20 light source (Olympus Biosystems Planegg, Germany) and DP70 CCD camera (Olympus Corp. Tokyo, Japan). All images were processed for contrast and brightness with the use of Photoshop element −4. All measurements were made using Image-J software. At day 12 post-SOI the animals were sacrificed and their tumors were excised, weighed, and measured in 3 dimensions in order to calculate tumor volume. The tumor volume was calculated with the formula: volume=height×width×length×0.52. Ex-vivo tumors were then compressed and imaged using the OV100. The total vessel length for each tumor was measured using Image-J software and converted to vessel density by dividing total tumor vessel length by tumor volume.

Orthotopic Renal Cell Carcinoma Model.

Male Nu/Nu mice were anesthetized with an intraperitoneal injection of 50 mg/kg ketamine and 10 mg/kg medetomidine. A small incision was made along the left flank of the mice and the kidney was exposed. A 27-gauge insulin syringe was used for orthotopic injection of the SN12C-RFP cells. One million tumor cells in 20 µl of a 1:1 PBS:Matrigel mixture were injected into the lower pole of the kidney just below the renal subcapsule. The needle was removed after a visible blister formed and leakage of the tumor cell suspension was minimal. The abdominal wall was closed by suturing the peritoneal membrane followed by stapling the dermal layer. Animals which formed visible blisters upon injection in the subcapsule with minimal leakage were used for the efficacy study. Male Nu/Nu mice with orthotopic injections of the SN12C-RFP cells were imaged using the Olympus OV100 Small Animal Imaging System and grouped on day 7 based on weight and imaging results. The mice were dosed orally at 100 mg/kg daily with 6 in 10% HS-15 and 3.3% dextrose. At the end of the study, the kidney tumors were imaged with the OV-100 system for RFP expression and then the kidneys were resected and weighed. The difference in weight between the tumor bearing kidney and the normal kidney was reported.

Synthesis and Characterization of New Compounds

General Synthetic Methods

Unless otherwise noted, materials were obtained from commercial suppliers and were used without purification. Removal of solvent in vacuo refers to distillation using a Biichi R-200 rotary evaporator and a Welch 2025 vacuum pump. All microwave irradiation experiments were carried out in Initiator™ (Biotage) microwave apparatus in the standard configuration including the proprietary Biotage software. The reactions were carried out in 5 mL Emrys™ microwave vials. After the irradiation period, the reaction vessel was cooled rapidly (1-2 min) to ambient temperature by gas jet cooling.

$^1$H and $^{13}$C NMR spectra were recorded on Bruker AMX-II (500 MHz) spectrometer. Proton resonances are reported in parts per million (ppm) downfield from tetramethylsilane (TMS). $^1$H NMR data are reported as multiplicity (s singlet, d doublet, t triplet, q quartet, dd doublet of doublets, dt doublet of triplets, br s broad singlet), coupling constant in Hertz and number of protons. The $^1$H and $^{13}$C NMR spectra were obtained in DMSO-d$_6$ (99.96 DMSO-d$_6$ with 0.03 v/v TMS). The $^1$H NMR spectra for 1,2,4-triazoles were recorded at 80° C. to induce the rapid exchange of the N-proton of the triazole ring. Due to the intermediate-to-slow exchange of the N-proton of the triazole ring at room temperature the broadening of the peaks is observed in both $^1$H and $^{13}$C NMR spectra recorded at ambient temperature. All data were processed with Xwin-NMR software.

High pressure liquid chromatography was achieved using Gilson Unipoint 215 Liquid Handler with 151 UV/Vis detector and Waters PrepLC™ 40 mm Module with Symmetry-Shield™ RP18 7 um 40×100 mm PrepPak® cartridges. Purification of compounds by high pressure liquid chromatography was performed at 40 mL/min flow rate with a gradient from 10% of solvent B (acetonitrile with 0.1% TFA) in solvent A (water with 0.1% TFA) to 100% solvent B in 25 min, followed by 5 min elution with 100% solvent B. Analytical thin-layer chromatography (TLC) was performed on commercial silica plates (EMD Chemicals, Silica gel 60 F254, 0.25 mm thickness). Compounds were visualized by UV light (254 nm). Flash chromatography was performed either by CombiFlash® (Companion®, Teledyne ISCO) or using silica gel (ICN silica 32-63 D 60 Å). Waters 2795 LC/MS with Micromass® ZQ™ and 2996 PDA detector were used to monitor the progress of reactions and check the purity of products. Mass spectra were obtained in electrospray ionization (ESI) positive mode. Accurate masses were measured by electrospray ionization (ESI) time-of-flight (TOF) reflectron experiments performed on an Agilent ESI-TOF mass spectrometer. Samples were electrosprayed into the TOF reflectron analyzer at an ESI voltage of 4000 V and a flow rate of 200 microliters/minute.

In vitro kinase screen and competitive binding assay. Sorafenib as well as test compounds were submitted to Invitrogen and screened using their SelectScreen™ Profiling Service. For the competitive binding assay, test compounds were screened at 10 µM against 70 diverse kinase targets for competitive binding using the KINOMEscan™ technology (Ambit Biosciences) (Karaman, et al. (2008) *Nature biotechnology* 26:127-132). 11-point Kd curves were determined for hits identified during the initial screen.

Cell culture and cell based screening. HUVECs and VSMCs (Lonza, Basel, Switzerland) were maintained as recommended with all experiments conducted at passage <6. XPA1-RFP and SN12C-RFP cells were maintained under standard culture conditions in RPMI supplemented with 10% FBS. XPA-1 cells were a gift from Dr Anirban Maitra at Johns Hopkins University and transduced with retrovirus to establish stable RFP-expressing cells as described previously (Tsuji, et al. (2006) Jop 7:193-199). For cell-based assays, sub-confluent cells were starved overnight in serum-free medium, pretreated with inhibitor and stimulated with growth factor as described in the Figure Legend. A description of the immunoprecipitation, immunoblotting, and antibodies is disclosed herein.

Zebrafish studies. Transgenic Tg(fli1:EGFP) zebrafish embryos were purchased from www.zfin.org and reported elsewhere (Lawson, et al. (2002) *Dev Biol* 248:307-318) and maintained according to ("Zebrafish—A Practical Approach", Oxford University Press, 2002). Compounds in DMSO stock solutions were diluted directly into the water and vessels were imaged for GFP expression using a Nikon c1-si confocal microscope. Apoptosis was measured by TUNEL staining using the Apoptag in situ Red Fluorescence Kit (Chemicon) with a protocol described previously (Stanton, et al. (2006) The Journal of biological chemistry 281: 28782-28793).

Stellate cell/endothelial cell tube formation assay and mouse matrigel model. This assay was performed as described in the SI Methods. The stellate cells were a gift from Dr. David Brenner and previously described (Schnabl, et al. (2002) *Laboratory investigation; a journal of technical methods and pathology* 82:323-333). The 3D-collagen assay for tube formation was performed as previously described (Koh, et al. (2008) *Methods in enzymology* 443:83-101). The mouse matrigel model was performed as previously described (Eliceiri, et al. (1999) *Molecular cell* 4:915-924 5) and further details of immunohistochemistry and animal dosing can be found herein.

Orthotopic pancreatic carcinoma and renal cell carcinoma models. Six-week old male Nestin-GFP nude mice described previously (Amoh, et al. (2005) *Cancer research* 65:5352-5357; Amoh, et al. (2006) *J Surg Res* 132:164-169) underwent surgical orthotopic implantation of XPA-1-RFP pancreatic tumor cells as described previously (Katz, et al. (2003) *Cancer research* 63:5521-5525, 39; Bouvet, et al. (2002) *Cancer research* 62:1534-1540) and in further detail disclosed herein. The renal cell carcinoma model was used as previously described (An, et al. (1999) *Clin Exp Metastasis* 17:265-270) and is described in further detail herein.

Statistical calculations. All statistical evaluation was done using NCSS 2007 statistical software (Kaysville, Utah). For comparisons between two groups a two-tailed t-test was used for data with equal variance and the Aspin-Welch Unequal Variance Test was used for data with unequal variance. For comparison between more than two groups a One-way ANOVA was used. P-values are noted in the figure legends.

Example 1

Preparation of Triazole Compound 6

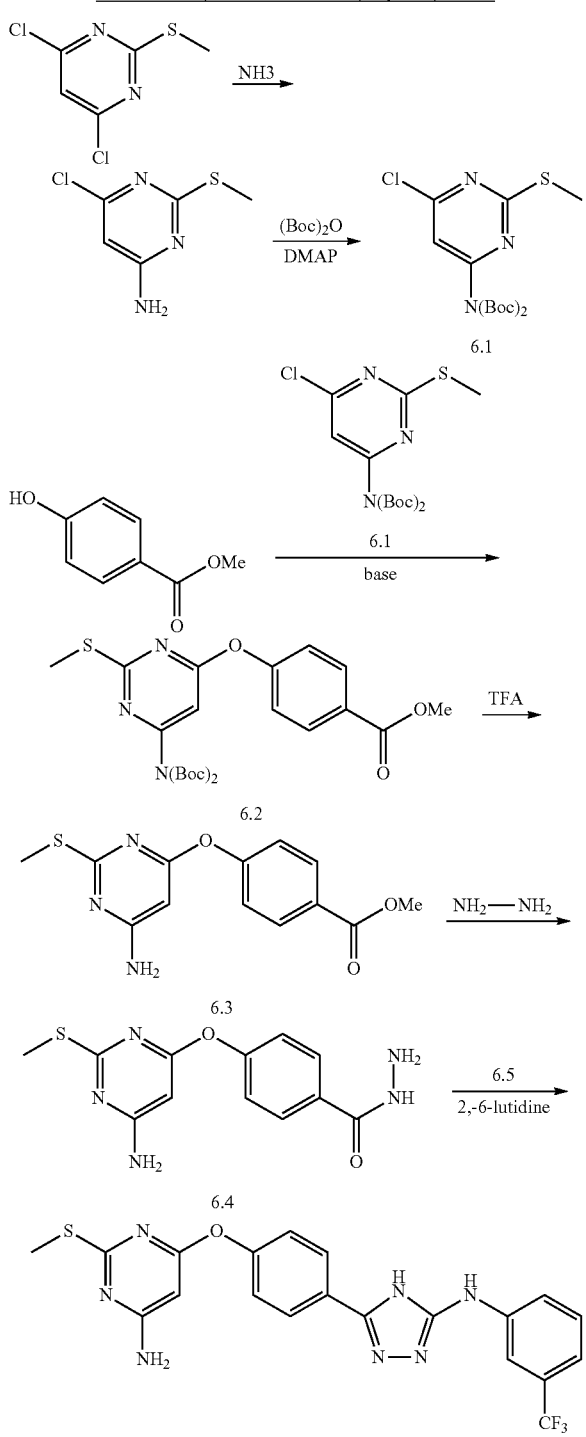

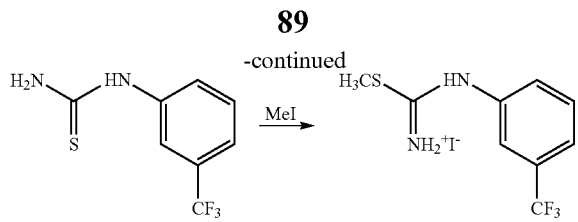

Compound 6 was prepared from commercially available 4,6-dichloro-2-(methylthio)pyrimidine followed scheme 4. To prepare compound 6.1,4,6-Dichloro-2-(methylthio)pyrimidine was reacted with ammonia in THF in a sealed tube to provide 4-Amino-6-chloro-2-(methylthio)pyrimidine in good yield. Amino group of the resulting compound was protected with suitable protecting group such as BOC to afford compound 6.1. Compound 6.1 was then reacted with methyl 4-hydroxybenzoate in the presence of base to provide the amine protected intermediate, 2 which upon deprotection under acidic condition to afford methyl 4-(6-amino-2-(methylthio)pyrimidin-4-yloxy)benzoate (3). Reaction of compound 3 with hydrazine hydrate in methanol provided 4-(6-amino-2-(methylthio)pyrimidin-4-yloxy)benzohydrazide (6.4) in good yield. The hydrazide was then reacted with S-methyl N-[3-(trifluoromethyl-phenyl)thiourea in the presence of base to yield compound 6.

Example 1-1

Preparation of 4-Amino-6-chloro-2-(methylthio)pyrimidine

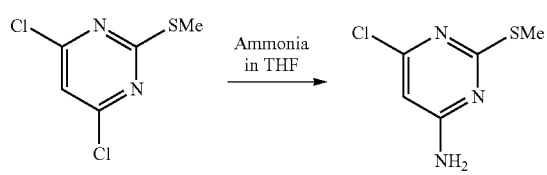 [SMILES: CSc1nc(Cl)cc(Cl)n1 ; CSc1nc(N)cc(Cl)n1]

Reagents:

| Raw materials | Quantity | M. | Moles | Eq. |
|---|---|---|---|---|
| 4,6-dichloro-2-(methylthio)pyrimidine | 400 g | 195 | 2.05 | 1.0 |
| Ammonia in THF(16% Assay) | 4.0 L | — | — | 10 Vol |
| Hexane Lot-1 | 400 mL | — | — | 2 Vol |
| Hexane Lot-2 | 400 mL | — | — | 2 Vol |
| Water | 2 × 400 mL | — | — | 2 Vol |

Experimental Procedure:
Take ammonia in THF into a 2 L autoclave and add 4,6-dichloro-2-(Methylthio) pyrimidine slowly.
Heat the reaction mixture to 50-60° C. and maintain the reaction at 50-60° C. for 3-4 hours (Inbuilt pressure 7-8 Kg/cm$^2$).
Check the progress of the reaction by TLC. Upon completion, the reaction was brought to 25-35° C.
Concentrate the reaction mixture under vacuum.
Charge Hexane and stir for 30-45 minutes at 25-35° C.
Filter the solid and wash the solid with Hexane.
Wash the solid with water (2×400 mL).
Dry the solid at 25-35° C. till M. C reaches to less than 2%.

Yield 352.0 g
% of Yield: 97.77%.
Purity by HPLC: 99.07%.
Other suitable conditions such as ammonia in MeOH or dioxane could be used accordingly when different analogs are used.

Example 1-2

Preparation of 4-Amino-6-chloro-2-(methylthio)pyrimidine, 6.1

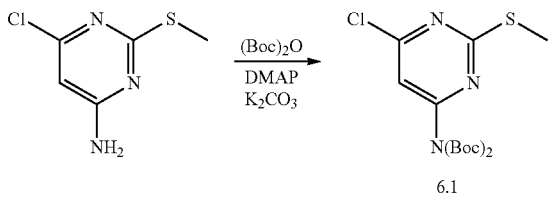

Reagents:

| Raw materials | Quantity | M.W. | Moles | Equiv |
|---|---|---|---|---|
| 4-Amino-6-chloro-2-(methylthio)pyrimidine | 300 g | 175.5 | 1.7 | 1.0 |
| THF | 1.5 L | — | — | 5 Vol |
| K$_2$CO$_3$ | 519.76 g | 138.21 | 3.7 | 2.2 |
| Boc anhydride | 31.0 g | 218 | 4.2 | 2.5 |
| DMAP | 20.85 g | 122 | 0.17 | 0.1 |
| Ethyl acetate Lot-1 | 900 mL | — | — | 3 Vol |
| Water | 750 mL | — | — | — |
| Saturated Sodium chloride solution | 900 mL | — | — | 3 Vol |
| Sodium sulphate | 50 g | — | — | — |
| Ethyl acetate Lot-2 | 300 mL | — | — | — |

Experimental Procedure
Charge 4-Amino-6-chloro-2-(methylthio)pyrimidine and THF into a clean and dry round bottom flask at 25-35° C.
Add K$_2$CO$_3$ lot wise at 25-35° C. in 5-10 minutes.
Add Boc anhydride slowly at 25-35° C. in 15-30 minutes.
Stir at 25-35° C. for 15-30 minutes.
Add DMAP slowly in 5-10 minutes at 25-35° C.
Maintain the reaction mass at 25-35° C. for 1-2 hours.
Check the progress of reaction by TLC.
Upon completion, charge ethyl acetate and water.
Stir the reaction mass at 25-35° C. for 10-15 minutes.
Separate the aqueous layer and organic layer.
Wash the organic layer with saturated sodium chloride solution.
Dry the organic layer over sodium sulphate
Filter sodium sulphate out
Wash the sodium sulphate with Ethyl acetate.
Concentrate the organic layer completely under vacuum.
Yield: 632 g
% of Yield: 98.46.
Purity by HPLC: 77.98% Di-Boc compound.
11.49% Mono Boc compound.

Alternatively, compound 6.1 can be prepared by addition of (BOC)₂NH anion to the corresponding 4,6-dichloropyrimidine or other suitable methods known in the art.

Example 1-3

Preparation of Compound 2

Reagents:

| Raw materials | Quantity | M. Wt | Moles | Equiv |
|---|---|---|---|---|
| Compound 6.1 | 650 g | 375.5 | 1.7 | 1.0 |
| DMF | 1.95 L | — | — | — |
| Methyl hydroxyl benzoate | 266.42 | 152.15 | 1.9 | 1.01 |
| 1,4-diazabicyclo[2.2.2]octane | 235 mL | 112.18 | 2.0 | 1.2 |
| Water Lot-1 | 6.5 L | — | — | 10 Vol |
| Water Lot-2 | 1.3 L | — | — | — |

Experimental Procedures:

Charge compound 6.1 into a clean and dry RB flask at 25-35° C.

Charge DMF into RB flask at 25-35° C.

Charge Methyl hydroxyl benzoate at 25-35° C.

Charge 1,4-diazabicyclo[2.2.2]octane (DABCO) into RB Flask at 25-35° C.

Stir the reaction mass at 25-35° C.

Check the progress of the reaction by TLC.

IF TLC complies add water Lot-1.

Stir at 25-35° C. for 1-2 hours.

Filter the solid and wash the solid with water Lot-2.

Dry the solid at 25-35° C. M.C reaches to below 3%.

Yield: 680 g

% of Yield: 80%.

Purity by HPLC: 90.56%.

It was found that other suitable amine bases, preferably a tertiary amine base (e.g. DBU, pyridine, DMAP) can be used to achieve good yield. For example, pyridine has been used at reflux for 18 h to give 88% yield of product. THF or acetonitrile were used as alternative solvents to DMF, with acetonitrile preferred.

Example 1-4

Preparation of Compound 6.3

Reagents

| Raw materials | Quantity | M. Wt | Moles | Equiv |
|---|---|---|---|---|
| Compound 6.2 | 300 g | 491.3 | 0.61 | 1.0 |
| DCM | 278 mL | — | — | — |
| Trifluoroacetic acid | 278 mL | 114 | 3.66 | 6.0 |
| Diisopropylether Lot-1 | 600 mL | — | — | — |
| Diisopropylether Lot-2 | 300 mL | — | — | — |
| Water Lot-1 | 3.0 L | — | — | 10 Vol |
| Water Lot-2 | 600 mL | — | — | — |
| Sat. NaHCO₃ Solution | ~500 mL | — | — | — |

Experimental Procedures

Charge compound 6.2 into a clean and dry RB flask at 25-35° C.

Charge DCM into RB flask at 25-35° C.

Cool the reaction mass to 0-5° C.

Add TFA at 0-5° C. slowly (or HCl in dioxane).

Raise the reaction mass temperature to 25-35° C.

Stir the reaction mass at 25-35° C. for 18-20 hours.

Check the proceeding of reaction by TLC.

If TLC complies distill the reaction mass under vacuum below 40° C.

Charge Diisopropyl ether at 25-35° C.

Stir at 25-35° C. for 30-45 minutes.

Filter the solid and wash the solid with Diisopropyl ether Lot-2.

Suck dry the solid for 15 minutes.

Charge the wet solid into a clean and dry beaker.

Charge Water Lot-1 at 25-35° C.

Slowly adjust the reaction mass pH to 9-10 with sat-.NaHCO₃ solution.

Stir the reaction mass at 25-35° C. for 15-30 minutes.

Filter the solid and wash the solid with water Lot-2.

Dry the solid at 25-35° C. till to get constant weight.

Yield: 160 g.

% of Yield: 88%.

Purity by HPLC: 98.68%.

It was also found that other suitable conditions such as HCl/dioxane, HCl/MeOH, etc could be employed to remove the Boc protecting groups.

Example 1-5

Preparation of Compound 6.4

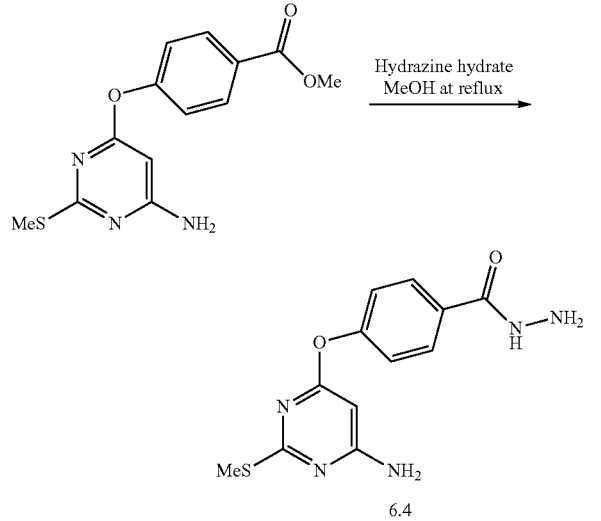

Reagents

| Raw materials | Quantity | M. Wt | Moles | Equiv |
|---|---|---|---|---|
| Compound 6.3 | 250 g | 291.3 | 0.8 | 1.0 |
| Methanol | 1.25 L | — | — | 5 Vol |
| Hydrazine hydrate | 257.46 mL | 50 | 5.1 | 6.0 |
| Water Lot-1 | 1000 mL | — | — | — |
| Water Lot-2 | 500 mL | — | — | — |

Experimental Procedures

Charge compound 6.3 into a clean and dry RB flask at 25-35° C.

Charge Methanol and Hydrazine hydrate (or anhydrous hydrazine) at 25-35° C.

Heat the reaction mass to reflux.

Stir at reflux for 9-10 hours.

Check the progress of by TLC.

Upon completion, distill off solvent completely under vacuum at 40-50° C.

Charge Water Lot-1 at 25-35° C.

Stir at 25-35° C. for 1 hour.

Filter the solid and wash the solid with water Lot-2.

Dry the solid at 25-35° C. till to get constant weight.

Yield: 191 g.

% of Yield: 77%

Purity by HPLC: 99.54%. .

Example 1-6

Preparation of Compound 6

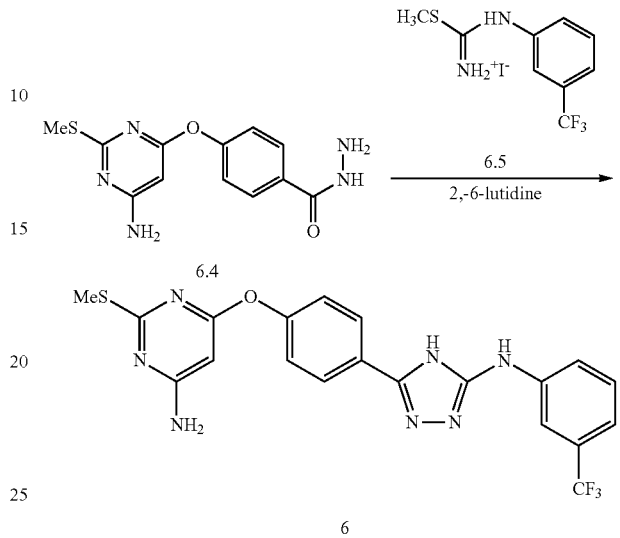

Reagents

| Raw materials | Quantity | M. Wt | Moles | Equiv |
|---|---|---|---|---|
| Trifluoromethyl phenyl thiourea 6.5 | 110 g | 220 | 0.49 | 1.0 |
| DCM | 1.1 L | — | — | 10 |
| Methyl iodide | 212.79 | 141.9 | 1.49 | 3.0 |
| Compound 6.4 | 120 g | 291.3 | 0.41 | 0.83 |
| Acetonitrile | 600 mL | — | — | — |
| 2,6 lutidine | 220.4 g | 107 | 2.05 | 4.0 |
| Ethyl acetate Lot-1 | 1.2 L | — | — | 10 |
| Water Lot-1 | 1.2 L | — | — | 10 |
| 10% Citric acid solution | 1.2 L | — | — | 10 |
| Water Lot-2 | 1.2 L | — | — | 10 |
| $Na_2SO_4$ | 50 g | — | — | — |
| Ethyl acetate Lot-II | 220 mL | — | — | 2 Vol |

Experimental Procedures

Charge trifluoro methyl phenyl thiourea (6.5) into a clean and dry RB flask at 25-35° C.

Charge DCM and Methyl iodide at 25-35° C.

Heat the reaction mass to reflux.

Stir at reflux for 3-4 hours.

Check the progress of by TLC.

Upon completion of the reaction, distill off solvent completely under vacuum at 40-50° C.

Charge acetonitrile to above crude material at 25-35° C. at $N_2$ atmosphere.

Charge compound 6.4 and 2,6-lutidine.

Heat the reaction mass to reflux.

Maintain the reaction mass under reflux for 16-17 hours at $N_2$ atmosphere.

Check the progress of the reaction by TLC.

Upon completion, distill off the solvent completely under vacuum.

Dissolve the residue in Ethyl acetate Lot-1.

Wash the Ethyl acetate layer with Water Lot-1.

Wash the Ethyl acetate layer with 10% Citric acid solution.

Wash the Ethyl acetate layer with Water Lat-2.
Dry the Ethyl acetate layer over Sodium sulphate.
Wash the sodium sulphate with Ethyl acetate Lot-2.
Distill off the total Ethyl acetate layer under vacuum at 50-55° C.
Filter the solid and wash the solid with water Lot-2.
Dry the solid at 25-35° C. till to get constant weight.
Yield: 245 g. (Crude)
Purity by HPLC: 86.4%.

It was found that the use of suitable base would greatly improve the yield and purity. For example, the use of $Cs_2CO_3$ in DMF failed to afford product and the use of pyridine (5 eq) as solvent/base at reflux for 5 h afforded 55% yield, contaminated with isosteric oxadiazole analog which was difficult to remove. Conditions developed herein with lutidine suppress the formation of oxadiazole analog and provide efficient and economic ways to prepare compounds of interests. Other suitable solvents for the reaction may be acetonitrile, DMF, N-methyl-pyrrolid-2-one (NMP), $^t$BuOH or $^i$PrOH.

Example 2

Mesylate Salt of Compound 6

The Mesylate salt was prepared from either crude or purified compound 6 with about same yield. The analytical data shows bis-mesylate salt with monohydrate solvate.

Reagents

| Raw materials | Quantity | M. Wt | Moles | Equiv |
|---|---|---|---|---|
| crude compound 6 | 39 g | 459 | 0.08 | 1.0 |
| Methane sulfonic acid | 16.31 g | 96 | 0.16 | 2.0 |
| Methanol Lot-1 | 160 mL | — | — | — |
| Chilled Methanol Lot-2 | 50 mL | — | — | — |
| Methanol Lot-3 | 200 mL | — | — | — |
| Chilled Methanol Lot-4 | 60 mL | — | — | — |

Procedures

Charge crude compound 6 into a clean and dry RB flask at 25-35° C.
Charge Methanol Lot-1 into RB flask at 25-35° C.
Stir at 25-35° C. for 10-15 minutes.
Add Methanesulfonic acid slowly at 25-35° C.
Stir the reaction mass at 25-35° C. for 3-4 hours.
Filter the solid and wash the solid with Chilled methanol Lot-2(Pre cooled).
Dry the solid at 25-35° C. for till to get constant weight. (Purity by HPLC: 94.5%)
Charge the solid into a clean and dry RB flask at 25-35° C.
Charge Methanol Lot-3 at 25-35° C.
Stir at 25-35° C. for 1-2 hours at 25-35° C.
Filter the solid and wash the solid with chilled methanol Lot-4(Pre cooled).
Dry the sold at 25-35° C. till to get constant weight.
Yield: 38 g
Purity by HPLC: 98.2%.
Mesylate content: 33.28% (Bis Mesylate)
Moisture content: 6.08% (Mono hydrate)

Example 3

Preparation of Pyridine Hydrazide Precursor 44

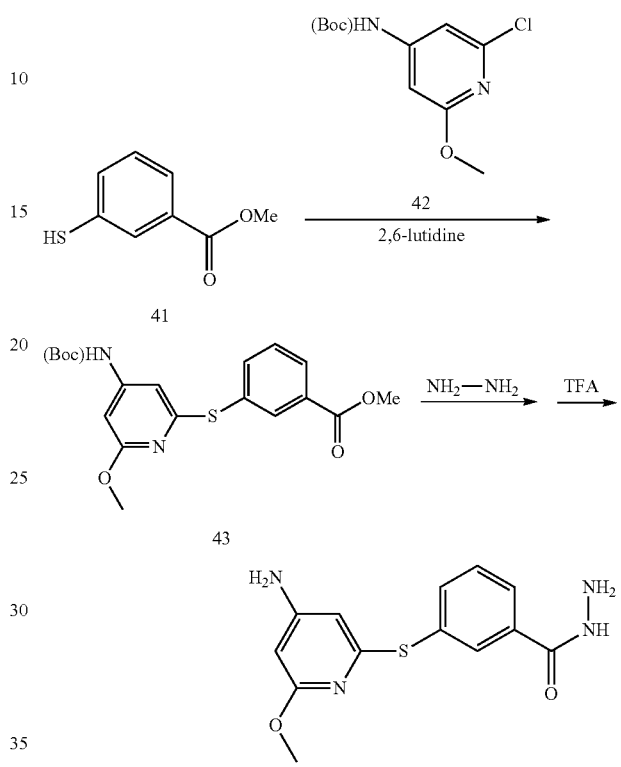

Compound 42 is prepared from methyl 3-mercaptobenzoate (41) and compound 42 under basic condition (e.g. 2-6-lutidine or DABCO). The ester functional group of compound 43 is then converted to hydrazide first (hydrazine reaction) and then Boc protecting group is deprotected under acidic condition (e.g. TFA) to afford compound 44.

Example 4

Preparation of Quinazoline Hydrazide 48

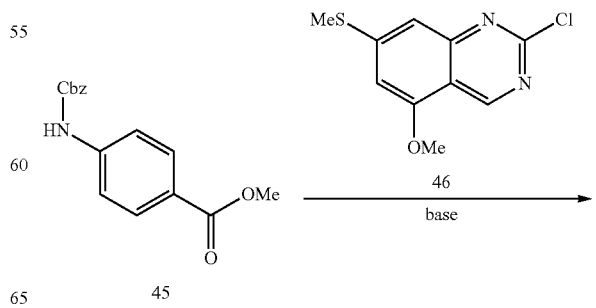

-continued

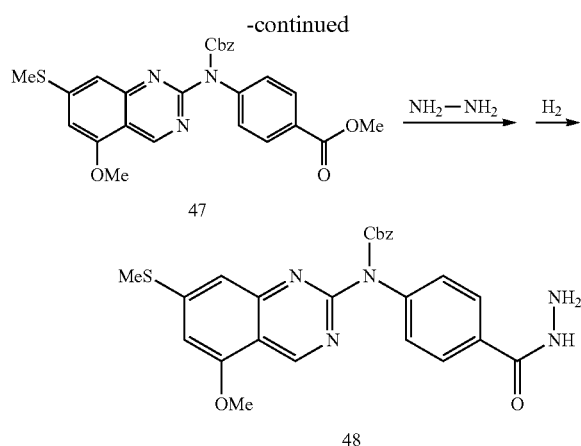

47

48

Compound 47 is prepared from methyl 4-(benzyloxycarbonylamino)benzoate (45) and compound 46 under basic condition (e.g. 2-6-lutidine or pyridine). The ester functional group of compound 47 is then converted to hydrazide first (with hydrazine) and then Cbz protecting group is deprotected under hydrogenation condition to afford compound 48.

Example 5

Preparation of Triazole 49

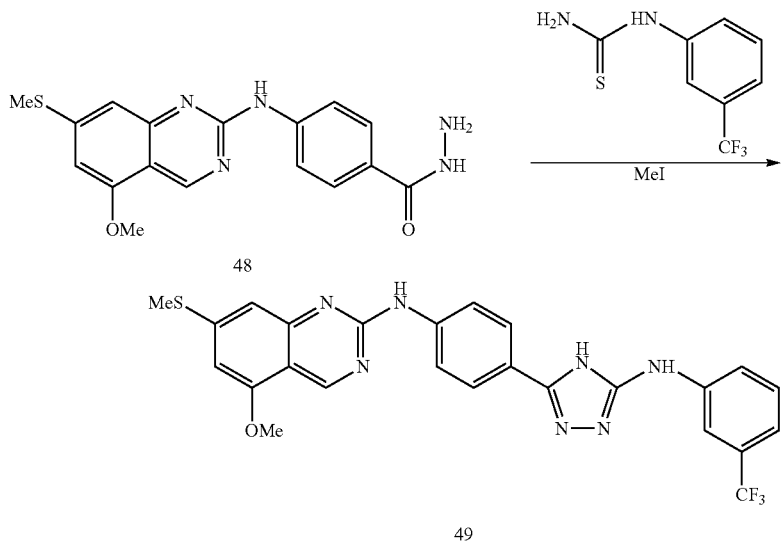

49

Triazole compound 49 is prepared under similar condition as described in Example 6 from compound 48.

Example 6

Design of a Selective Type II PDGFRβ/B-RAF Inhibitor

Figures 1B, 1C:
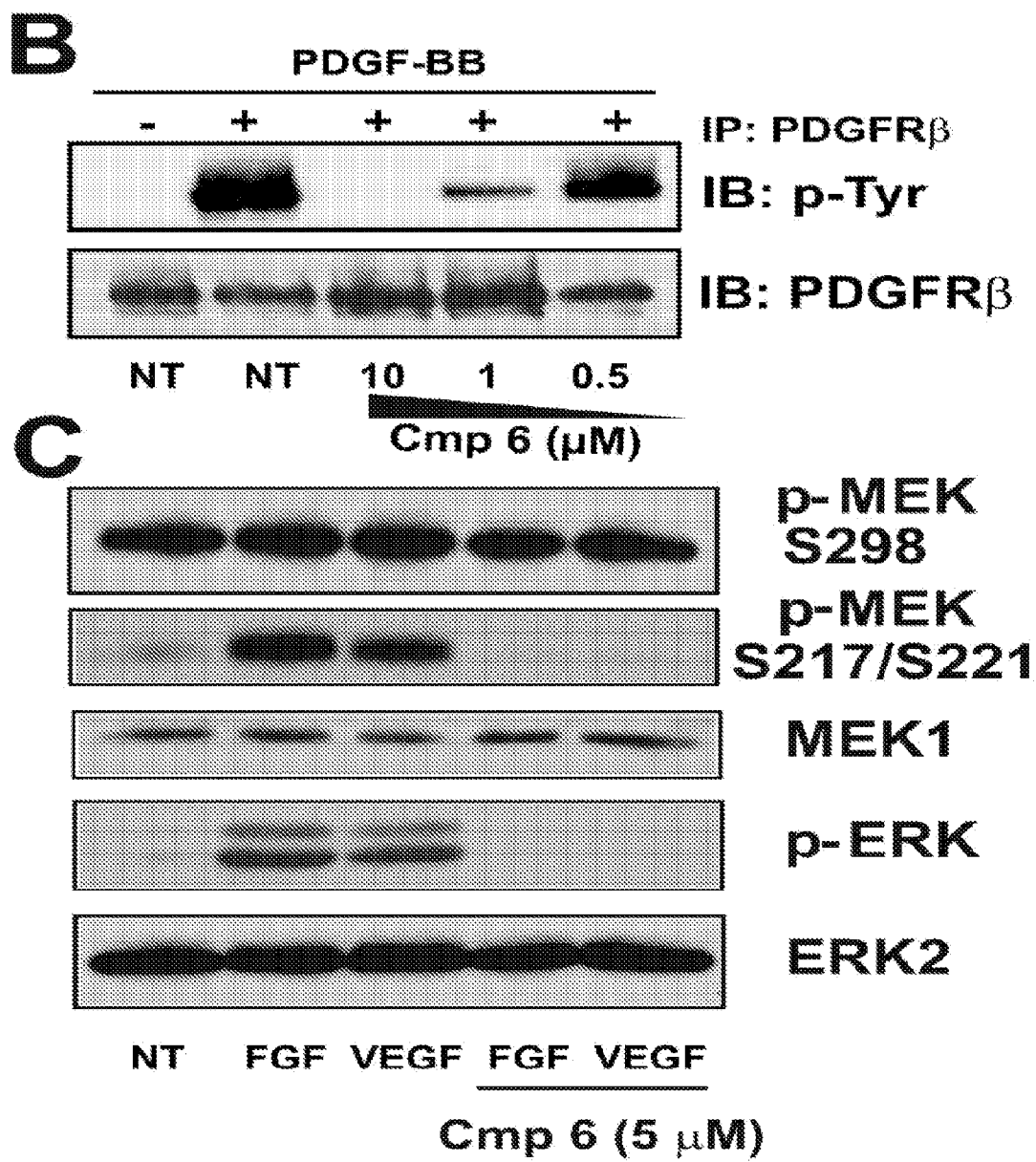
Figure 6:
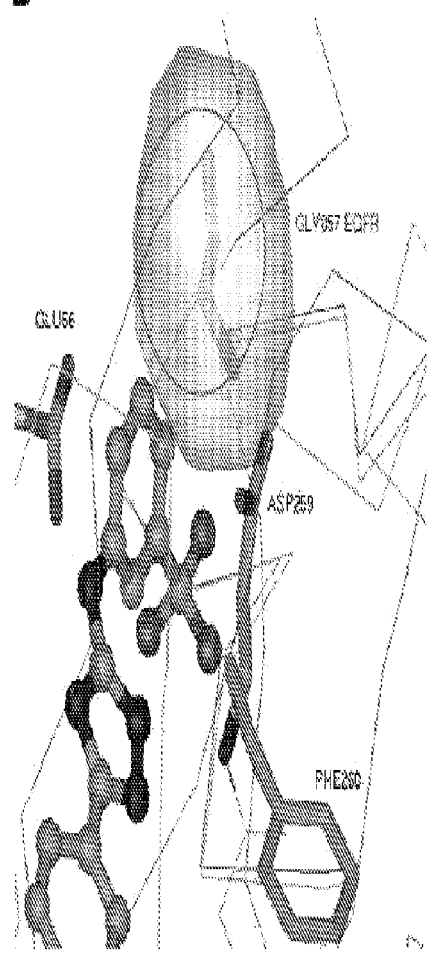
FIG. 6A-B provide sequence alignment of EGFR, B-RAF, and PDGFRβ primary sequences and docking of compound 6 into PDGFRβ with an EGFR activation loop.

While the overall homology of the PDGFRβ and B-RAF kinase domains is relatively low (29.1% homology and 47.3% similarity, see FIG. 6A), these two kinases feature structurally related type II pockets, guiding the design of an amino-triazole scaffold to fit into the allosteric site in the inactive conformation of these and other kinases while avoiding the ATP pocket (FIG. 1A). Amino-triazole based compounds were screened in human primary cell-based assays for their ability to suppress PDGF-BB-mediated PDGFRβ autophosphorylation in vascular smooth muscle cells (VSMCs) and growth factor-mediated MEK and ERK phosphorylation in endothelial cells (ECs) (FIGS. 1B and C). Structure-activity relationships demonstrate the critical substituents for cell-based PDGFRβ and RAF inhibition (FIG. 1D) and are further described herein. Active compounds were then screened for anti-angiogenic activity in the developing zebrafish (from 20-48 hours post fertilization (hpf)) by evaluating the growth of intersegmental vessels (FIG. 3). Successive rounds of molecular modeling, chemical synthesis, as well as cell-based and zebrafish screening were performed to refine the active molecules.

Example 7

Effect of Compounds on Cell Viability

Figure 1D:
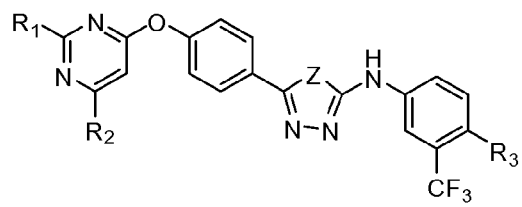
Figure 1E:
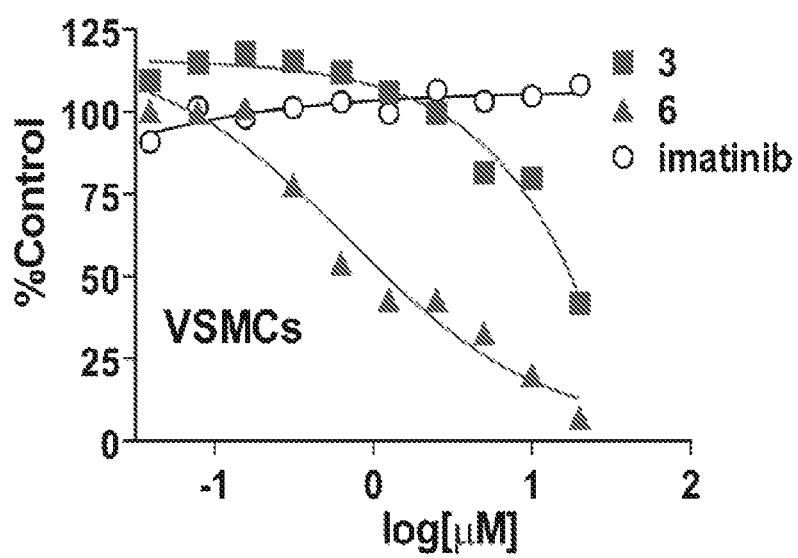
Figure 1F:
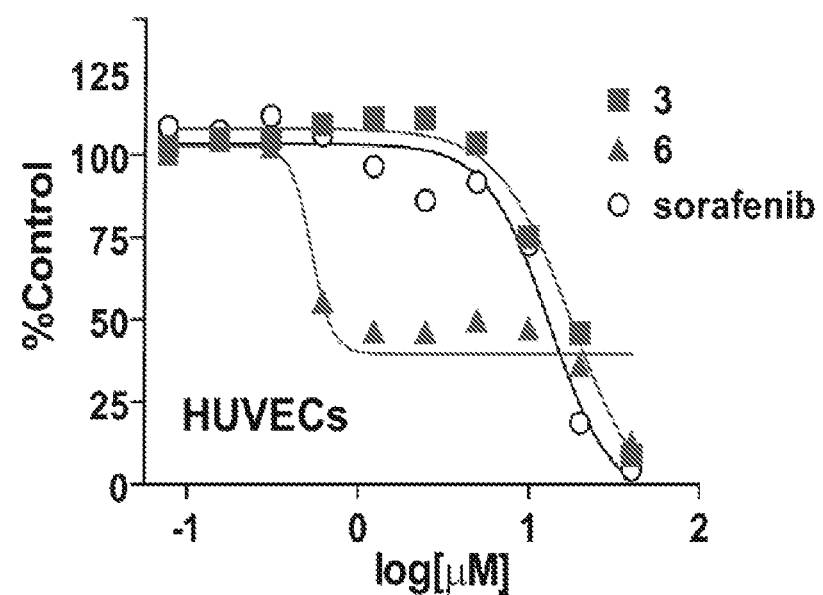

The effects of compound 3 vs. 6 on VSMC or EC viability were tested since compound 3 inhibited PDGFRβ, while compound 6 inhibited both RAF and PDGFRβ (see SAR in FIG. 1D). Compound 6 inhibited VSMC viability with an $EC_{50}$ of 0.59 μM, whereas 3 produced an $EC_{50}$ of 15.0 μM (FIG. 1E). Imatinib (PDGFRβ among its kinase targets) did not demonstrate any inhibition of VSMC viability at the highest concentration tested (20 μM). Compound 6 inhibited endothelial cell viability with an $EC_{50}$ of 0.54 μM, whereas 3 produced an $EC_{50}$ of 18.04 μM (FIG. 1F) confirming our SAR demonstrating that the methylthiol group and both PDGFRβ and p-MEK inhibitory activity are critical for the cytotoxic effects observed. Interestingly, sorafenib, a RAF inhibitor with both type II and ATP competitive binding properties, produced an $EC_{50}$ of 13.24 μM on the viability of the ECs indicating that sorafenib was 25-fold less potent than 6 in this cell-based assay.

Example 8

Comparison of Compound 6 to Sorafenib In Vitro

Compound 6 and sorafenib were further compared in a panel of in vitro ATP-dependent kinase assays consisting of several targets that are inhibited by sorafenib. Compound 6 did not inhibit any of the following active kinases: B-RAF, C-RAF, VEGFR1, VEGFR2, Flt3, Kit, and PDGFRβ as well as several others, even at 10 μM (Table 1). This is not surprising given that compound 6 requires the inactive conformation of the enzyme for interaction. In contrast, sorafenib inhibits the kinase activity of B- and C-RAF in addition to VEGFR2 and several other receptor tyrosine kinases whereas compound 3, like 6, did not inhibit any of the active kinases tested.

TABLE 1

In vitro kinase panel comparing compounds 3, 6, and sorafenib

| | % Inhibition at 10 μM | | |
|---|---|---|---|
| Kinase Target | Cmp 3 | Cmp 6 | sorafenib |
| ABL1 | 4 | 3 | 50 |
| AKT1 | 1 | 2 | 2 |
| BRAF | 17 | −1 | 84 |
| CDK2 | 2 | 2 | 2 |
| CSF1R | 79 | 23 | 101 |
| CK2 alpha 1 | −3 | 0 | −3 |
| EGFR | −2 | −3 | −3 |
| EGFR L858R | −3 | −10 | −5 |
| EGFR L861Q | −1 | −4 | −4 |
| FGFR1 | 9 | 6 | 44 |
| FGFR2 | −1 | −2 | 83 |
| FGFR3 | −12 | −13 | 37 |
| FGFR3 K650E | 4 | −1 | 78 |
| FGFR4 | −6 | −7 | 7 |
| FLT1 (VEGFR1) | 5 | −2 | 93 |
| FLT3 | −4 | −2 | 9 |
| FLT3 D835Y | 29 | 9 | 72 |
| IGF1R | −4 | 0 | −3 |
| KDR (VEGFR2) | 31 | 16 | 104 |
| KIT | 74 | 28 | 37 |
| MEK1 | −5 | −2 | 0 |
| MEK2 | −8 | −6 | −4 |
| ERK2 | −4 | −5 | 0 |
| JNK3 | −8 | −8 | −4 |
| ERK1 | 1 | 2 | 3 |
| JNK1 | −5 | −3 | −2 |
| JNK2 | −7 | −4 | 10 |
| MAPKAPK2 | 1 | 2 | 2 |
| MET (cMet) | 7 | 3 | 2 |
| MET M1250T | 4 | −1 | 3 |
| PAK2 | 2 | 1 | 2 |
| PDGFR beta | 35 | 20 | 93 |
| PKC alpha | −5 | −1 | −2 |
| PKC beta I | −3 | 2 | −1 |
| PKC beta II | −3 | −4 | −3 |
| PKC delta | −1 | −1 | −4 |
| PKC epsilon | −3 | −1 | −2 |
| PKC gamma | 6 | 5 | −3 |
| PKC eta | 1 | 3 | 2 |
| PKC iota | −2 | 0 | −2 |
| FAK2 | −4 | −4 | −3 |
| CRAF Y340D Y341D | 38 | 3 | 95 |

Next, compound 6 was analyzed in a competitive binding assay (Karaman M W, et al. *Nature biotechnology* (2008) 26:127-132) against 70 kinases (with the majority as inactive) representing diverse family members of the kinome (FIG. 2 and Table 2). Relative to other type II inhibitors, imatinib and sorafenib, compound 6 displays improved selectivity, which is represented on the kinase dendrograms (FIG. 2). Among kinases, compound 6 inhibited only PDGFRα and β with Kds of 300 and 520 nM, respectively, as well as Flt3 and c-Kit at 52 and 170 nM, respectively (Table 3). A panel of CDKs were tested and weak binding was observed with CDKL2 (5.1 μM) and CDK11 (7.5 μM). While compound 6 did not inhibit RAF in this assay, this is not surprising since the RAF construct used in this assay has an N-terminal regulatory domain truncation likely influencing the allosteric conformation.

TABLE 2

Kinases screened with 10 uM compound 6 in the KINOMEscan profiling assay at Ambit Biosciences used to construct FIG. 2.

| Kinase | % Control |
|---|---|
| ABL1 | 100 |
| AMPK-alpha1 | 72 |
| ARK5 | 70 |
| AXL | 87 |
| BMX | 97 |
| BRAF | 91 |
| BRAF(V600E) | 98 |
| CDC2L1 | 70 |
| CDC2L2 | 83 |
| CDK11 | 32 |
| CDK11 | 32 |
| CDK2 | 87 |
| CDK3 | 91 |
| CDK5 | 88 |
| CDK7 | 97 |
| CDK8 | 67 |
| CDK9 | 100 |
| CLK2 | 84 |
| CSF1R | 51 |
| CSNK1E | 47 |
| DYRK1B | 85 |
| EPHA2 | 100 |
| EPHB4 | 94 |
| ERK2 | 90 |
| FAK | 100 |
| FGFR2 | 100 |
| FLT1 | 81 |
| FLT3 | 2.8 |
| FLT3(D835H) | 17 |
| FLT3(D835Y) | 18 |
| FLT3(ITD) | 3.1 |
| FLT3(N841I) | 3.1 |
| FLT4 | 100 |
| GSK3B | 90 |
| IGF1R | 100 |
| INSR | 100 |
| JNK1 | 98 |
| KIT | 0 |
| KIT(D616V) | 76 |
| KIT(V559D) | 0.1 |
| KIT(V559D, T670I) | 56 |
| KIT(V559D, V654A) | 15 |
| LIMK2 | 72 |
| LKB1 | 100 |
| MEK1 | 84 |
| MET | 94 |
| MLK3 | 96 |
| MYO3A | 94 |
| p38-alpha | 100 |
| PAK1 | 100 |
| PAK4 | 100 |
| PDGFRA | 0.25 |
| PDGFRB | 0.5 |
| PFTK1 | 71 |
| PIK3CA | 100 |
| PIM1 | 96 |
| PKAC-alpha | 100 |
| PRKCD | 74 |
| PRKCE | 91 |
| PRKD1 | 100 |
| RAF1 | 52 |
| RET | 95 |
| RIOK3 | 100 |
| RIPK1 | 84 |
| SRC | 90 |
| SRPK2 | 100 |

TABLE 2-continued

Kinases screened with 10 uM compound 6 in the KINOMEscan profiling assay at Ambit Biosciences used to construct FIG. 2.

| Kinase | % Control |
| --- | --- |
| TIE1 | 76 |
| TIE2 | 88 |
| TRKA | 64 |
| VEGFR2 | 80 |

TABLE 3

Kinome profile of compound 6 in the competitive binding assay (KINOMEscan)

| Kinase | Kd (nM) |
| --- | --- |
| FLT3 | 52 |
| KIT | 170 |
| PDGFRα | 300 |
| PDGFRβ | 520 |
| CDKL2 | 5,100 |
| CDK11 | 7,500 |
| ABL | >10,000 |
| B-RAF | >10,000 |
| CSF1R | >10,000 |
| FGFR2 | >10,000 |
| p38α | >10,000 |
| PAK1 | >10,000 |
| RET | >10,000 |
| VEGFR2 | >10,000 |

Although compound 6 failed to inhibit truncated RAF in the competitive binding assay, it completely disrupted phosphorylation of ERK T202/Y204 in cells expressing the constitutively active mutant of B-RAF (V600E), providing support that compound 6 directly targets RAF in cells (FIG. 7B). Additionally, compound 6 did not inhibit activation of either FGFR1 or VEGFR2 in endothelial cells (FIG. 7E) or in vitro (Table 2), but did inhibit the activation of PDGFRβ in vascular smooth muscle cells (FIG. 1B and FIG. 7E). A summary of the phospho-sites examined in bFGF or VEGFA stimulated ECs is found in Table 4.

TABLE 4

Cell-based profiling of compound 6.

| Phospho-Protein | Inhibition |
| --- | --- |
| C-RAF S259 | − |
| C-RAF S621 | − |
| C-RAF S338 | + |
| MEK-1/2 S217/S221 | + |
| ERK-1/2 T202/Y204 | + |
| ERK-5 T218/Y220 | − |
| Bad S112 or S155 | − |
| Src Y416 | − |
| Pan Phospho-PKC | − |
| p38 T180/Y182 | − |
| SAPK T183/Y185 | − |
| FAK Y861 | − |
| Akl S473 | − |
| VEGFR2 (phospho-tyrosine) | − |
| FGFR1 (phospho-tyrosine) | − |
| PDGPRβ (phospho-tyrosine) in SMCs | + |

HUVECs were pretreated with compound 6 for 1 h and stimulated with bFGF for 5 min. For PDGFRβ, VSMCs were pretreated with compound 6 for 1 h and stimulated with PDGF-BB for 7 min since HUVECs do not express this receptor.

Example 9

Phosphorylation Analysis of Compound 6

The specificity of compound 6 for RAF was further analyzed by evaluating its effect on specific phosphorylation sites both within and outside the RAF activation domain. Both bFGF and VEGF lead to phosphorylation of serine 338 (via PAK) within the activation domain of C-RAF while serine 259, which mediates the coupling of C-RAF to the adaptor protein 14-3-3 (Rommel C, et al. *Oncogene* (1996) 12:609-619), is constitutively phosphorylated (FIG. 7C). Compound 6 selectively blocked S338 phosphorylation, yet did not influence S259 (FIG. 7C), suggesting that its interaction with RAF preferentially influences its activation domain. Importantly, compound 6 did not inhibit PAK since it did not block PAK-mediated phosphorylation on MEK S298 in these cells (FIG. 1C).

Example 10

Evaluation of the Effect of Compound 6 on RAF Heterodimerization

Recent studies demonstrate the importance of B-RAF/C-RAF heterodimerization for effective MAPK signaling since heterodimerization dramatically increases the activity of both B-RAF and C-RAF (Rushworth, et al. (2006) *Mol Cell Biol* 26:2262-2272; Weber, et al. (2001) *Cancer Res* 61:3595-3598). Furthermore, certain mutations which induce an "open conformation" of B-RAF promote constitutive binding to C-RAF in cancer cells and this heterodimerization activates C-RAF and MEK signaling (Garnett, et al. (2005) *Molecular cell* 20:963-969). This defines RAF heterodimerization as an intriguing target for disrupting RAF activity in cells.

To evaluate the effect of compound 6 on RAF heterodimerization, endogenous RAF heterodimerization was induced in ECs by stimulating the cells with bFGF or VEGF and the ability of compound 6 to impact the formation of this complex was studied (FIG. 7D). Treatment of cells with compound 6 completely inhibited this heterodimer formation as well as ERK phosphorylation in response to either growth factor, while compound 3 had no effect (FIG. 7D). In addition, a MEK inhibitor, U0126, inhibited phosphorylation of ERK as expected, but greatly increased RAF heterodimerization above that achieved with growth-factor stimulation alone, suggesting the possibility of a feedback loop upon MEK inhibition. The finding that compound 6 inhibits phosphorylation of MEK and ERK in endothelial cells stimulated with bFGF or VEGF (FIG. 1C) provides evidence that compound 6 targets both B-RAF and C-RAF in cells and inhibition of MAPK signaling by disrupting RAF heterodimerization may be an ideal mechanism to deal with the compensatory roles of B-RAF and C-RAF.

Example 11

Analysis of the Effects of Compound 6 on New Blood Vessel Growth During Zebrafish Embryogenesis The effects of compound 6 were further analyzed to assess its mechanistic impact on new blood vessel growth during zebrafish embryogenesis. In embryos treated with compound 6 (1 μM in the water) the endothelial cells migrated away from the dorsal aorta as typically observed in control animals yet by 48 hpf they failed to form mature intersegmental vessels and similarly impacted the developing vasculature within the head region (FIG. 3A) while compound 3, which inhibits PDGFRβ but not B-RAF, had no effect. Following treatment, the blood vessels appeared highly disorganized and lacked the capacity to support blood flow. In contrast, fish treated with compound 3, even up to 10 μM, were indistinguishable from non-treated controls (FIG. 3A). It is important to note that compound 3 has Kds of 1.4, 3.7, 32, and 40 nM against Flt3, KIT, PDGFRα and PDGFRβ, respectively, in the competitive binding assay used in FIG. 2. Since compound 3 is ineffective at inhibiting angiogenesis in the zebrafish developmental embryogenesis model, it is clear that Flt3 and KIT do not play a role in blood vessel formation. Interestingly, SU5416 (Semaxanib)(12), a VEGFR2 inhibitor, while completely disrupting endothelial cell migration and neovascularization in the tail, had minimal effects on ocular vessels in these animals, suggesting that VEGF does not play an important role during ocular vascular development.

Example 12

Analysis of the Temporal Effects of Compound 6 on Angiogenesis

Figure 3C:
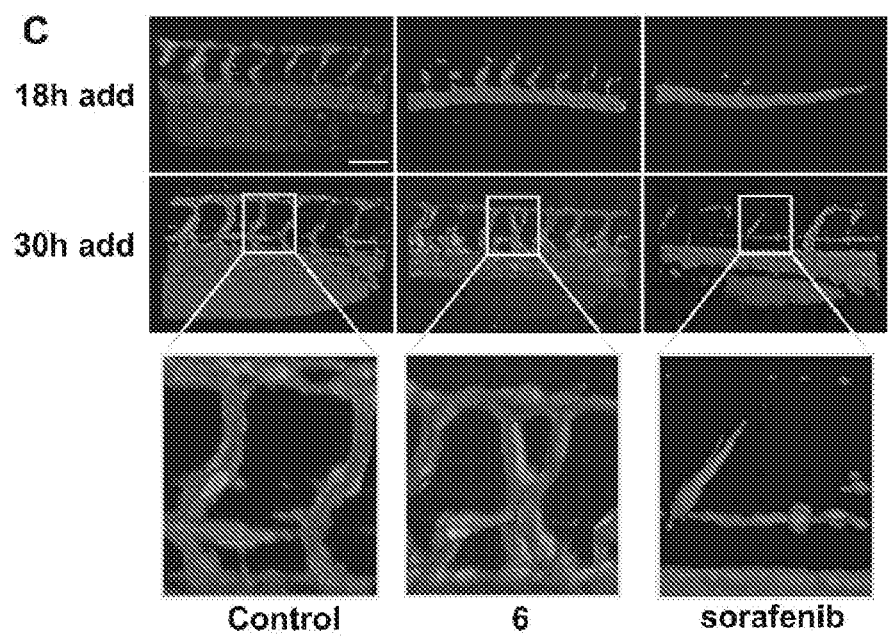
Figure 3D:
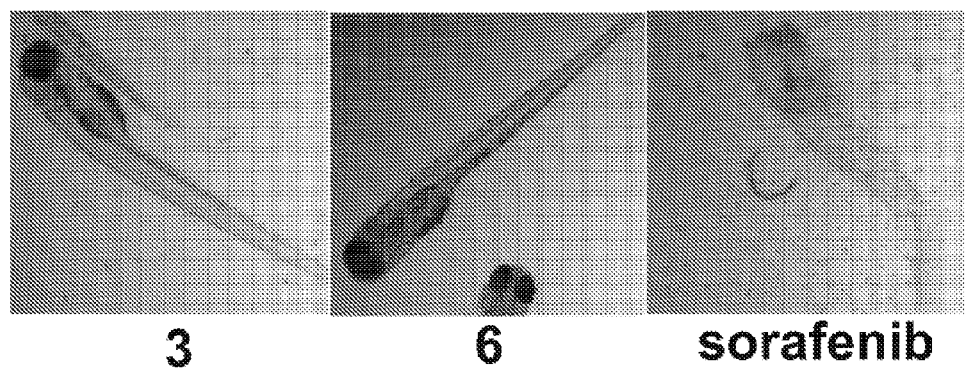

To analyze the temporal effects of compound 6 on angiogenesis, zebrafish were treated with compound 6 at 18 hpf and then analyzed at 35 hpf as lumens were beginning to form. Compound 6 showed no apparent effect on the vessels at 35 hpf, whereas imaging at 48 hpf suggests compound 6 impacts a late step in lumen formation (FIG. 3B). This was followed by the induction of apoptosis as shown by TUNEL stained intersegmental ECs at 48 hpf (FIG. 3B). In contrast, addition of compound 6 at 30 hpf (at the time when intersegmental vessel structure is first established) did not suppress the vascular growth and patterning (FIG. 3C) suggesting that once lumen formation is initiated, neovessels in these animals are resistant to the effect of 6. In contrast, sorafenib not only prevented the formation of new blood vessels but it also disrupted mature intersegmental blood vessels when added at 30 hpf (FIG. 3C). Additionally, treatment of embryos with compound 6 at 48-72 hpf had no effect on mature intersegmental vessels and the zebrafish were all viable, whereas treatment with sorafenib at this late time point induced death in all animals tested (FIG. 3D). Thus, compound 6 appears to disrupt a late step in neovascularization without detectable toxicity while sorafenib suppresses multiple processes during embryogenesis leading to lethality.

Example 13

Analysis of Anti-Angiogenic Effect by Dual Inhibition of PDGFRβ and RAF

Figure 4A:
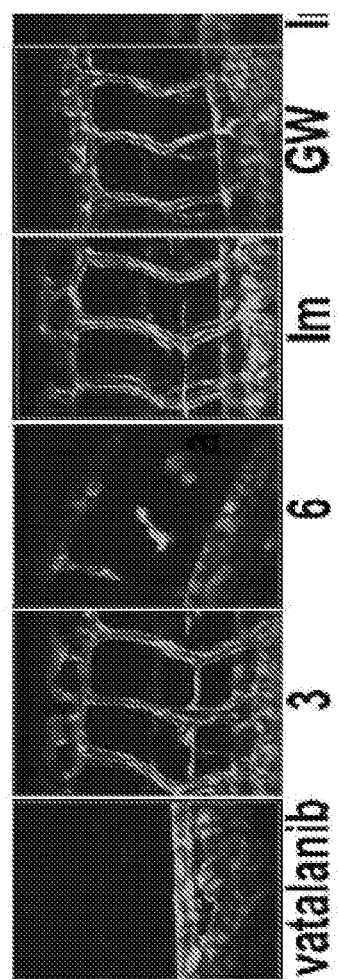
FIG. 4A-4C illustrate results regarding combination of imatinib and GW 5074 inhibiting angiogenesis similar to compound 6.

The requirement for dual inhibition of PDGFRβ and RAF for angiogenesis inhibition was investigated in the zebrafish model. Only the combination of RAF inhibition (GW 5074) and PDGFRβ inhibition (imatinib) led to a similar phenotype to compound 6, in which angioblasts migrate from the dorsal aorta and posterior cardinal vein but fail to form functional vessels with open lumens capable of supporting blood flow (FIG. 4A). Representative images of the Tg:fli1-EGFP zebrafish embryos demonstrate that 5 μM imatinib or 1 μM GW 5074 do not have an effect on intersegmental vessel formation and functional vessels with open lumens are observed (FIG. 4A).

Example 14

Co-Culture Angiogenesis Assay

Figure 4B:
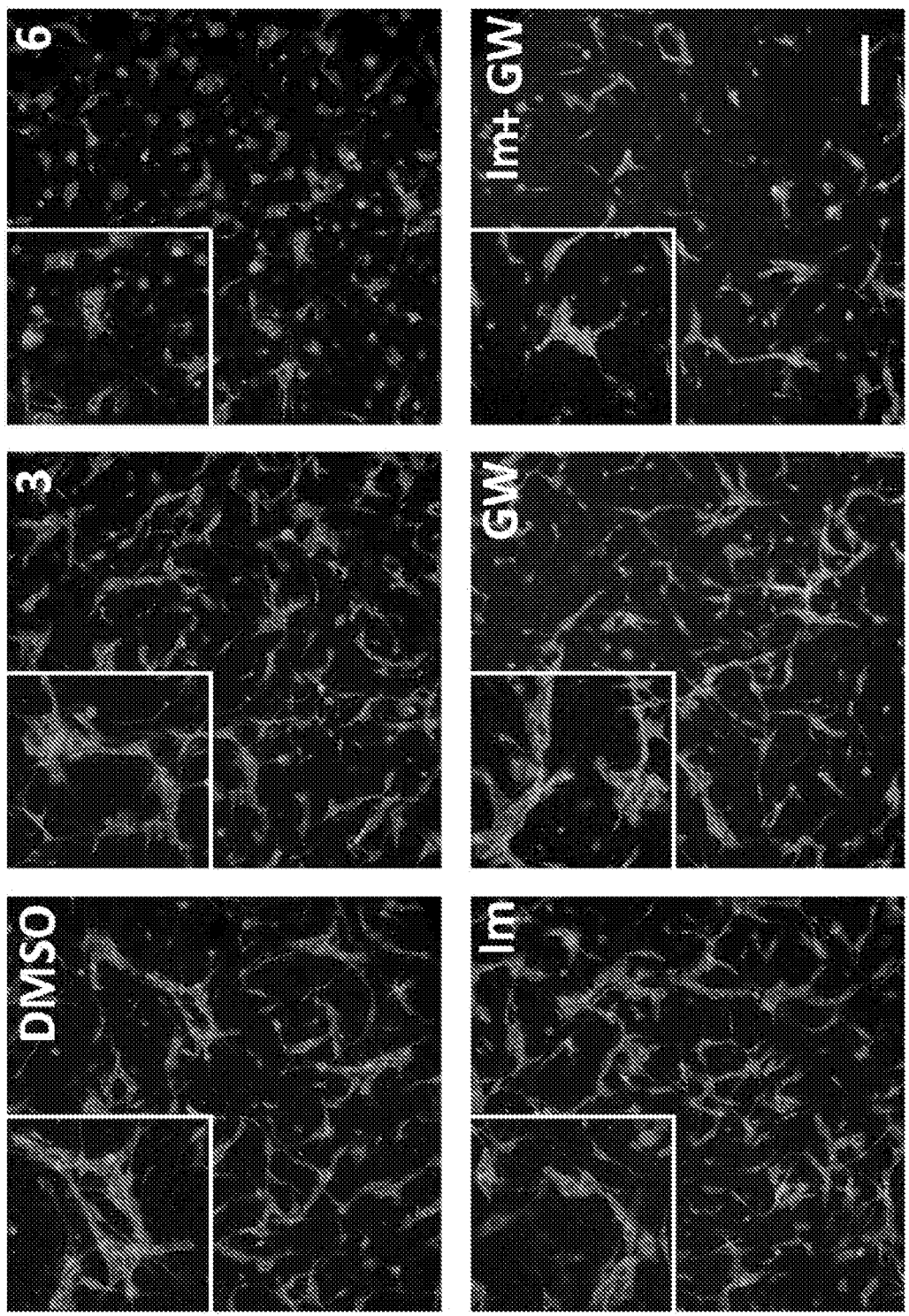
Figure 4C:
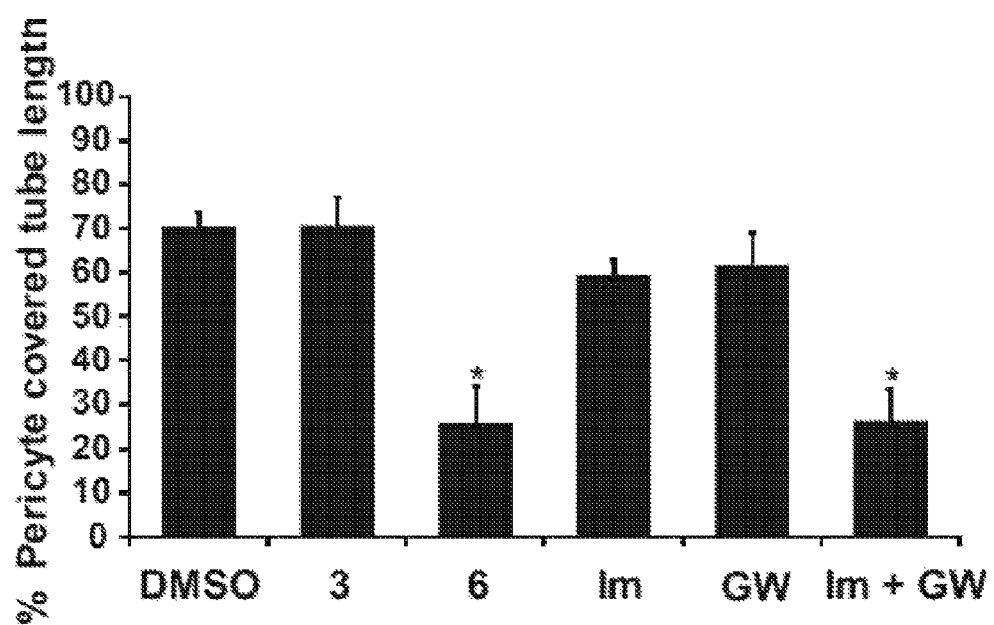

To validate the findings of Example 10, a co-culture angiogenesis assay was utilized to evaluate similar combinations of PDGFR and RAF inhibitors. In the assay, HUVECs are mixed with hepatic stellate cells (a pericyte found in the perisinusoidal space of the liver) in a 3D-collagen gel. The co-culture produced endothelial tubes with pericyte contacts (from the stellate cells) that can be imaged and quantified as shown in FIGS. 4B and C. Treatment of the co-cultures with 2.5 μM 6 led to a dramatic reduction in both overall endothelial tube formation as well as % pericyte-covered tube length (FIGS. 4B and C). Addition of 2.5 μM 3 or 1.0 μM imatinib (Im), which are both PDGFRβ inhibitors, did not affect endothelial tube formation or cause a significant change in pericyte coverage of the endothelial tubes (FIGS. 4B and C). A previously identified RAF inhibitor, GW 5074 (13), did not affect pericyte coverage or tube length alone, but combination with 1.0 μM imatinib produced a similar decrease in the % pericyte-covered tube length compared to 6 (FIGS. 4B and C).

Example 15

Assessment of Anti-Angiogenic Properties of Compound 6 in a Mammalian Model

Figure 9A:
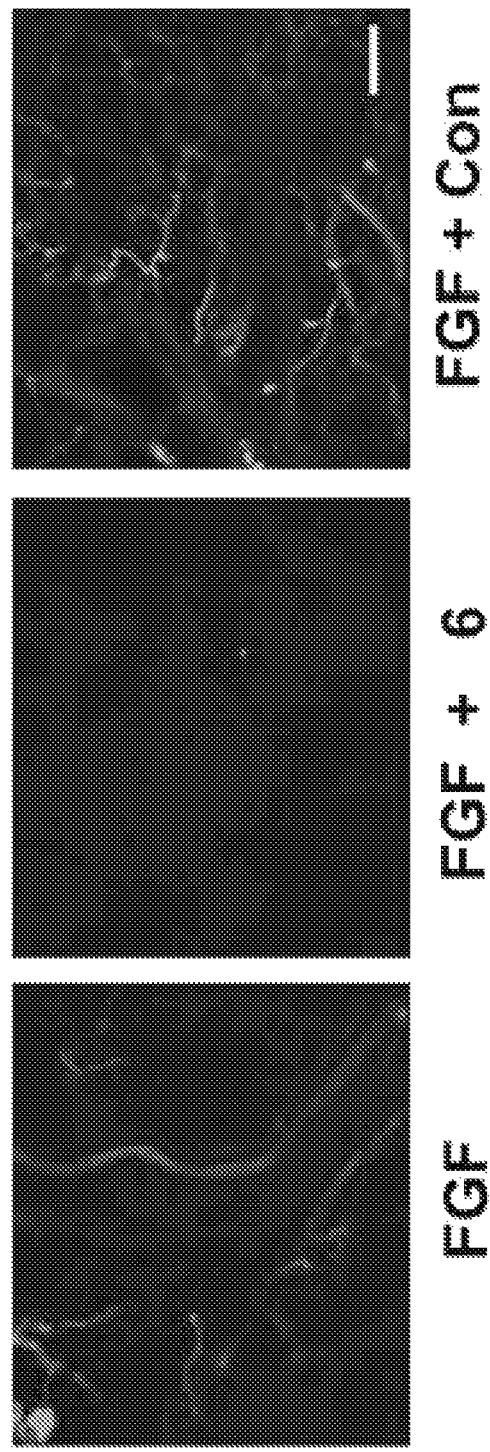
FIG. 9A-D show illustrative results of compound 6 disrupting angiogenesis in mice.
Figure 9B:
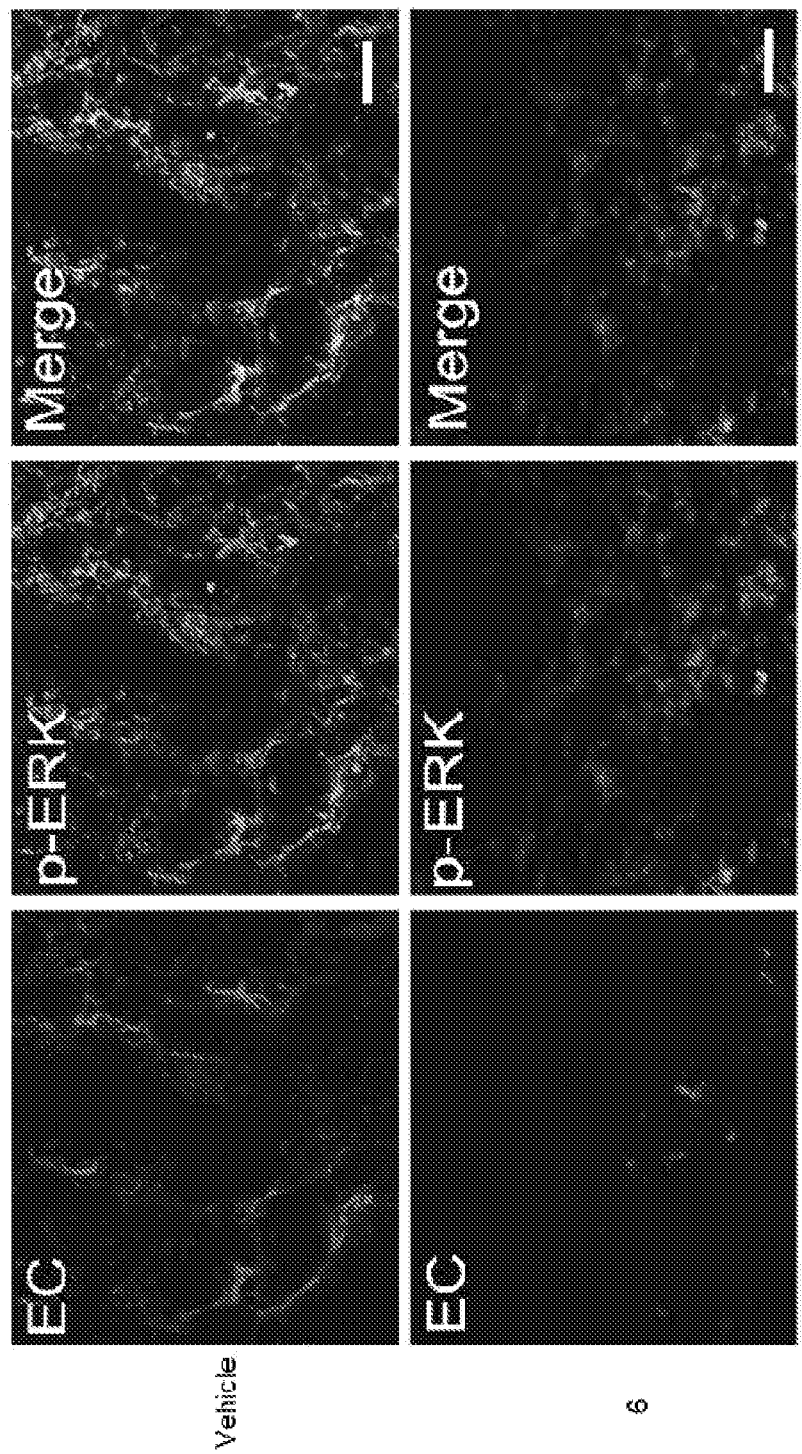
Figure 9C:
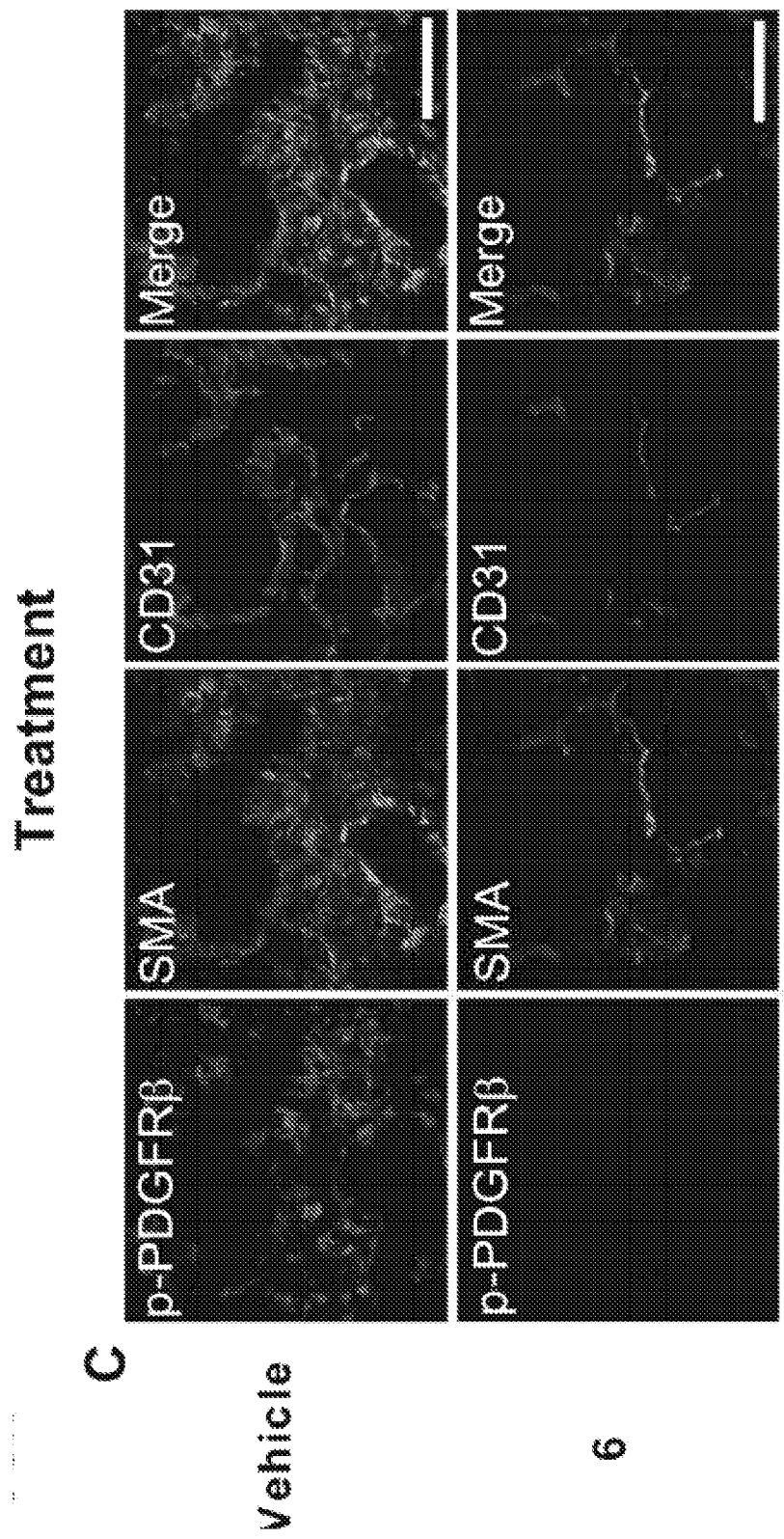
Figure 9D:
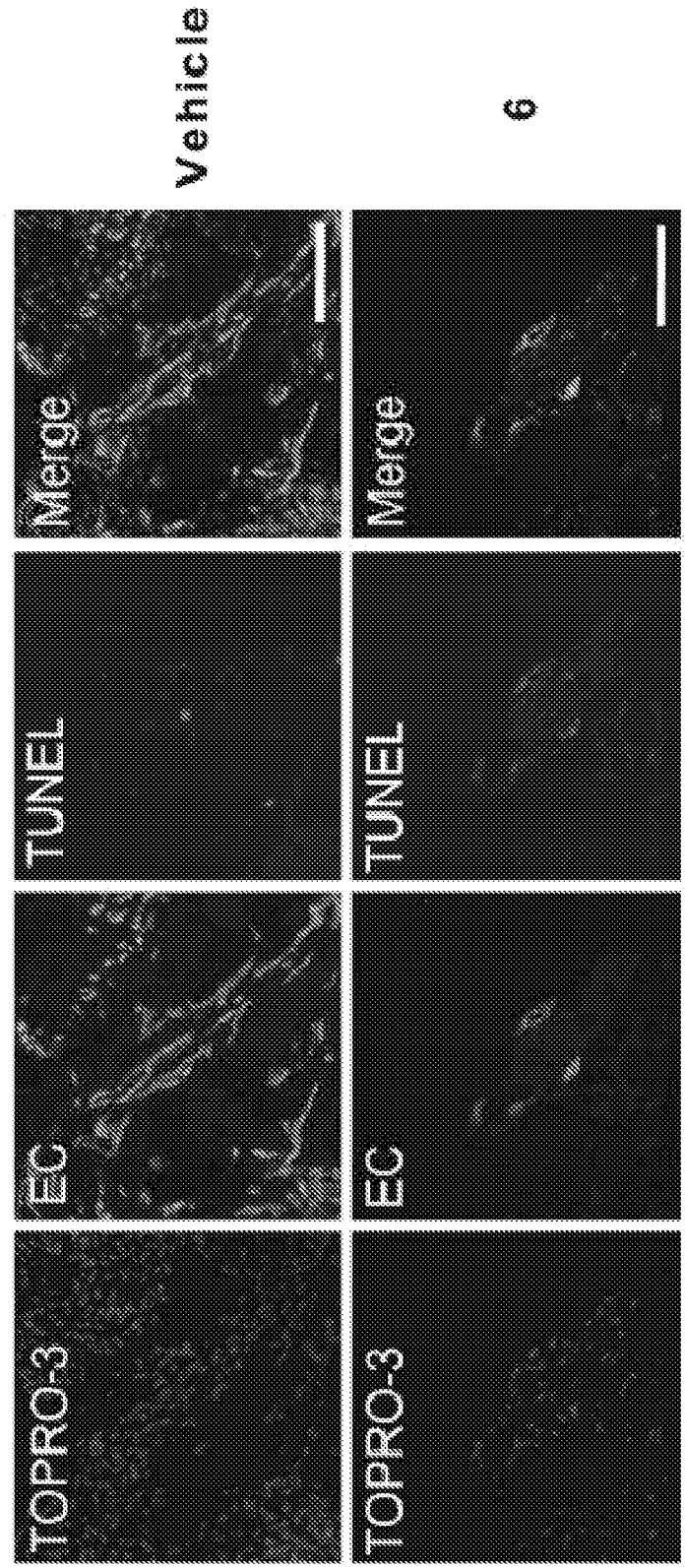

To assess the anti-angiogenic properties of compound 6 in a mammalian model, mice were subcutaneously injected with Matrigel containing bFGF to induce neovascularization and systemically treated with compound 6 at 50 mg/kg, ip, bid (pharmacokinetic analysis of the dose and formulation of compound 6 used indicated a $C_{max}$ of 3.6 μg/ml or 7.7 μM, $T_{1/2}$ corresponding to 11.5 h, and an $AUC^{0-12h}$ of 14.7 μg*h/ml). At this dose, compound 6 completely blocked angiogenesis relative to vehicle control (FIG. 9A) To monitor the effects of compound 6 on RAF signaling in vivo, cryosections of bFGF stimulated tissues for the presence of p-ERK immunostaining was evaluated. bFGF stimulation of these tissues led to intense p-ERK staining in both invasive endothelial and stromal cells. Systemic treatment of animals with compound 6 blocked MAPK pathway signaling within endothelial cells as suppression in the p-ERK staining in these cells was observed (FIG. 9B). Additionally, vehicle-treated mice displayed intense p-PDGFRβY751 in SMA-positive cells (FIG. 9C), while mice treated with compound 6 demonstrated a complete suppression in the p-PDGFRβY751 signal associated with the stromal compartment surrounding endothelial cells (FIG. 9C). Intense TUNEL staining among the neovessels in these tissues was observed but much less staining associated with the stromal cells adjacent to these vessels (FIG. 9D). Compound 6 blocked angiogenesis and inhibited RAF/PDGFRb in mice. Therefore, compound 6 disrupts a survival signal in actively growing blood vessels.

Example 16

Figure 5A:
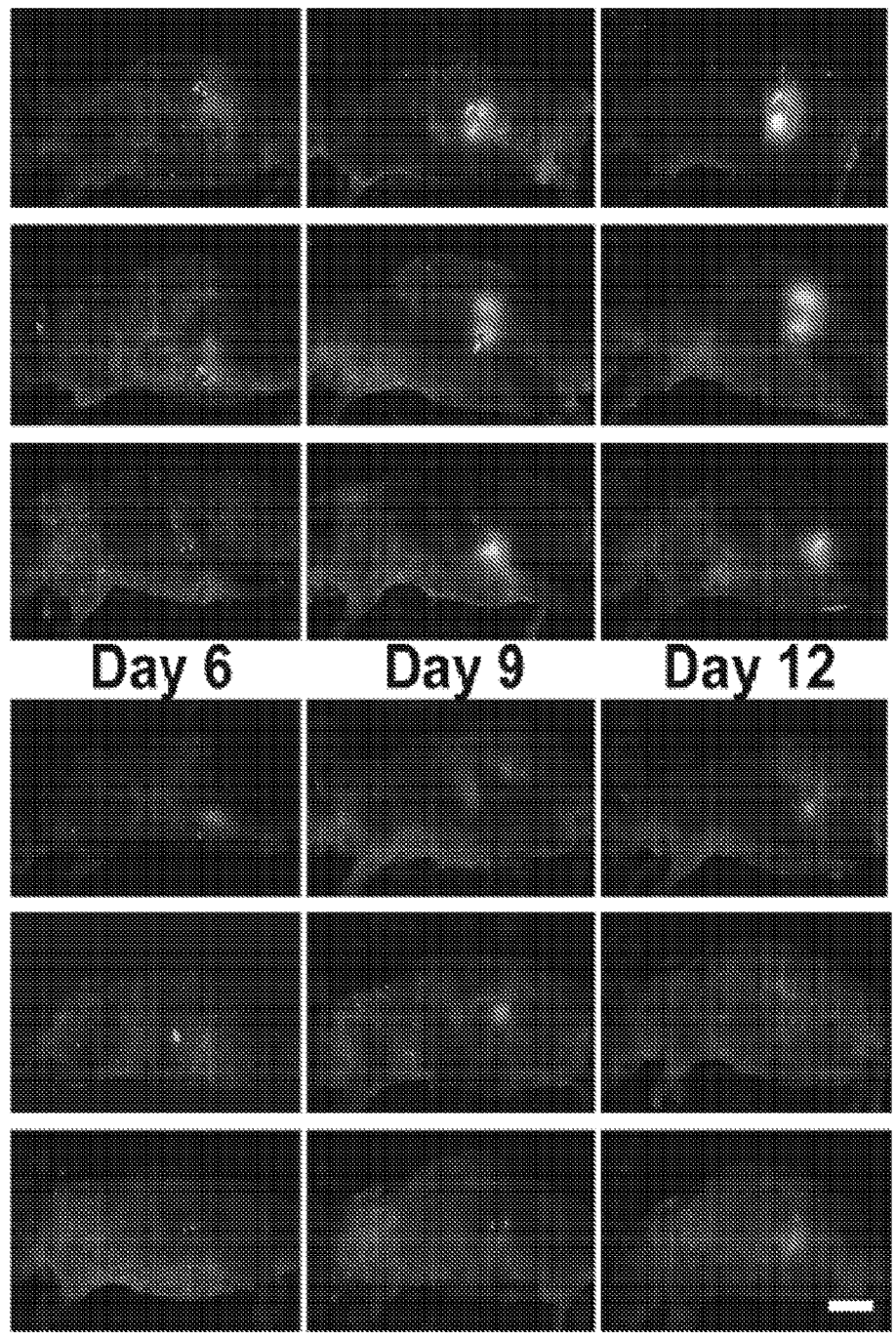
FIG. 5A-5F provide illustrative results of compound 6 inhibiting pancreatic tumor growth and reduces tumor vascular density.
Figure 5B:
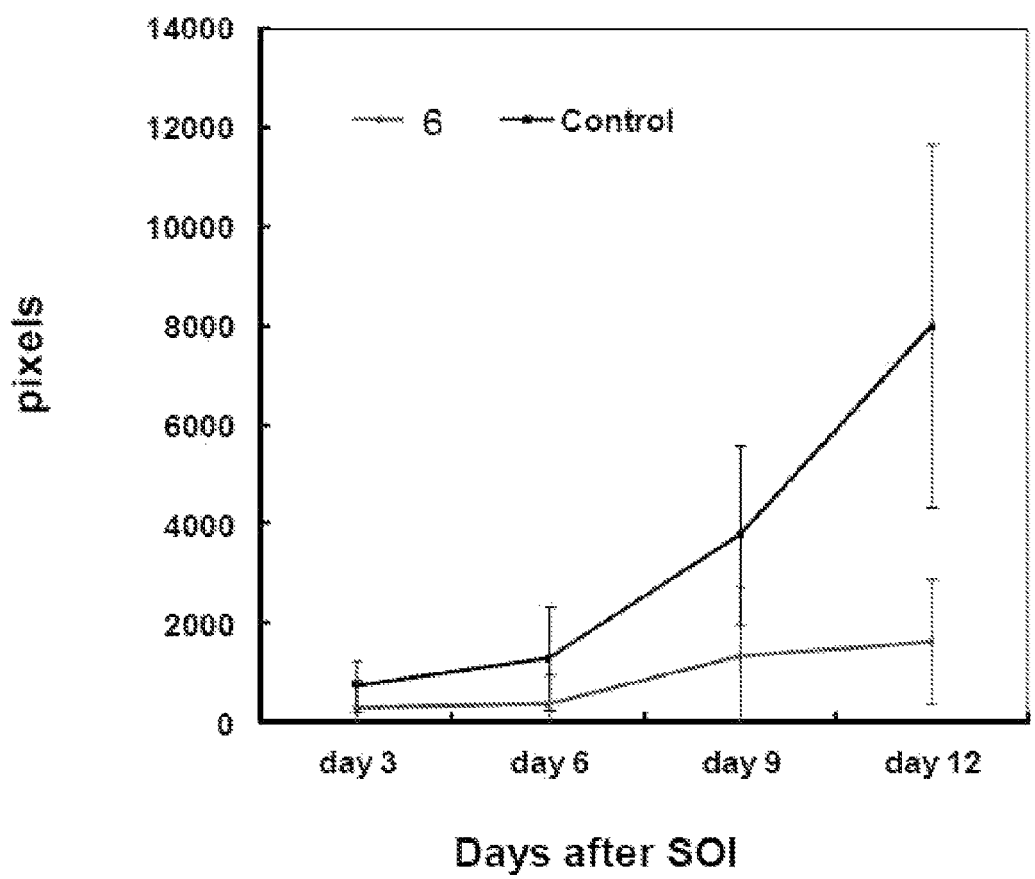
Figure 5C:
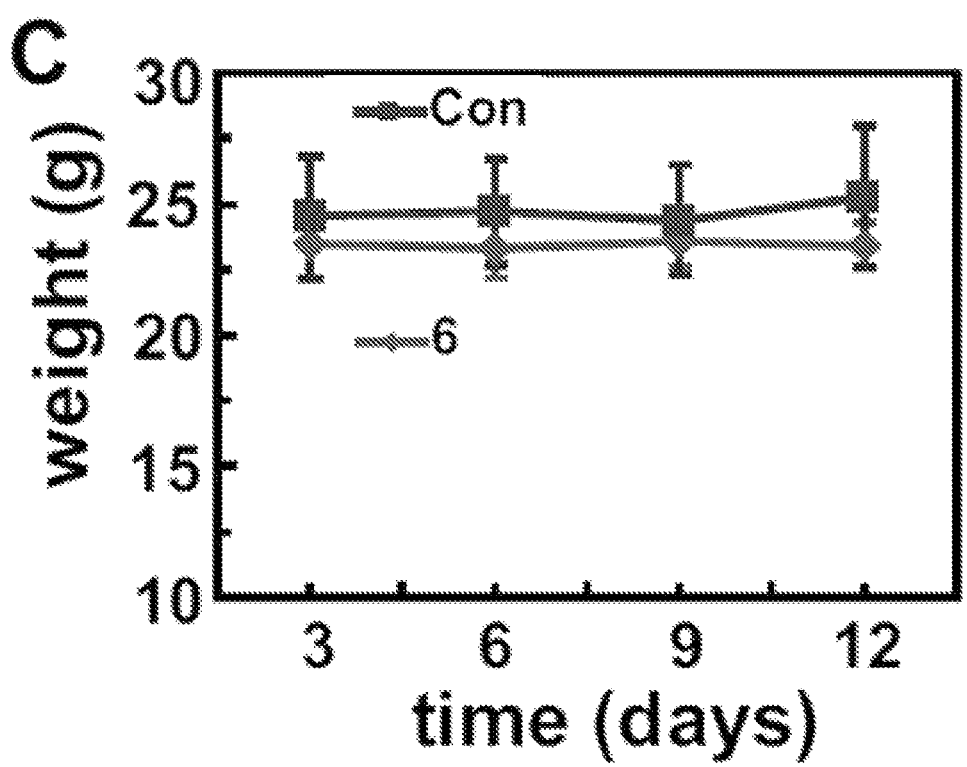

Effects of Compound 6 for Preventing Tumor Growth in an Orthotopic Pancreatic Carcinoma Model RFP expressing XPA-1 pancreatic tumor xenografts were implanted into the pancreas of Nestin GFP-mice enabling detection of both developing blood vessels (GFP) and primary tumor (RFP). Animals were systemically treated with either vehicle or compound 6 (50 mg/kg, bid) beginning 3 days after surgical orthotopic implantation (SOI) of a tumor fragment. Tumor growth was monitored non-invasively by whole body imaging using the Olympus OV100 Small Animal Imaging System to detect the RFP signal from the tumor implant within the pancreas. Tumor-growth was completely suppressed in animals treated with compound 6 compared to the vehicle alone 12 days post SOI. Representative time course images (lateral view) from three animals demonstrate that the growth of pancreatic tumors treated with compound 6 was suppressed and RFP intensity was abolished by day 12 after SOI compared to vehicle treated animals (FIG. 5A). The plot of tumor surface area over time reveals the increase in the vehicle treated animals relative to the animals treated with 6 (FIG. 5B). Clearly, 6 suppressed tumor growth in this model but caused no weight loss (FIG. 5C) or detectable toxicity (data not shown).

Figure 5D:
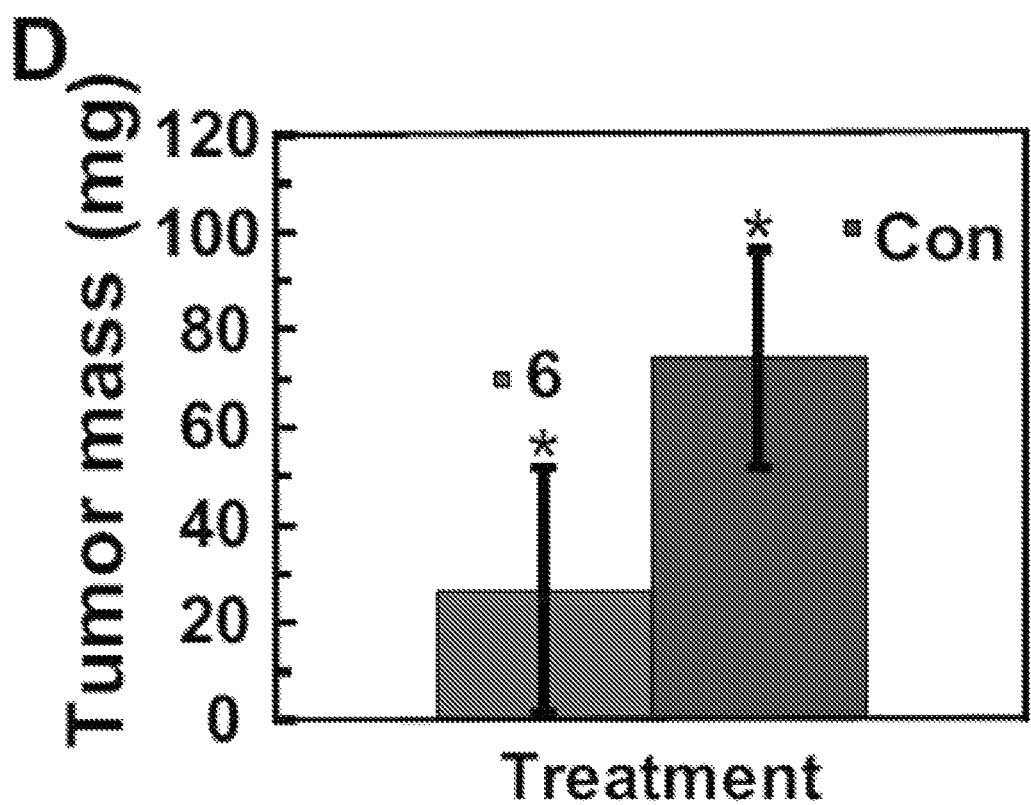
Figure 5E:
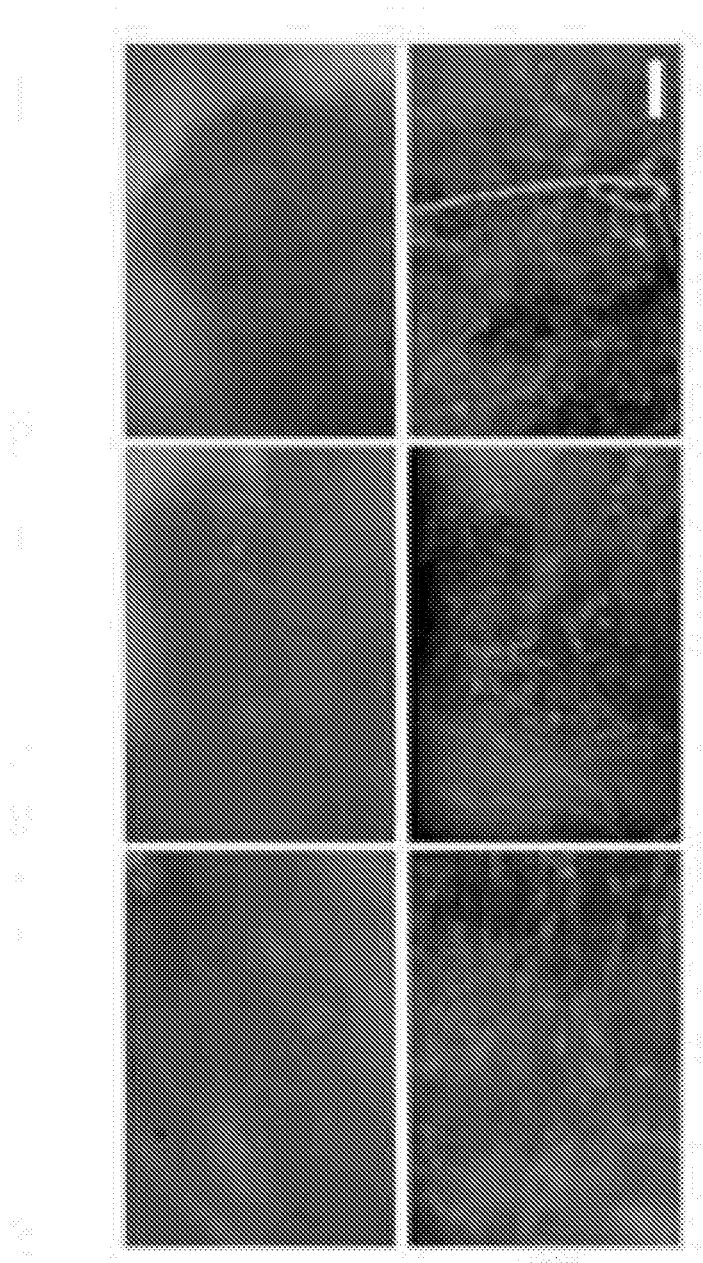
Figure 5F:
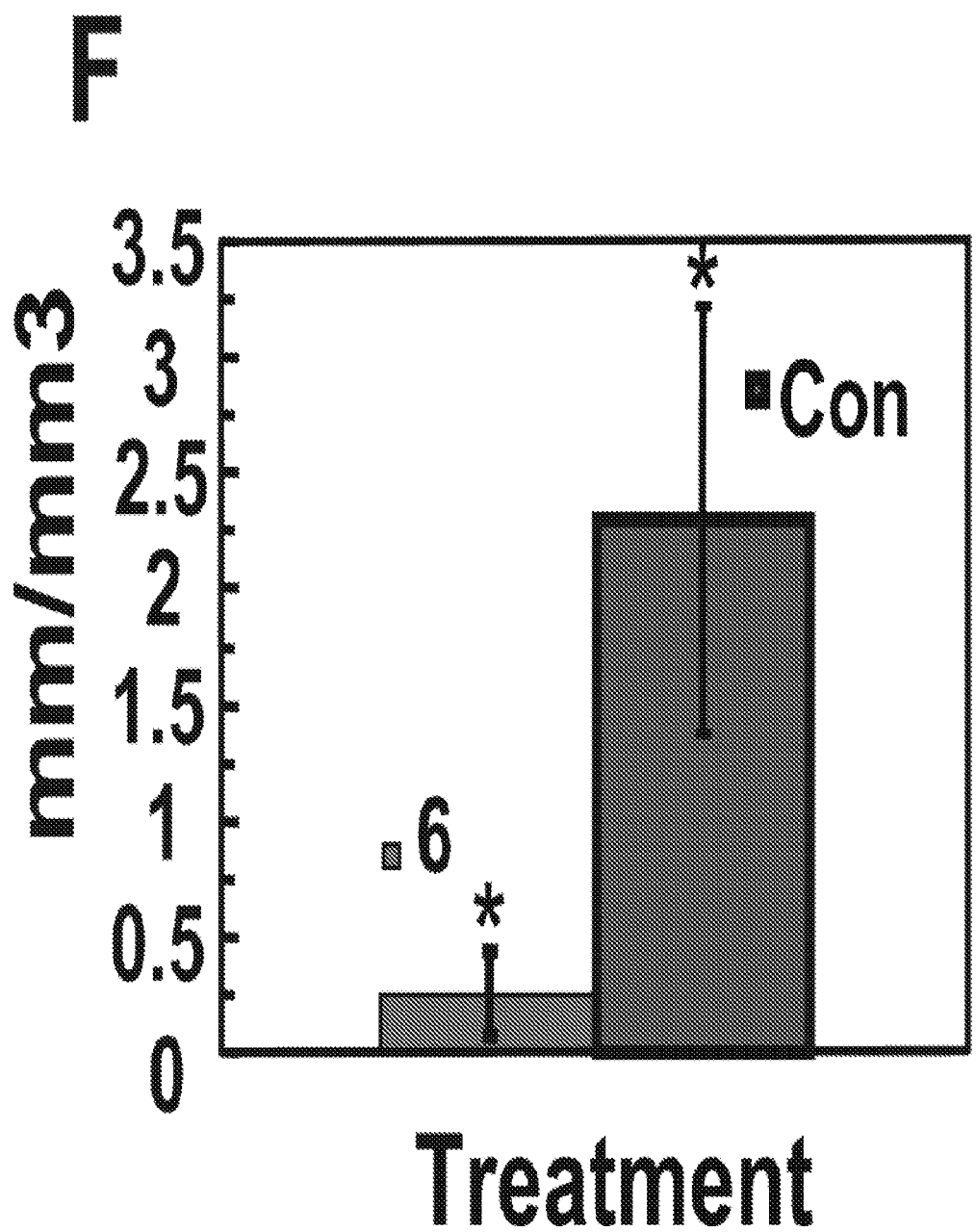

To precisely measure the effects of compound 6 on tumor growth, the tumors were resected and weighed on day 15. Animals treated with 6 produced an average tumor weight of 26.7 mg compared to 74.1 mg for vehicle treated animals (FIG. 5D). At this time, the GFP-labeled blood vessels were imaged and the tumor associated blood vessel density was quantified by measuring the ratio of total blood vessel length to tumor volume (FIGS. 5E and 5F). Tumors treated with 6 were substantially less vascularized relative to vehicle treatment and images of the GFP-labeled tumor vasculature showed a significant reduction in the total blood vessels present (FIG. 5E). The mean vessel length/tumor volume was 2.5 mm/mm$^3$ compared to 0.2 mm/mm$^3$ for vehicle and 6, respectively (FIG. 5F). Theses results indicate that compound 6 prevents tumor growth in an orthotopic pancreatic carcinoma model.

Example 17

Effects of Compound 6 on Tumor Growth after Oral Administration

Figure 10A:
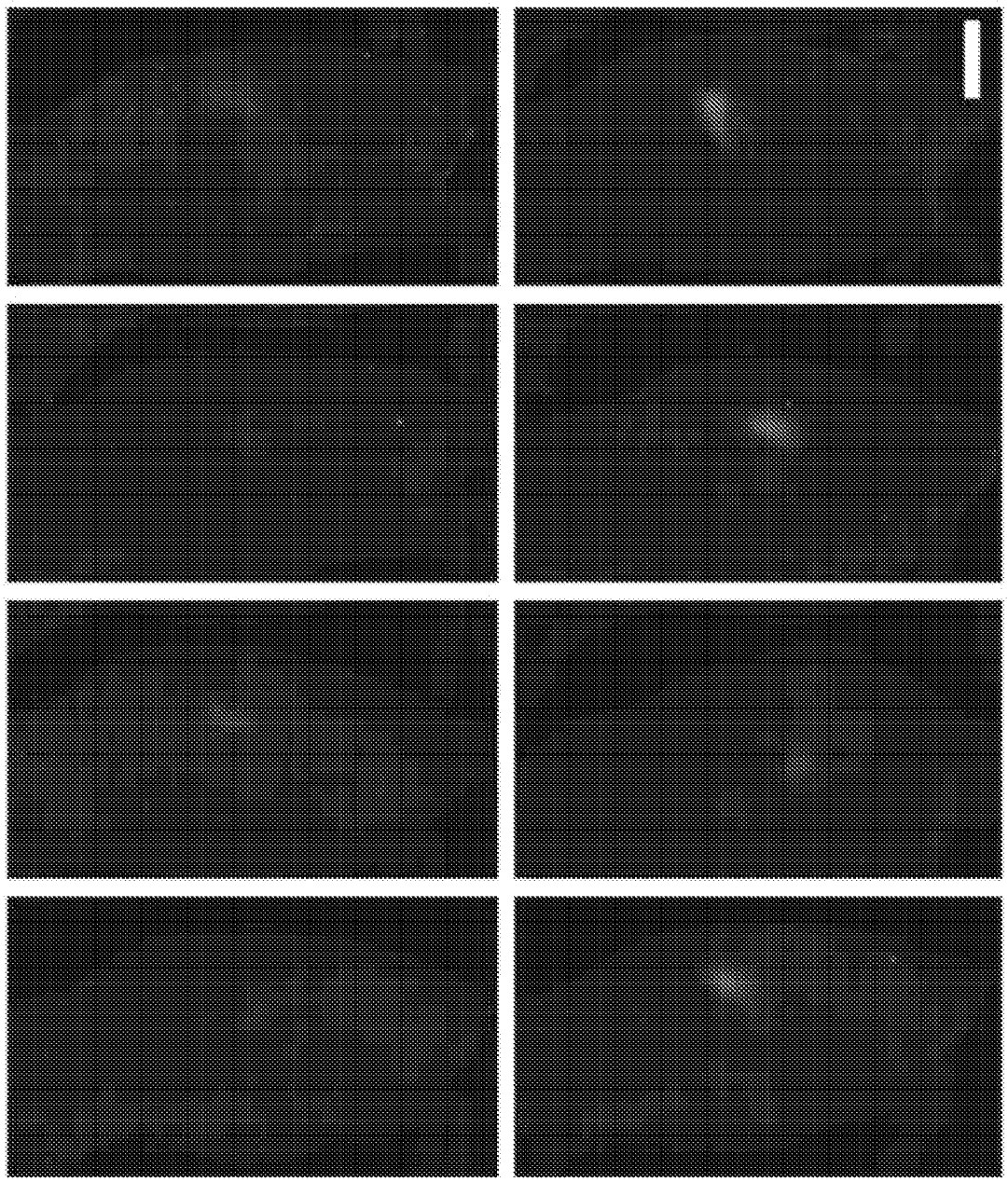
FIG. 10A-B illustrate results of compound 6 being orally active against orthotopic renal cell carcinoma.
Figure 10B:
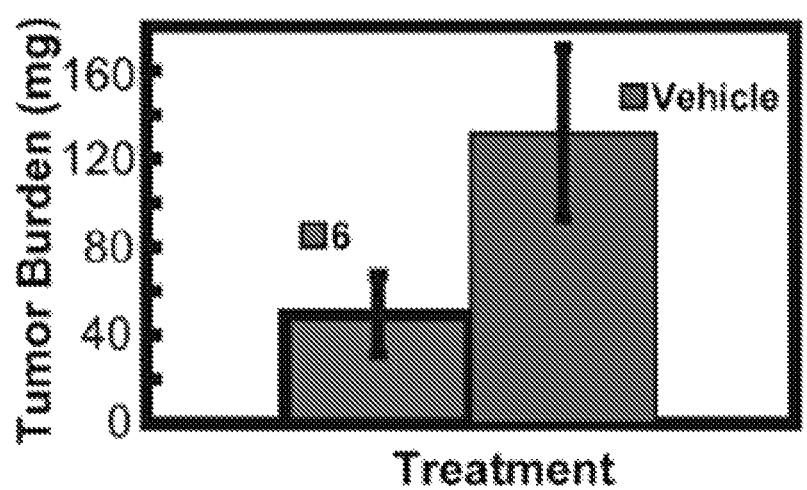

To test the effects of 6 on tumor growth after oral administration, human SN12C renal cells expressing RFP were injected into the kidney capsule of nude mice and tumors were allowed to develop for 7 days. Compound 6 was dosed at 100 mg/kg and demonstrated favorable pharmacokinetics with a C. of 4.9 µg/ml, $T_{1/2}$ of 6.1 h, and an $AUC^{0-24h}$ of 8.7 µg*h/ml. Suppression of tumor growth was readily observed in those animals treated with 6 (FIG. 10A). On day 26, the kidneys were excised from these animals and the weight due to tumor was calculated by subtracting the weight of the normal kidney from the weight of the tumor-bearing kidney for each animal. The average tumor burden of the vehicle group was 132±39 mg compared to 49±18 mg for the compound 6 treated group (FIG. 10B). This demonstrates the oral activity of 6 in preventing tumor growth of an orthotopic renal cell carcinoma model.

Example 18

Quantificaiton of the Compound 6 Effect on the ISV Volume

Representative views of zebrafish embryos treated as in FIG. 3A (images represent merged phase and GFP fluorescence views of the head and trunk regions of Tg:fli1-EGFP embryos). Scale bar=200 µm. (FIG. 8C) Quantification of ISV volume from embryos treated as in FIG. 3A. (FIG. 8D) Quantification of ISV volume from embryos treated as in FIG. 3B. To measure the intersegmental vessel (ISV) volume, individual ISVs were digitally isolated using the Imaris countersurface/isosurface functions. 30 independent ISVs from 4 independent embryos were used for the measurement. Reported +/−sem.

Example 19

Effects of Compound 6 Regarding Intimal Hyperplasia in Mice

Figure 11:
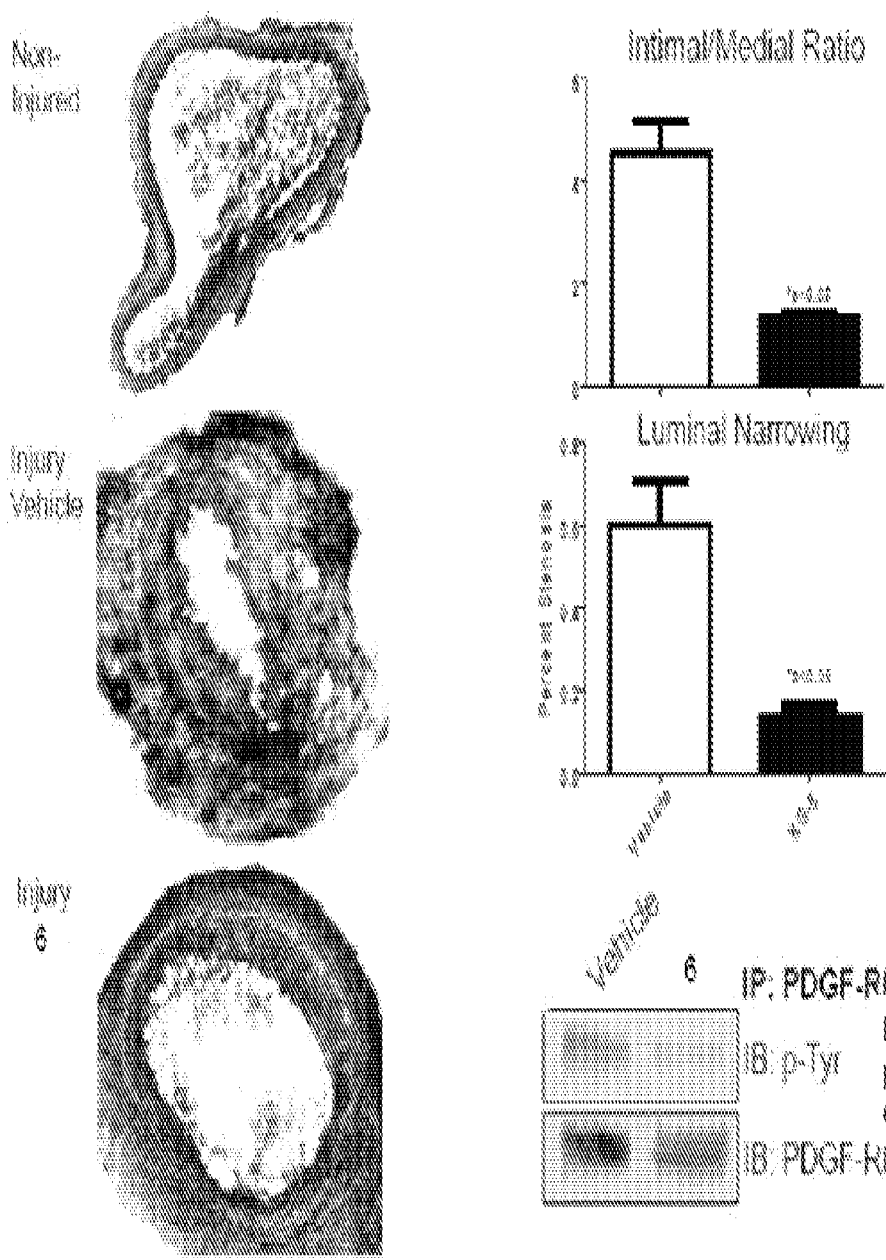
FIG. 11A-E illustrate that compound 6 is orally active against neointimal hyperplasia.

Restenosis is a process that commonly results from balloon angioplasty and/or stent placement resulting in eventual occlusion of arteries by a process described as neointimal hyperplasia (NIH). After arterial injury, an over-proliferation of vascular smooth muscle cells occurs which has previously been shown to be dependent on both PDGFRα/β (Englesbe, et al. (2004) *J Vasc Surg* 39, 440-6) and MAPK pathway activation (Li, et al. (2005) *Circulation* 111, 1672-8; Pintucci, et al. (2006) *Faseb J* 20, 398-400). Therefore, the combination of PDGFRβ/B-RAF inhibition would be an ideal treatment for NIH. As shown in FIG. 1E, compound 6 potently inhibited VSMC viability in the presence of serum and was therefore tested in a mouse model of arterial wire-injury. Mouse carotid arteries were wire-injured and treated the following day with 100 mg/kg, qd, via oral gavage. Representative sections of the injured arteries, stained with hematoxylin and eosin (FIG. 11A), were used to calculate the intimal/medial ratio—a measurement of the thickness of the inner two layers of the artery wall, which correlates with the size of the vessel lumen. Dosing with compound 6 one day after artery injury drastically reduced the intimal/medial ratio (FIG. 11B). As expected by the reduction in the intimal/medial ratio, the percent stenosis is greatly reduced by treatment of compound 6 relative to vehicle treatment (FIG. 11C). As a pharmacodynamic endpoint, representative arteries were excised 4 h after the final dose and lysates were immunoblotted to detect activated PDGFRβ. Treatment of the mice with 6 inhibited PDGFRβ activation in these tissues when compared to vehicle treated mice (FIG. 11D), confirming inhibition of the target in vivo following oral administration.

Example 20

Effects of Compound 6 for Inhibiting Tumor Cell Viability

Compound 6 was shown to have broad significant tumor cell killing or growth inhibition at concentration safe to normal quiescent cells (Table 5). The data showed EC50 of compound 6 is in wide range of tumor lines 100-600 nM which is 15-100 times more potent than sorafenib. Compound 6 also demonstrated differentiated mechanism from PLX4032 and Mek inhibitors via inhibition of wildtype and mutant RAF.

TABLE 5

Potent Effects of compound 6 in RAF and Ras-mutated and non-mutated tumor lines

| Tissue Origin | Tumor Cell Line | Aberration | KG5 EC$_{50}$ (μM) | Sorafenib EC$_{50}$ (μM) | Mek Inhib. (UO126) EC$_{50}$ (μM) |
|---|---|---|---|---|---|
| Melanoma | CHL-1 | — | 0.10 | 6.10 | — |
| Melanoma | SK-MEL-2 | N-Ras | 0.14 | 14.27 | — |
| Melanoma | SK-MEL-28 | B-RAF$^{V600E}$ | 0.40 | 17.60 | — |
| Melanoma | 1205Lu | B-RAF$^{V600E}$ | 0.83 | — | — |
| Breast AC | MDA-MB231 | B-RAF/Ras | 0.48 | >10.00 | — |
| Colon Carcinoma | CT26 | — | 0.71 | — | — |
| Pancreatic AC | XPA1-RFP | K-Ras | 0.28 | — | — |
| Epithelial Carcinoma | A431 | HER1 | 0.43 | — | — |
| Melanoma | M21 | — | 0.45 | — | — |
| Melanoma | M21L | — | 0.42 | — | — |
| Colon | HCT116 | K-Ras | 0.40 | 8.21 | >20.0 |
| Pancreatic (mouse spontaneous model) | R40P | K-Ras | 0.66 | 9.43 | 10.86 |
| Breast | MCF7 | PI3K | 0.68 | >20.0 | >20.0 |
| Colon | HT29 | B-RAF$^{V600E}$ | 0.62 | >20.0 | 4.41 |

Example 21

Application of Compound 6 for Inhibition of Lymphangiogenesis

Figure 12A:
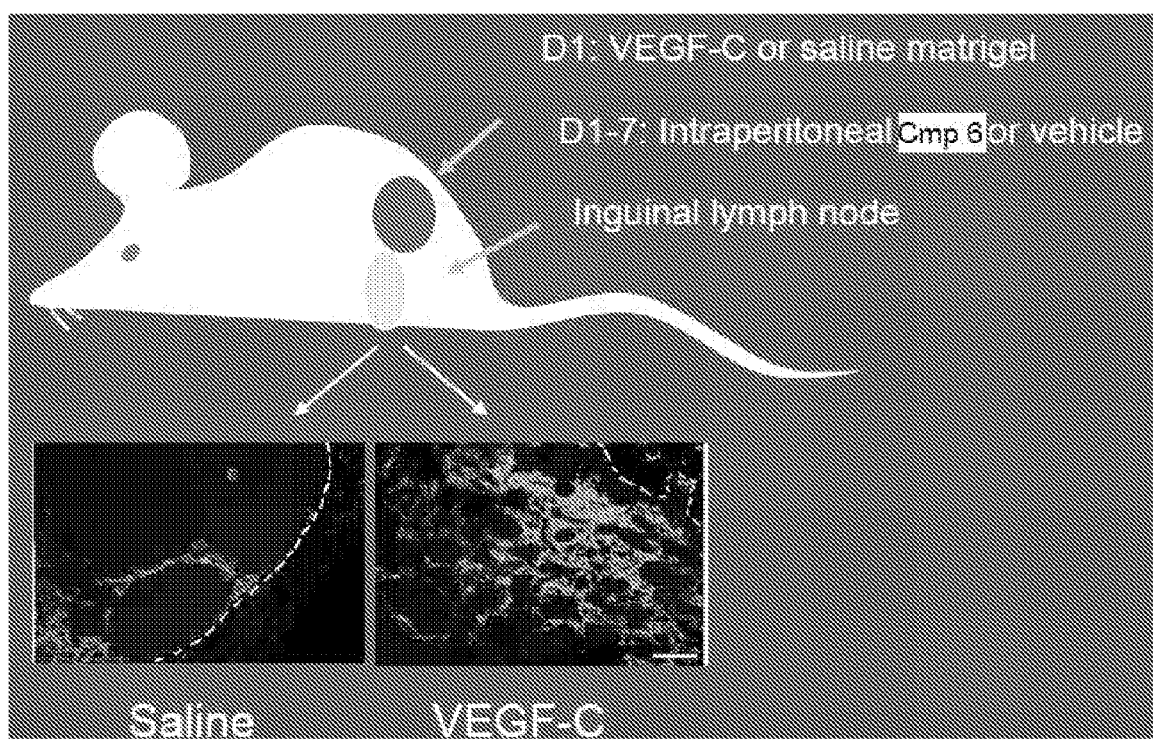
FIG. 12A-B show results of compound 6 as a potent inhibitor of Lymphangiogenesis.
Figure 12B:
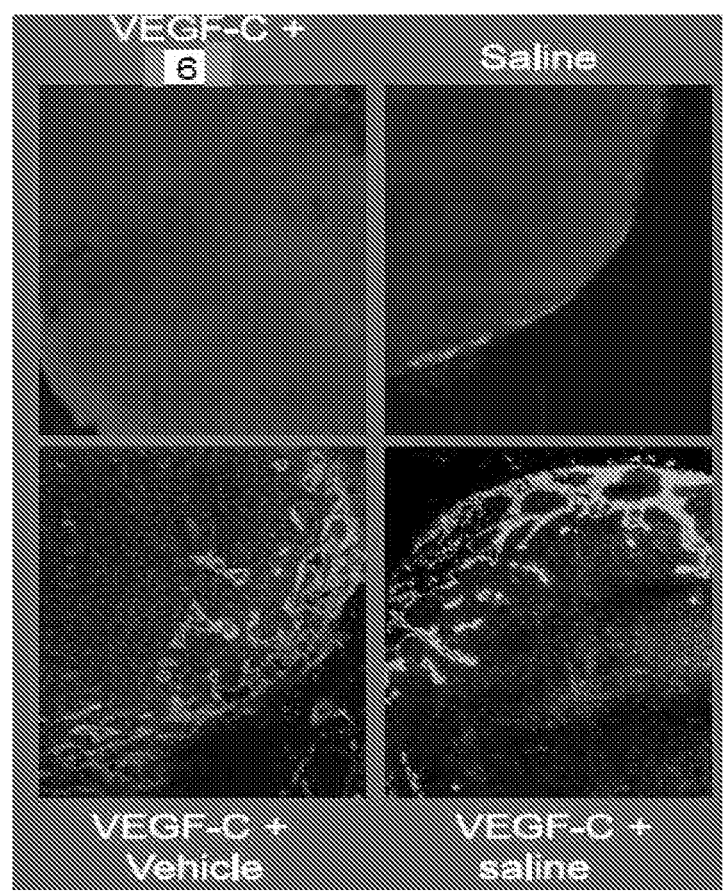

Lymphangiogenesis assays were performed by subcutaneously injecting 350 μl of cold Matrigel containing saline or 1 mg/ml of VEGF-C(R&D Systems, Minneapolis, Minn.) into wild-type C57B1/6 mice. VEGF-C implanted mice were then treated by daily intraperitoneal injections of 200 μl twice daily of saline, 5.25 mg/ml compound 6 or vehicle control (10% HS-15 and 3.33% Dextrose) each day for 7 days, beginning with day 1 (n=7). After 7 days, lymph nodes were removed, embedded in OCT, frozen and sectioned. Thin sections (5 μm) were fixed in ice cold acetone for five minutes, permeabilized in 0.1% Triton X-100 in phosphate buffered saline (PBS), blocked in 8% normal donkey serum diluted in PBS for 1.5 hours at room temperature and then incubated with 2 μg/ml anti-murine Lyve-1 (RDI-103PA50) in 8% normal donkey serum diluted in saline overnight at 4° C. After extensive washing, slides were incubated with 1 μg/ml cross-absorbed donkey anti-rabbit IgG (H+L) conjugated with Alexa Fluor 488 (Invitrogen). Slides were counterstained with DAPI. Coverslips were mounted with Dako Cytomation fluorescent mounting medium (Dako Corporation, Carpinteria, Calif.). At least five microscopic fields per tissue section/mouse were analyzed for quantification studies. Results are shown in FIGS. 12A and 12B.

Example 22

Application of Compound 6 for Treatment of Fibrosis

Compound 6 (50 mg/Kg/day, oral) is evaluated for treatment of fibrosis with 90 patients (two groups –45 patients with drug and 45 patients with placebo) referred to the Interstitial Lund Disease clinic who is undergoing evaluation and or treatment for a new diagnosis of ILD. This can include patients referred for presumed pulmonary fibrosis/interstitial pneumonitis (IPF, UIP, NSIP), sarcoidosis, hypersensitivity pneumonitis, cryptogenic organising pneumonia, drug-induced, or other idiopathic ILDs. The patients are evaluated after 6 months of treatment. Patients with treatment of compound 6 find improvement over placebo group.

Example 23

The Growth Inhibitory Properties of Compound 6 on Tumor Cells

Compound 6 was profiled in the NCI60 panel by the NCI Developmental Therapeutics Program and demonstrated an average growth inhibitory concentration (GI50) of 490 nM with potent growth inhibition across the entire panel of cell lines. See FIG. 13A. Additionally, compounds 6, 35, or 37 were compared to sorafenib, PLX 4720 or L779,450 in a cell proliferation assay. A549 cells, which endogenously express oncogenic K-RAS, were plated at 2500 cells/well of a 96-well plate in low serum DMEM (0.5% fetal bovine serum) overnight. The next morning, compounds were serially diluted in DMSO and resuspended in fresh DMEM+0.5% medium, which was added to the cells for 72 h. At this time point the cells were fixed and proliferation was quantified using an ELISA for bromodeoxyuriding incorporation (BrdU ELISA, Millipore, Inc.). BrdU incorporation occurs during S phase and is the classical method for determining cell proliferation rates. In FIG. 14B-C, BrdU incorporation is expressed as a percentage of the BrdU incorporation occurring in cells treated with 0.1% DMSO as control. A dotted line represents the growth rate of cells treated with DMSO alone. Compound 6, 35, or 37, all inhibitor cell proliferation (FIG. 13B), whereas the commercially available RAF inhibitors (sorafenib, PLX 4720, or L-779,450) all induce hyperproliferation when compared to the DMSO treated control cells. (FIG. 13C)

Example 24

Comparision of Compound 6 with Sorafenib Regarding Phosphorylation on CRAF S338

R40P cells are derived from a spontaneous pancreatic adenocarcinoma mouse model which expresses K-ras$^{G12D}$ while p16/Ink4a/ARF is lost. R40P cells were starved for 12 h and treated for 12 h with a MEK inhibitor (U0126), sorafenib, and compound 3 at 5 μM. A dose response of 5, 2.5 and 1.25 μM was used for compound 6. At this time the cells were lysed and protein levels were quantified by BCA analysis. The lysates were then loaded on an SDS-PAGE gel and transferred to nitrocellulose for Western blotting. Immunoblotting was performed with the following antibodies: pMEK1/2 S217/S221 (Cell Signaling), pCRAF S338 (Cell Signaling), and total CRAF (BD Biosciences). Chemilluminescence was used for detection on film. It is important to note that all ATP-competitive inhibitors we have utilized demonstrate a similar induction of phosphorylation on CRAF S338.

Figure 14:
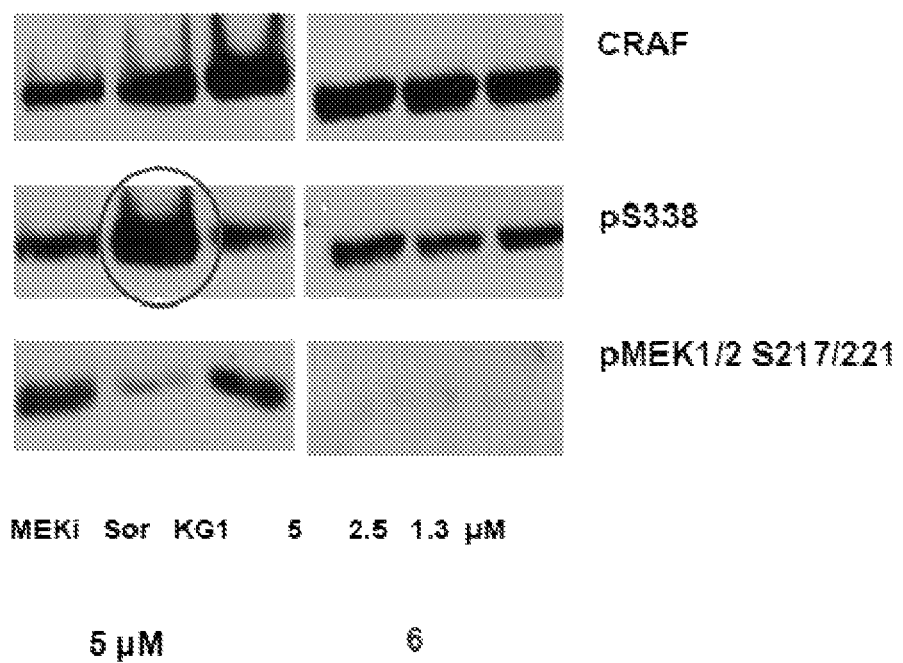
FIG. 14 shows that sorafenib induces an increase in phosphorylation on CRAF S338, while Compound 6 does not promote this increase.

FIG. 14 shows that sorafenib induces an increase in phosphorylation on CRAF S338, while Compound 6 does not promote this increase.

Example 25

Figure 15A:
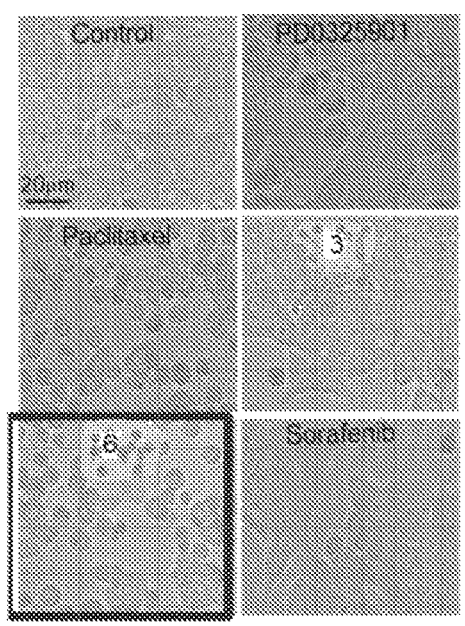
FIG. 15A-B show that exemplary compounds cause a G2/M arrest at prometaphase.
Figure 15B:
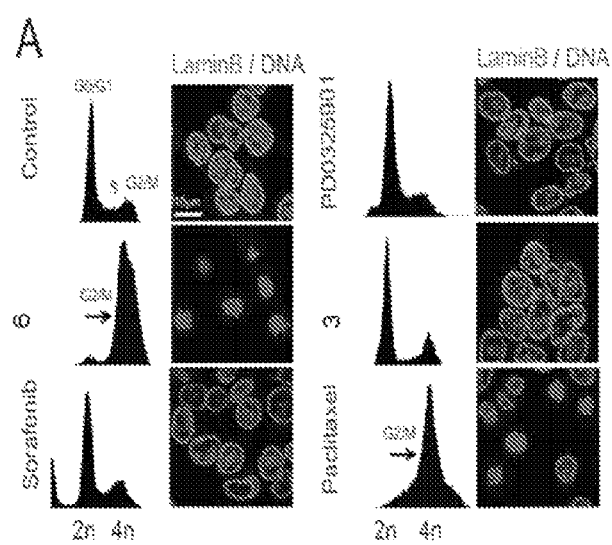

Cell Cycle and Confocal Microscopy Analysis of XPA-1 Cells Treated with the allosteric RAF inhibitor compounds Cell cycle and confocal microscopy analysis of XPA-1 cells treated with the allosteric RAF inhibitor compound 6, the ATP-competitive inhibitor sorafenib, the MEK inhibitor (PD0325901), compound 3 or paclitaxel. Cell cycle analysis revealed that compound 6 treatment led to a G2/M arrest in all tumor cell lines tested, mimicking the activity of the antimitotic agent paclitaxel, while compound 3 a structural analogue of compound 6 that inhibits c-Kit, Flt-3 and PDGFR, but not RAF, showed no effect. See FIGS. 15A and 15B. Importantly, treatment of cells with sorafenib or the MEK inhibitor PD0325901, led to ERK inhibition as expected (not shown), yet had no effect on mitotic progression. For cell cycle analysis, cells were grown in complete DMEM+10% FBS in the presence of each inhibitor and harvested after 20 h of inhibitor treatment. Cell cycle analysis was performed by flow cytometry following propidium iodide staining. The cells were harvested, fixed with ice cold methanol, treated for 45 min with 10 µg/ml of RNAse and resuspended in PBS containing 10 µg/ml of PI, and analysed by flow cytometry. Cell cycle analysis was performed in cells treated with compound 6, sorafenib, or MEK inhibitor (PD0325901) at 5 µM concentration or paclitaxel at 100 nM. For corresponding confocal microscopy images, cells attached to coverslips were fixed with cold methanol and permeabilized in PBS containing 0.1% triton X-100 for two minutes and blocked for 60 minutes, at room temperature with 2% BSA in PBS. Cells were stained with the DNA binding dye TOPRO-3 (Invitrogen) to label the DNA and laminB (Santa Cruz) to label the nuclear envelope. The anti-Lamin B antibody was used at a 1:100 dilution for two hours at room temperature. After washing several times with PBS, cells were stained for two hours at room temperature, with secondary antibody diluted 1:300 and co-incubated with TOPRO-3 (1:500) (Invitrogen). Samples were mounted in Vectashield hard-set mounting media (Vector Laboratories) and imaged on a Nikon Eclipse C1 confocal microscope with a 1.4 NA 60× oil-immersion lens, using minimum pinhole (30 µm). Images were captured and processed using EZ-C1 3.50 imaging software (Nikon, Inc). Scale bars, 10 µm.

Example 26

Cell Cycle Analysis of Compound 6

Figure 16:
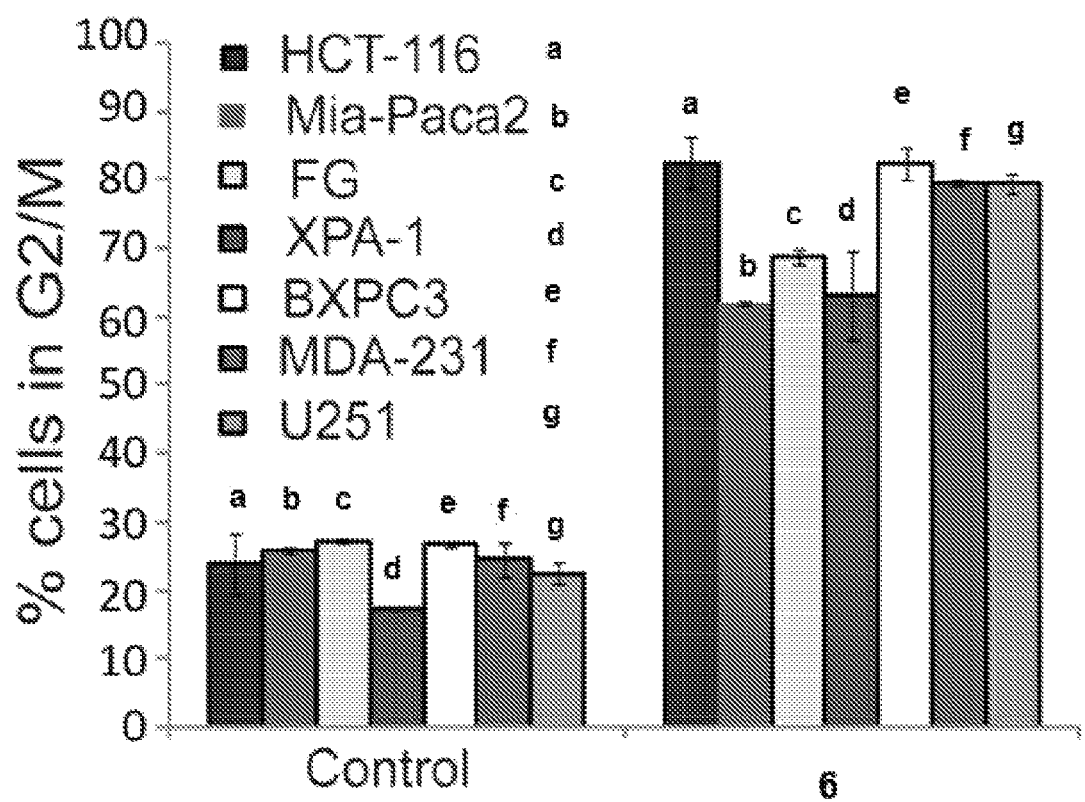
FIG. 16 shows exemplary compound 6 arresting a wide variety of tumor cell lines in G2/M. The graph represents the % of cells arrested in G2/M after treatment with 5 μM compound 6 compared to 0.1% DMSO control. The graph depicts G2/M quantification of human colon (HCT-116), pancreatic (Mia-Paca2, FG, XPA-1, BXPC3), breast (MB-MDA-231) and brain (U251) cancer cell lines. Error bars represent s.d. (n=4).

Cell cycle analysis was performed by FACS. See FIG. 16. The graph represents the % of cells arrested in G2/M after treatment with 5 µM compound 6 compared to 0.1% DMSO control. The graph depicts G2/M quantification of human colon (HCT-116), pancreatic (Mia-Paca2, FG, XPA-1, BXPC3), breast (MB-MDA-231) and brain (U251) cancer cell lines. Error bars represent s.d. (n=4).

Example 27

Analysis of Compound 6 Against Melanoma Tumor Growth In Vivo

Figure 17:
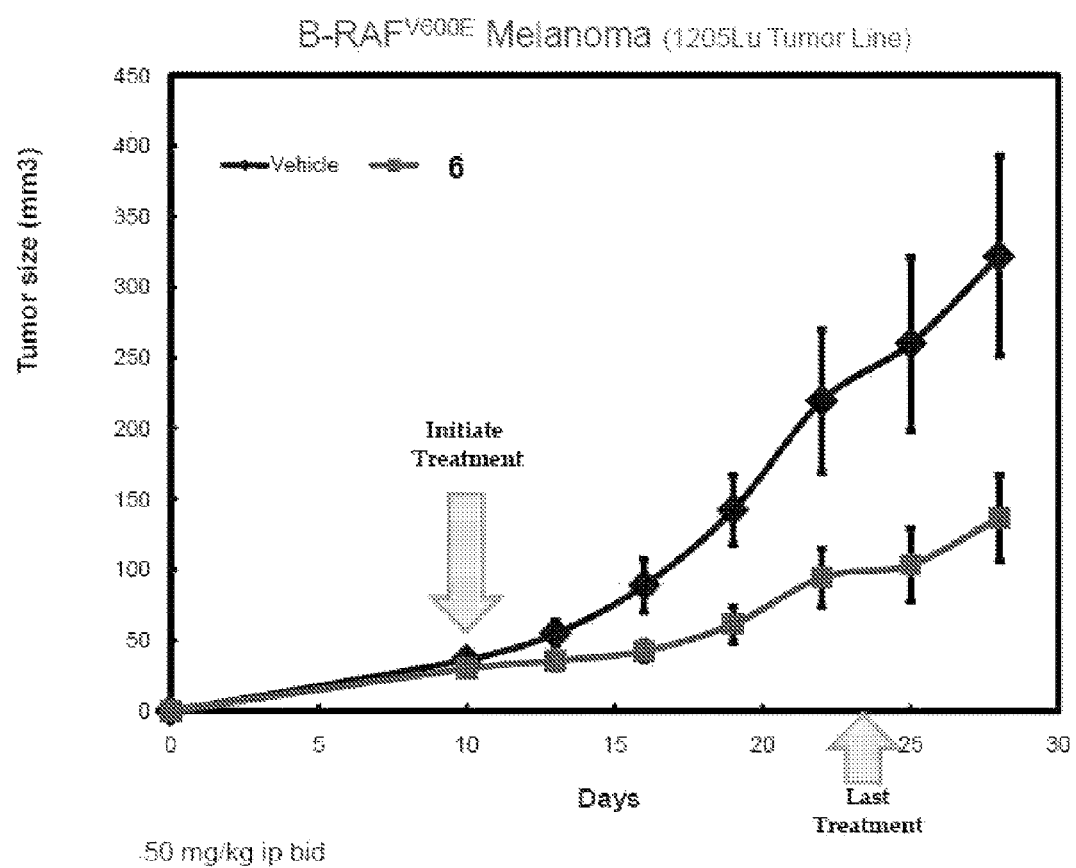
FIG. 17 demonstrates that compound 6 suppresses melanoma tumor growth in vivo.

Human 1205 Lu melanoma cells, which express BRAF V600E, were subcutaneously implanted into the flank of 6-8 week old female Nu/Nu mice. The tumor cells were trypsinized and resuspendend in 1:1 PBS:growth factor depeleted Matrigel (BD Biosciences) and 50 µg containing 1×10^6 cells was injected into the flank. An excess of mice bearing tumors were utilized and groups of 6 animals were chosen based on the symmetry of the tumor and randomized to give each group an average of 50 mm$^3$ (day 10). Treatment was initiated at this point with vehicle or 50 mg/kg of compound 6, bid, ip for 2 weeks (through day 24). The vehicle was 10% HS-15 (known as Solutol, BASF, Inc.) in 3.33% dextrose. Tumor growth was monitored by measuring the tumor length and width with precision calipers every 3 days and calculating tumor volume using the following formula: Tumor volume=0.5*(length)*(width)$^2$, provided the smaller measurement was utilized as the length. FIG. 17 demonstrates that compound 6 suppresses melanoma tumor growth in vivo.

Example 28

Analysis of Compound 6 Against Breast Cancer Growth In Vivo

Tumors were generated by injection of MDA-MB231 human breast carcinoma cells (1×10$^6$ tumor cells in 50 µl of sterile PBS) into the mammary fatpad of 6-8 week old female Nu/Nu mice. Tumors were allowed to grow and the mice were randomized into two groups with an average tumor volume of 100 mm$^3$. Mice were dosed (bid, ip) with vehicle (10% HS-15, 3.33% dextrose) or 50 mg/kg compound 6. Tumor growth was monitored by measuring the tumor length and width with precision calipers every 2 days and calculating tumor volume using the following formula: Tumor volume=0.5*(length)*(width)$^2$, provided the smaller measurement was utilized as the length. In FIG. 18A, the MDA-MB-231 tumors were treated for three consecutive days, and the tumors were resected 1 h following the final vehicle or compound 6 dose and stained for phosphorylation on CRAF S338. Compound 6 clearly inhibits phosphorylation of S338 in the breast tumors. This suggests that pS338 CRAF could serve as a potential biomarker for measuring activity of the drug in clinical settings. Scale bar 20 µM. FIG. 18B displays the tumor growth profile after treatment with compound 6 or vehicle. Compound 6 suppresses tumor growth as compared to vehicle treatment. FIG. 18C shows the pS338 CRAF levels in the MDA-MB231 cells in vitro. The cells were treated with DMSO (Ctrl), compound 6, or sorafenib at 5 µM for 6 h and cell lysates were resolved on 10% SDS-PAGE and immunoblotting was performed with the following antibodies: pS338 CRAF (Cell Signaling), CRAF (BD Pharmingen), and Actin (Sigma), all diluted 1:1000. Cells were lysed in RIPA buffer (50 mM Tris pH 7.4, 100 mM NaCl, 0.1% SDS, 1.0% TritonX-100, 1% deoxycholate) supplemented with complete protease inhibitor mixture (Roche), 50 mM NaF, and 1 mM Na$_3$VO$_4$ and centrifuged at 13,000 g for 10 min at 4° C. Protein concentration was determined by BCA assay and 30 µg of protein was loaded per lane of 10% SDS-PAGE gel. Immunohistochemistry in FIG. 18A was performed according to the manufacturer's recommendations (Vector Labs), on 5 μM sections of paraffin-embedded tumors from the orthotopic xenograft breast cancer mouse model (MDA-MB231). For phospho-S338 CRAF immunohistochemistry, antigen retrieval was performed in citrate buffer pH 6.0 at 95° C. for 20 min. Sections were treated with 0.3% $H_2O_2$ for 30 min, blocked in normal goat serum, PBS-T for 30 min followed by Avidin-D and then incubated overnight at 4° C. with primary antibody against pS338 CRAF (Thermo Scientific) diluted 1:100 in blocking solution. Tissue sections were washed and then incubated with biotinylated secondary antibody (1:500, Jackson ImmunoResearch) in blocking solution for 1 h. Sections were washed & incubated with Vectastain ABC (Vector Labs) for 30 min. Staining was developed using a Nickel-enhanced diamino-benzidine reaction (Vector Labs) and sections were counter-stained with hematoxylin.

Example 29

Cell Viability Assays

Figure 19C:
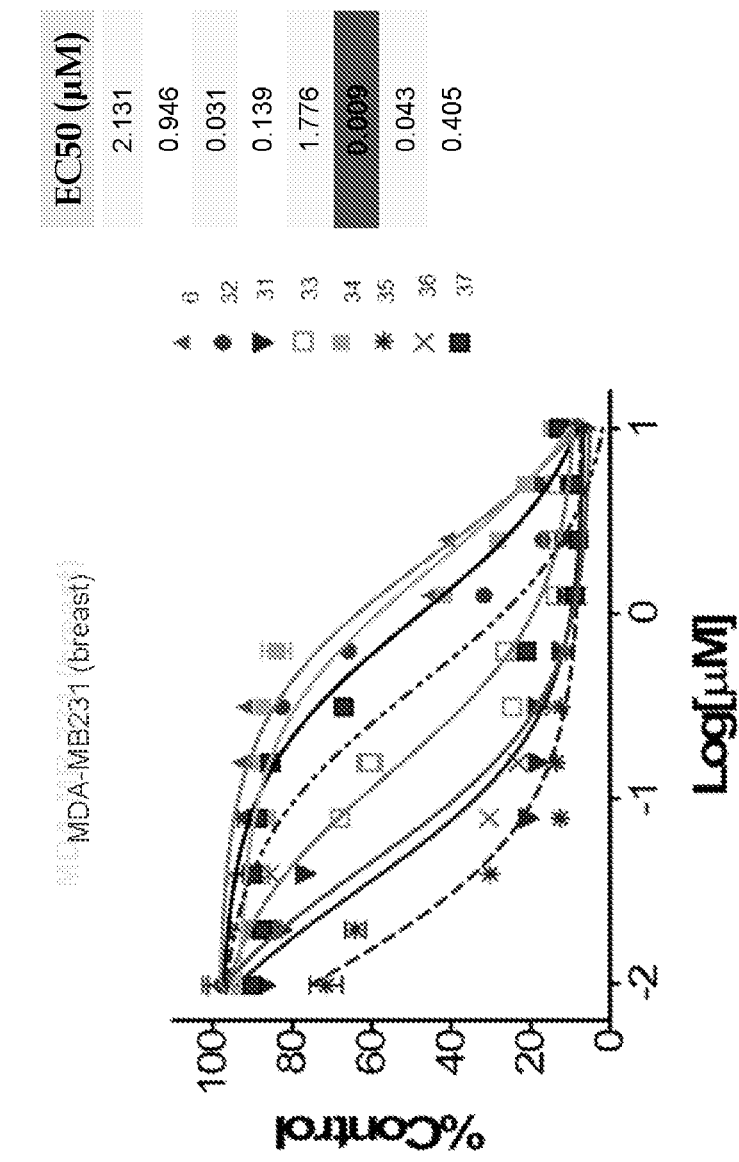

Tumor cells (A549 (FIG. 19A), T47D (FIG. 19B), and MDA-MB231 (FIG. 19C)) were plated at 2500 cells/well of a 96-well plate in complete growth medium (DMEM+10% FBS, antibiotic/antimycotic, fungizone, L-glutamine, sodium pyruvate, and non-essential amino acids). The cells were allowed to grow overnight and then serial dilutions of the corresponding compounds in DMSO were added to fresh complete growth medium and added to the cells for 72 h. Cell viability was measured by adding MTT (Sigma) at 5 mg/ml for 4 h to the cells and then removing the medium and resuspending each well in 50 μl DMSO to solubilize the crystals. The 96-well plates were read on a plate-scanning spectrophotometer (BioTek) at an absorbance of 560 nm. The 11 pt cell viability curves were plotted using GraphPad software and EC50s were calculated using the software and the non-linear regression feature. Compounds such as compound 37 and compound 35 demonstrate greatly improved potency relative to compound 6 in each cell line tested-reaching single digit nM EC50s for inhibiting cell viability in some instances.

Example 30

Parenteral Composition

To prepare a parenteral pharmaceutical composition suitable for administration by injection, 100 mg of a water-soluble salt of a compound 6 is dissolved in DMSO and then mixed with 10 mL of 0.9% sterile saline. The mixture is incorporated into a dosage unit form suitable for administration by injection.

Example 31

Oral Composition

To prepare a pharmaceutical composition for oral delivery, 100 mg of a compound 6 is mixed with 750 mg of starch. The mixture is incorporated into an oral dosage unit for, such as a hard gelatin capsule, which is suitable for oral administration.

Example 32

Sublingual (Hard Lozenge) Composition

To prepare a pharmaceutical composition for buccal delivery, such as a hard lozenge, mix 100 mg of a compound 6 with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 33

Fast-Disintegrating Sublingual Tablet

A fast-disintegrating sublingual tablet is prepared by mixing 48.5% by weigh of a compound 6, 44.5% by weight of microcrystalline cellulose (KG-802), 5% by weight of low-substituted hydroxypropyl cellulose (50 ÿm), and 2% by weight of magnesium stearate. Tablets are prepared by direct compression (*AAPS PharmSciTech.* 2006; 7(2):E41). The total weight of the compressed tablets is maintained at 150 mg. The formulation is prepared by mixing the amount of compound of Formula (I) with the total quantity of microcrystalline cellulose (MCC) and two-thirds of the quantity of low-substituted hydroxypropyl cellulose (L-HPC) by using a three dimensional manual mixer (lnversina®, Bioengineering AG, Switzerland) for 4.5 minutes. All of the magnesium stearate (MS) and the remaining one-third of the quantity of L-HPC are added 30 seconds before the end of mixing.

Example 34

Inhalation Composition

To prepare a pharmaceutical composition for inhalation delivery, 20 mg of a compound 6 is mixed with 50 mg of anhydrous citric acid and 100 mL of 0.9% sodium chloride solution. The mixture is incorporated into an inhalation delivery unit, such as a nebulizer, which is suitable for inhalation administration.

Example 35

Rectal Gel Composition

To prepare a pharmaceutical composition for rectal delivery, 100 mg of a compound 6 is mixed with 2.5 g of methylcelluose (1500 mPa), 100 mg of methylparaben, 5 g of glycerin and 100 mL of purified water. The resulting gel mixture is then incorporated into rectal delivery units, such as syringes, which are suitable for rectal administration.

Example 36

Topical Gel Composition

To prepare a pharmaceutical topical gel composition, 100 mg of a compound 6 is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topicl administration.

Example 37

Ophthalmic Solution Composition

To prepare a pharmaceutical opthalmic solution composition, 100 mg of a compound 6 is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 38

Nasal Spray Solution

To prepare a pharmaceutical nasal spray solution, 10 g of a compound 6 is mixed with 30 mL of a 0.05M phosphate buffer solution (pH 4.4). The solution is placed in a nasal administrator designed to deliver 100 D of spray for each application.

The examples and embodiments described herein are for illustrative purposes only and various modifications or changes suggested to persons skilled in the art are to be included within the spirit and purview of this application and scope of the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

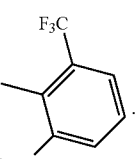

What is claimed is:

1. A method for treating cancer in a human subject comprising administering to a patient in need a compound having the structure:

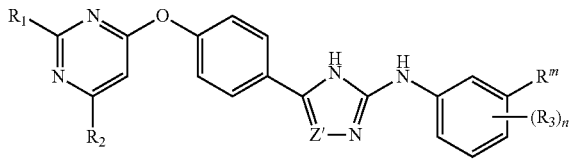

or an N-oxide, N,N'-dioxide, N,N',N''-trioxide, or a pharmaceutically acceptable salt thereof,
wherein:
$R_1$ and $R_2$ are independently hydrogen, optional substituted alkyl, halogen, optional substituted amine, $NH_2$, optional substituted alkyoxy, optional substituted thioalkyl, $CF_3S$ optional substituted alkylsulfinyl or optional substituted alkylsulfonyl;
Z' is N or C;
$R^m$ is $C_{1-6}$ alkyl, or halogen substituted $C_{1-6}$ alkyl; and
$R_3$ is independently a $C_{1-6}$ alkyl, halogen substituted $C_{1-6}$ alkyl, halogen substituted $C_{1-6}$ alkoxy, or $C_{3-10}$cycloalkyl; or,
$R^m$ and $R_3$ are joined to form a five to seven membered carbocycle; and
n is 1-4;
that (i) stabilizes a protein kinase in the inactive state and (ii) is not an ATP competitive inhibitor of the protein kinase in the active state; and wherein the cancer is selected from melanoma, breast cancer, pancreatic cancer, lung cancer, kidney cancer, and colon cancer.

2. The method of claim 1, wherein the compound is a selective type II inhibitor.

3. The method of claim 2, wherein the compound is a selective type II inhibitor of RAF kinase, PDGF receptor, c-KIT, FLT3, CSF1R or CDK11.

4. The method of claim 3, wherein said RAF kinase is B-RAF kinase.

5. The method of claim 1, wherein the compound arrests tumor cells in G2/M.

6. The method of claim 1, wherein the compound inhibits the phosphorylation of S338of C-RAF.

7. A method for suppressing, preventing or inhibiting lymphangiogenesis, angiogenesis and/or growth of a cancer tumor, which comprises contacting the tumor with a compound having the structure:

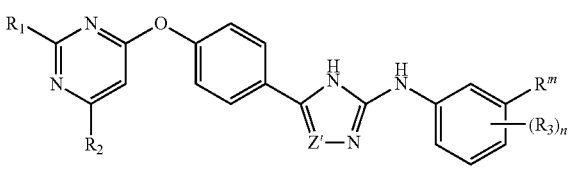

or an N-oxide, N,N'-dioxide, N,N',N''-trioxide, or a pharmaceutically acceptable salt thereof,
wherein:
$R_1$ and $R_2$ are independently hydrogen, optional substituted alkyl, halogen, optional substituted amine, $NH_2$, optional substituted alkyoxy, optional substituted thioalkyl, $CF_3S$ optional substituted alkylsulfinyl or optional substituted alkylsulfonyl;
Z' is N or C;
$R^m$ is $C_{1-6}$ alkyl, or halogen substituted $C_{1-6}$ alkyl; and
$R_3$ is independently a $C_{1-6}$ alkyl, halogen substituted $C_{1-6}$ alkyl, halogen substituted $C_{1-6}$ alkoxy, or $C_{3-10}$cycloalkyl; or, optionally,
$R^m$ and $R_3$ are joined to form a five to seven membered carbocycle; and
n is 1-4;
that (i) stabilizes a protein kinase in the inactive state and (ii) is not an ATP competitive inhibitor of the protein kinase in the active state; and wherein the cancer is selected from melanoma breast cancer sancreatic cancer luncancer kidne cancer and colon cancer.

8. The method of claim 7, wherein the compound is a selective type II inhibitor.

9. The method of claim 8, wherein the compound is a selective type II inhibitor of RAF kinase, PDGF receptor, c-KIT, FLT3, CSF1R or CDK11.

10. The method of claim 9, wherein said RAF kinase is B-RAF kinase.

11. The method of claim 7, wherein the compound arrests tumor cells in G2/M.

12. The method of claim 7, wherein the compound inhibits the phosphorylation of S338of C-RAF.

13. A method for inhibiting phosphorylation of S338of CRAF and/or RAF dimerization in a cancer comprising contacting a cell with a compound having the structure:

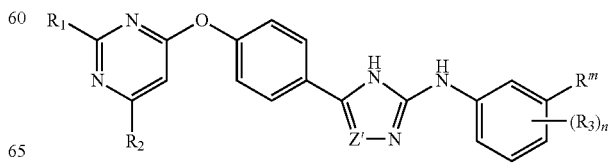

or an N-oxide, N,N'-dioxide, N,N',N''-trioxide, or a pharmaceutically acceptable salt thereof,
wherein:
$R_1$ and $R_2$ are independently hydrogen, optional substituted alkyl, halogen, optional substituted amine, $NH_2$, optional substituted alkyoxy, optional substituted thioalkyl, $CF_3S$ optional substituted alkylsulfinyl or optional substituted alkylsulfonyl;
Z' is N or C;
$R'''$ is $C_{1-6}$ alkyl, or halogen substituted $C_{1-6}$ alkyl; and
$R_3$ is independently a $C_{1-6}$ alkyl, halogen substituted $C_{1-6}$ alkyl, halogen substituted $C_{1-6}$ alkoxy, or $C_{3-10}$cycloalkyl; or, optionally,
$R'''$ and $R_3$ are joined to form a five to seven membered carbocycle; and
n is 1-4;
that (i) stabilizes the protein kinase in the inactive state and (ii) is not an ATP competitive inhibitor of the protein kinase in the active state; and wherein the cancer is selected from melanoma breast cancer sancreatic cancer luncancer kidne cancer and colon cancer.

14. The method of claim 13, wherein the compound is a selective type II inhibitor.

15. The method of claim 14, wherein the compound is a selective type II inhibitor of RAF kinase, PDGF receptor, c-KIT, FLT3, CSF1R or CDK11.

16. The method of claim 15, wherein said RAF kinase is B-RAF kinase.

17. The method of claim 13, wherein the compound arrests tumor cells in G2/M.

18. The method of claim 1, wherein the cancer is resistant, refractory or non-responsive to a type I inhibitor of the protein kinase, a pan-RAF kinase drug, a VEGF-targeted therapy, or an ATP-competitive inhibitor.

19. The method of claim 1, wherein the compound is selected from the group consisting of:

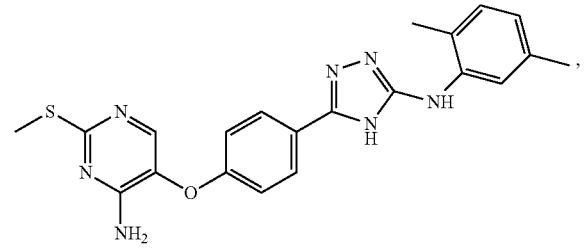

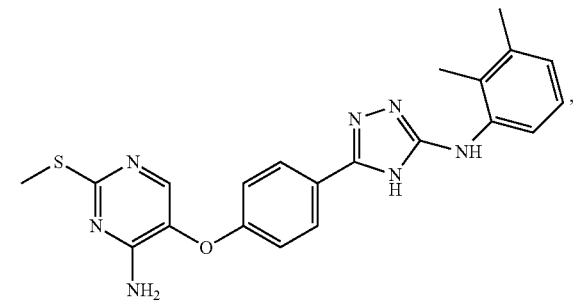

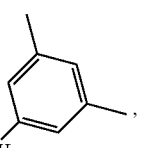

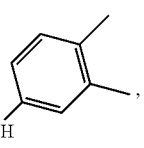

and